United States Patent [19]
Wang et al.

[11] Patent Number: 6,015,912
[45] Date of Patent: Jan. 18, 2000

[54] SPIROCYCLIC CONTAINING HYDROXAMIC ACIDS USEFUL AS METALLOPROTEASE INHIBITORS

[75] Inventors: Zhe Wang, Wilmington, Del.; Neil Gregory Almstead, Loveland, Ohio; Rimma Sandler Bradley, Fairfield, Ohio; Michael George Natchus, Glendale, Ohio; Biswanath De, Cincinnati, Ohio; Stanislaw Pikul, Mason, Ohio; Yetunde Olabisi Taiwo, West Chester, Ohio

[73] Assignee: The Procter & Gamble Company, Cincinnati, Ohio

[21] Appl. No.: 08/918,328

[22] Filed: Aug. 26, 1997

Related U.S. Application Data

[60] Provisional application No. 60/024,766, Aug. 28, 1996.

[51] Int. Cl.[7] .................. C07D 209/96; C07D 209/54; C07D 491/00; C07D 495/00; A61K 31/40
[52] U.S. Cl. .................. 548/408; 514/409; 514/424; 548/409; 548/410; 548/542
[58] Field of Search ............. 548/409, 408, 548/410, 542; 514/409, 424

[56] References Cited

U.S. PATENT DOCUMENTS

| | | | |
|---|---|---|---|
| 4,521,537 | 6/1985 | Kosley et al. | 514/302 |
| 4,555,579 | 11/1985 | Rovnyak | 548/409 |
| 4,709,046 | 11/1987 | Krapcho | 548/409 |
| 4,735,944 | 4/1988 | Bolliger | 514/278 |
| 4,847,384 | 7/1989 | Kapa et al. | 548/409 |
| 4,918,105 | 4/1990 | Cartwright et al. | 514/575 |
| 4,996,358 | 2/1991 | Handa et al. | 562/621 |
| 5,101,047 | 3/1992 | Ballschuh et al. | 548/570 |
| 5,183,900 | 2/1993 | Galardy et al. | 548/495 |
| 5,189,178 | 2/1993 | Galardy et al. | 548/495 |
| 5,300,674 | 4/1994 | Crimmin et al. | 560/42 |
| 5,310,763 | 5/1994 | Campion et al. | 514/575 |
| 5,420,150 | 5/1995 | Guillaumet et al. | 514/409 |
| 5,534,541 | 7/1996 | Drauz et al. | 514/448 |

FOREIGN PATENT DOCUMENTS

| | | |
|---|---|---|
| 0231081 | 8/1987 | European Pat. Off. |
| 0498665 | 2/1992 | European Pat. Off. |
| 0575844 | 12/1993 | European Pat. Off. |
| 0606046 | 7/1994 | European Pat. Off. |
| 4127842 | 2/1993 | Germany |
| 1241512 | 8/1971 | United Kingdom ........ 548/409 |
| 2268934 | 1/1994 | United Kingdom |
| WO 91/02716 | 3/1991 | WIPO |
| WO 93/00082 | 6/1992 | WIPO |
| WO 92/17460 | 10/1992 | WIPO |
| WO 93/20047 | 4/1993 | WIPO |
| WO 93/09090 | 5/1993 | WIPO |
| WO 93/21942 | 11/1993 | WIPO |
| WO 94/10990 | 5/1994 | WIPO |
| WO 95/35275 | 12/1995 | WIPO |

OTHER PUBLICATIONS

Chapman, K.T., et al., "Inhibition of Matrix Metalloproteinases by N–Carboxyalkyl Peptides", *Journal of Medicinal Chemistry*, vol. 36 (1993), pp. 4293–4301.

Johnson, w.K., Roberts, N.a., and Borkakoti, N., "Collagenase Inhibitors: Their Design and Potential Therapeutic Use", *Journal of Enzyme Inhibition*, vol. 2 (1987), pp. 1–22.

Schwartz, M.a., Van Wart, H.E., "synthetic Inhibitors of Bacterial and Mammalian Interstitial Collagenases", *Progress in Medicinal chemistry*, vol. 29 (1992), p. 271.

Singh, J., et al. "Relationship Between Structure and Bioavailability in a Series of Hydroxamate Based metalloprotease Inhibitors", *Bioorganic & Medicinal Chemistry Letters*, vol. 5 (1995), pp. 337–342.

Tomczuk, B.E., et al., "Hydroxamate Inhibitors of the Matrix Metallo–Proteinases (MMPs) containing Novel $P_1'$ Heteroatom Based Modifications", *bioorganic & Medicinal chemistry Letters*, vol. 5 (1995), pp. 343–348.

Turbanti, L., et al., "1,2–Cyclomethylenecarboxylic Monoamide Hydroxamic Derivatives. A Novel Class of Non–amino Acid Angiotensin Converting Enzyme Inhibitors", *Journal of Medicinal Chemistry*, vol. 36 (1993), pp. 699–707.

*Primary Examiner*—Floyd D. Higel
*Attorney, Agent, or Firm*—Carl J. Roof; David L. Suter; Jacobus C. Rasser

[57] ABSTRACT

The invention provides compounds of formula

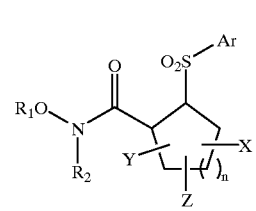

(I)

as described in the claims, or an optical isomer, diastereomer or enantiomer thereof, or a pharmaceutically-acceptable salt, or biohydrolyzable amide, ester, or imide thereof are useful as inhibitors of metalloproteases.

Also disclosed are pharmaceutical compositions and methods of treating diseases, disorders and conditions characterized by metalloprotease activity using these compounds or the pharmaceutical compositions containing them.

31 Claims, No Drawings

SPIROCYCLIC CONTAINING HYDROXAMIC ACIDS USEFUL AS METALLOPROTEASE INHIBITORS

CROSS REFERENCE

This application claims priority under Title 35, United States Code 119(e) from Provisional application Ser. No. 60/024,766, filed Aug. 28, 1996.

TECHNICAL FIELD

This invention is directed to compounds which are useful in treating diseases, disorders and conditions associated with unwanted metalloprotease activity.

BACKGROUND

A number of structurally related metalloproteases [MPs] effect the breakdown of structural proteins. These metalloproteases often act on the intercellular matrix, and thus are involved in tissue breakdown and remodeling. Such proteins are referred to as metalloproteases or MPs. There are several different families of MPs, classified by sequence homology. Several families of known MPs, as well as examples thereof, are disclosed in the art.

These MPs include Matrix-Metallo Proteases [MMPs], zinc metalloproteases, many of the membrane bound metalloproteases, TNF converting enzymes, angiotensin-converting enzymes (ACEs), disintegrins, including ADAMs (See Wolfsberg et al, 131 *J. Cell Bio.* 275–78 October, 1995), and the enkephalinases. Examples of MPs include human skin fibroblast collagenase, human skin fibroblast gelatinase, human sputum collagenase, aggrecanse and gelatinase, and human stromelysin. Collagenase, stromelysin, aggrecanase and related enzymes are thought to be important in mediating the symptomatology of a number of diseases.

Potential therapeutic indications of MP inhibitors have been discussed in the literature. See for example, U.S. Pat. No. 5,506,242 (Ciba Geigy Corp.); U.S. Pat. No. 5.403,952 (Merck & Co.); PCT published application WO 96/06074 (British Bio Tech Ltd); PCT Publication WO 96/00214 (Ciba Geigy); WO 95/35275 (British Bio Tech Ltd); WO 95/35276 (British Bio Tech Ltd); WO 95/33731 (Hoffman-LaRoche); WO 95/33709 (Hoffman-LaRoche); WO 95/32944 (British Bio Tech Ltd); WO 95/26989 (Merck); WO 9529892 (DuPont Merck); WO 95/24921 (Inst. Opthamology); WO 95/23790 (SmithKline Beecham); WO 95/22966 (Sanofi Winthrop); WO 95/19965 (Glycomed); WO 95 19956 (British Bio Tech Ltd); WO 95/19957 (British Bio Tech Ltd); WO 95/19961 (British Bio Tech Ltd) WO 95/13289 (Chiroscience Ltd.); WO 95/12603 (Syntex); WO 95/09633 (Florida State Univ); WO 95/09620 (Florida State Univ.); WO 95/04033 (Celltech); WO 94/25434 (Celltech); WO 94/25435 (Celltech); WO 93/14112 ( Merck); WO 94/0019 (Glaxo); WO 93/21942 (British Bio Tech Ltd); WO 92/22523 (Res. Corp. Tech. Inc.); WO 94/10990 (British Bio Tech Ltd); WO 93/09090 (Yamanouchi); and British patents GB 2282598 (Merck) and GB 2268934 (British Bio Tech Ltd); Published European Patent Applications EP 95/684240 (Hofftnan LaRoche); EP 574758 (Hoffman LaRoche); EP 575844 (Hoffman LaRoche); Published Japanese applications; JP 08053403 (Fujusowa Pharm. Co. Ltd.); JP 7304770 (Kanebo Ltd.); and Bird et al *J. Med Chem* vol. 37, pp. 158–69 (1994). Examples of potential therapeutic uses of MP inhibitors include rheumatoid arthritis (Mullins, D. E., et al., *Biochem. Biophys. Acta.* (1983) 695:117–214); osteoarthritis (Henderson, B., et al., *Drugs of the Future* (1990) 15:495–508); the metastasis of tumor cells (ibid, Broadhurst, M. J., et al., European Patent Application 276,436 (published 1987), Reich, R., et al., 48 *Cancer Res.* 3307–3312 (1988); and various ulcerations or ulcerative conditions of tissue. For example, ulcerative conditions can result in the cornea as the result of alkali burns or as a result of infection by *Pseudomonas aeruginosa,* Acanthamoeba, Herpes simplex and vaccinia viruses.

Other examples of conditions characterized by undesired metalloprotease activity include periodontal disease, epidermolysis bullosa, fever, inflammation and scleritis (Cf DeCicco et al, WO 95 29892 published Nov. 9, 1995).

In view of the involvement of such metalloproteases in a number of disease conditions, attempts have been made to prepare inhibitors to these enzymes. A number of such inhibitors are disclosed in the literature. Examples include U.S. Pat. No. 5,183,900, issued Feb. 2, 1993 to Galardy; U.S. Pat. No. 4,996,358, issued Feb. 26, 1991 to Handa, et al.; U.S. Pat. No. 4,771,038, issued Sep. 13,.1988 to Wolanin, et al.; U.S. Pat. No. 4,743,587, issued May 10, 1988 to Dickens, et al., European Patent Publication Number 575,844, published Dec. 29, 1993 by Broadhurst, et al.; International Patent Publication No. WO 93/09090, published May 13, 1993 by Isomura, et al.; World Patent Publication 92/17460, published Oct. 15, 1992 by Markwell et al.; and European Patent Publication Number 498,665, published Aug. 12, 1992 by Beckett, et al.

Metalloprotease inhibitors are useful in treating diseases caused, at least in part, by breakdown of structural proteins. Though a variety of inhibitors have been prepared, there is a continuing need for potent matrix metalloprotease inhibitors useful in treating such diseases. Applicants have found that, surprisingly, the spirocyclic compounds of the present invention are potent metalloprotease inhibitors.

OBJECTS OF THE INVENTION

Thus it is an object of the present invention to provide compounds useful for the treatment of conditions and diseases which are characterized by unwanted MP activity.

It is also an object of the invention to provide potent inhibitors of metalloproteases.

It is a further object of the invention to provide pharmaceutical compositions comprising such inhibitors.

It is also an object of the invention to provide a method of treatment for metalloprotease related maladies.

SUMMARY OF THE INVENTION

The invention provides compounds which are useful as inhibitors of metalloproteases, and which are effective in treating conditions characterized by excess activity of these enzymes. In particular, the present invention relates to a compound having a structure according to Formula (I)

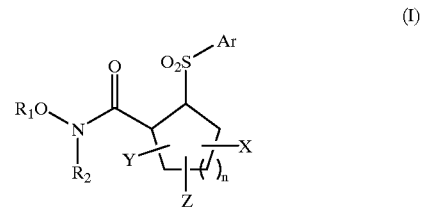

(I)

wherein

Ar is alkyl, heteroalkyl, aryl or heteroaryl, substituted or unsubstituted;

$R_1$ is H;

$R_2$ is hydrogen, alkyl or acyl;

W is nil or one or more lower alkyl moieties, or is an alkylene, arylene or heteroarylene bridge between two adjacent or nonadjacent carbons (thus forming a fused ring);

Y is independently one or more of hydrogen, hydroxy, $SR_3$, $SOR_4$, $SO_2R_5$, alkoxy, amino, wherein amino is of formula $NR_6,R_7$, wherein $R_6$ and $R_7$ are independently chosen from hydrogen, alkyl, heteroalkyl, heteroaryl, aryl, $OR_3$, $SO_2R_8$, $COR_9$, $CSR_{10}$, $PO(R_{11})_2$; and $R_3$ is hydrogen, alkyl, aryl, heteroaryl;

$R_4$ is alkyl, aryl, heteroaryl;

$R_8$ is alkyl, aryl, heteroaryl, heteroalkyl, amino, alkylamino, dialkylamino, arylamino, diarylamino and alkylarylamino;

$R_9$ is hydrogen, alkoxy, aryloxy, heteroaryloxy, alkyl, aryl, heteroaryl, heteroalkyl, amino, alkylamino, dialkylamino, arylamino and alkylarylamino;

$R_{10}$ is alkyl, aryl, heteroaryl, heteroalkyl, amino, alkylamino, dialkylamino, arylamino, diarylamino and alkylarylamino;

$R_{11}$ is alkyl, aryl, heteroaryl, heteroalkyl;

Z is a spiro moiety;

n is 1–3.

This structure also includes an optical isomer, diastereomer or enantiomer for Formula (I), or a pharmaceutically-acceptable salt, or biohydrolyzable amide, ester, or imide thereof.

These compounds have the ability to inhibit at least one mammalian metalloprotease. Accordingly, in other aspects, the invention is directed to pharmaceutical compositions containing the compounds of Formula (I), and to methods of treating diseases characterized by unwanted metalloprotease activity using these compounds or the pharmaceutical compositions containing them.

Metalloproteases which are active at a particularly undesired location (e.g., an organ or certain types of cells) can be targeted by conjugating the compounds of the invention to a targeting ligand specific for a marker at that location such as an antibody or fragment thereof or a receptor ligand. Conjugation methods are known in the art.

The invention is also directed to various other processes which take advantage of the unique properties of these compounds. Thus, in another aspect, the invention is directed to the compounds of Formula (I) conjugated to solid supports. These conjugates can be used as affinity reagents for the purification of a desired metalloprotease.

In another aspect, the invention is directed to the compounds of Formula (I) conjugated to label. As the compounds of the invention bind to at least one metalloprotease, the label can be used to detect the presence of relatively high levels of metalloprotease, preferably a matrix metalloprotease in vivo or in vitro cell culture.

In addition, the compounds of Formula (I) can be conjugated to carriers which permit the use of these compounds in immunization protocols to prepare antibodies specifically immunoreactive with the compounds of the invention. Typical conjugation methods are known in the art. These antibodies are then useful both in therapy and in monitoring the dosage of the inhibitors.

DETAILED DESCRIPTION

The compounds of the present invention are inhibitors of mammalian metalloproteases, preferably a matrix metalloproteases. Preferably, the compounds are those of Formula (I) or a pharmaceutically-acceptable salt, or biohydrolyzable amide, ester, or imide thereof.

Throughout this disclosure, publications and patents are referred to in an effort to fully describe the state of the art. All references cited herein are hereby incorporated by reference.

Definitions and Usage of Terms

The following is a list of definitions for terms used herein.

"Acyl" or "carbonyl" is described as a radical which could be formed by removal of the hydroxy from a carboxylic acid (i.e., R—C(=O)—). Preferred acyl groups include (for example) acetyl, formyl, and propionyl.

"Acyloxy" is an oxy radical having an acyl substituent (i.e., —O—acyl); for example, —O—C(=O)-alkyl.

"Alkoxyacyl" is an acyl radical (—C(=O)—) having an alkoxy substituent (i.e., —O—R), for example, —C(=O)—O—alkyl. This radical can be referred to as an ester.

"Acylamino" is an amino radical having an acyl substituent (i.e., —N-acyl); for example, —NH—C(=O)-alkyl.

"Alkenyl" is an unsubstituted or substituted hydrocarbon chain radical having 2 to 15 carbon atoms; preferably from 2 to 10 carbon atoms; more preferably from 2 to 8; except where indicated. Alkenyl substituents have at least one olefinic double bond (including, for example, vinyl, allyl and butenyl).

"Alkynyl" is an unsubstituted or substituted hydrocarbon chain radical having 2 to 15 carbon atoms; preferably from 2 to 10 carbon atoms; more preferably from 2 to 8; except where indicated. The chain has at least one carbon—carbon triple bond.

"Alkoxy" is an oxygen radical having a hydrocarbon chain substituent, where the hydrocarbon chain is an alkyl or alkenyl (i.e., —O—alkyl or —O—alkenyl). Preferred alkoxy groups include (for example) methoxy, ethoxy, propoxy and allyloxy.

"Alkoxyalkyl" is an unsubstituted or substituted alkyl moiety substituted with an alkoxy moiety (i.e., -alkyl—O—alkyl). Preferred is where the alkyl has 1 to 6 carbon atoms (more preferably 1 to 3 carbon atoms), and the alkyoxy has 1 to 6 carbon atoms (more preferably 1 to 3 carbon atoms).

"Alkyl" is an unsubstituted or substituted saturated hydrocarbon chain radical having 1 to 15 carbon atoms; preferably from 1 to 10 carbon atoms; more preferably 1 to 4; except where indicated. Preferred alkyl groups include (for example) substituted or unsubstituted methyl, ethyl, propyl, isopropyl, and butyl.

As referred to herein, "spiro cycle" or "spiro cyclic" refers to a cyclic moiety sharing a carbon on another ring. Such cyclic moiety may be carbocyclic or heterocyclic in nature. Preferred heteroatoms included in the backbone of the heterocyclic spirocycle include oxygen, nitrogen and sulfur. The spiro cycles may be unsubstituted or substituted. Preferred substituents include oxo, hydroxy, alkyl, cycloalkyl, arylalkyl, alkoxy, amino, heteroalkyl, aryloxy, fused rings (e.g., benzothiole, cycloalkyl, heterocycloalkyl, benzimidizoles, pyridylthiole, etc., which may also be substituted) and the like. In addition, the heteroatom of the heterocycle may be substituted if valence allows. Preferred spirocyclic ring sizes include 3–7 membered rings.

Alkylene refers to an alkyl, alkenyl or alkynyl which is diradical, rather than a radical. "Hetero alkylene" is likewise defined as a (diradical) alkylene having a heteroatom in its chain.

"Alkylamino" is an amino radical having one (secondary amine) or two (tertiary amine) alkyl substituents (i.e., —N—alkyl). For example, methylamino (—NHCH$_3$), dimethylamino (—N(CH$_3$)$_2$), methylethylamino (—N(CH$_3$)CH$_2$CH$_3$).

"Aminoacyl" is acyl radical having an amino substituent (i.e., —C(=O)—N); for example, —C(=O)—NH$_2$. The amino group of the aminoacyl moiety may be unsubstituted (i.e., primary amine) or may be substituted with one (secondary amine) or two (i.e., tertiary amine) alkyl groups.

"Aryl" is an aromatic carbocyclic ring radical. Preferred aryl groups include (for example) phenyl, tolyl, xylyl, cumenyl, naphthyl, biphenyl and fluorenyl. Such groups may be substituted or unsubstituted.

"Arylalkyl" is an alkyl radical substituted with an aryl group. Preferred arylalkyl groups include benzyl, phenylethyl, and phenylpropyl. Such groups may be substituted or unsubstituted. "Arylalkylamino" is an amine radical substituted with an arylalkyl group (e.g., —NH-benzyl). Such groups may be substituted or unsubstituted.

"Arylamino" is an amine radical substituted with an aryl group (i.e., —NH-aryl). Such groups may be substituted or unsubstituted.

"Aryloxy" is an oxygen radical having an aryl substituent (i.e., —O—aryl). Such groups may be substituted or unsubstituted.

"Carbocyclic ring" is an unsubstituted or substituted, saturated, unsaturated or aromatic, hydrocarbon ring radical. Carbocyclic rings are monocyclic or are fused, bridged or spiro polycyclic ring systems. Monocyclic carbocyclic rings generally contain 4 to 9 atoms, preferably 4 to 7 atoms. Polycyclic carbocyclic rings contain 7 to 17 atoms, preferably from 7 to 12 atoms. Preferred polycyclic systems comprise 4-, 5-, 6- or 7-membered rings fused to 5-, 6-, or 7-membered rings.

"Carbocycle-alkyl" is an unsubstituted or substituted alkyl radical substituted with a carbocyclic ring. Unless otherwise specified, the carbocyclic ring is preferably an aryl or cycloalkyl; more preferably an aryl. Preferred carbocycle-alkyl groups include benzyl, phenylethyl and phenylpropyl.

"Carbocycle-heteroalkyl" is an unsubstituted or substituted heteroalkyl radical substituted with a carbocyclic ring. Unless otherwise specified, the carbocyclic ring is preferably an aryl or cycloalkyl; more preferably an aryl. The heteroalkyl is preferably 2-oxa-propyl, 2-oxa-ethyl, 2-thia-propyl, or 2-thia-ethyl.

"Carboxyalkyl" is an unsubstituted or substituted alkyl radical substituted with a carboxy (—(=O)OH) moiety. For example, —CH$_2$—C(=O)OH.

"Cycloalkyl" is a saturated carbocyclic ring radical. Preferred cycloalkyl groups include (for example) cyclopropyl, cyclobutyl and cyclohexyl.

"Cycloheteroalkyl" is a saturated heterocyclic ring. Preferred cycloheteroalkyl groups include (for example) morpholinyl, piperadinyl, piperazinyl, tetrahydrofuryl and hydantoinyl.

"Fused rings" are rings that are superimposed together such that they share two ring atoms. A given ring may be fused to more than one other ring. Fused rings are contemplated heteroaryl, aryl and heterocycle radicals or the like.

"Heterocycle-alkyl" is an alkyl radical substituted with a heterocyclic ring. The heterocyclic ring is preferably a heteroaryl or cycloheteroalkyl; more preferably a heteroaryl. Preferred heterocycle alkyl include C$_1$–C$_4$ alkyl having preferred heteroaryl appended to them. More preferred is, for example, pyridyl alkyl, and the like.

"Heterocycle-heteroalkyl" is an unsubstituted or substituted heteroalkyl radical substituted with a heterocyclic ring. The heterocyclic ring is preferably an aryl or cycloheteroalkyl; more preferably an aryl.

"Heteroatom" is a nitrogen, sulfur or oxygen atom. Groups containing one or more heteroatoms may contain different heteroatoms.

"Heteroalkenyl" is an unsubstituted or substituted unsaturated chain radical having 3 to 8 members comprising carbon atoms and one or two heteroatoms. The chain has at least one carbon-carbon double bond.

"Heteroalkyl" is an unsubstituted or substituted saturated chain radical having 2 to 8 members comprising carbon atoms and one or two heteroatoms.

"Heterocyclic ring" is an unsubstituted or substituted, saturated, unsaturated or aromatic ring radical comprised of carbon atoms and one or more heteroatoms in the ring. Heterocyclic rings are monocyclic or are fused, bridged or spiro polycyclic ring systems. Monocyclic heterocyclic rings contain 3 to 9 atoms, preferably 4 to 7 atoms. Polycyclic rings contain 7 to 17 atoms, preferably from 7 to 13 atoms.

"Heteroaryl" is an aromatic heterocyclic ring, either monocyclic or bicyclic radical. Preferred heteroaryl groups include (for example) thienyl, furyl, pyrrolyl, pyridinyl, pyrazinyl, thiazolyl, pyrimidinyl, quinolinyl, and tetrazolyl, benzo thiazolyl, benzofuryl, indolyl and the like. Such groups may be substituted or unsubstituted.

"Halo", "halogen", or "halide" is a chloro, bromo, fluoro or iodo atom radical. Bromo, chloro and fluoro are preferred halides.

Also, as referred to herein, a "lower" hydrocarbon moiety (e.g., "lower" alkyl) is a hydrocarbon chain comprised of 1 to 6, preferably from 1 to 4, carbon atoms.

A "pharmaceutically-acceptable salt" is a cationic salt formed at any acidic (e.g., carboxyl) group, or an anionic salt formed at any basic (e.g., amino) group. Many such salts are known in the art, as described in World Patent Publication 87/05297, Johnston et al., published Sep. 11, 1987 (incorporated by reference herein). Preferred cationic salts include the alkali metal salts (such as sodium and potassium), and alkaline earth metal salts (such as magnesium and calcium) and organic salts. Preferred anionic salts include the halides (such as chloride salts).

"Biohydrolyzable amides" are amides of the compounds of the invention that do not interfere with the inhibitory activity of the compound, or that are readily converted in vivo by a mammal subject to yield an active inhibitor.

A "biohydrolyzable hydroxy imide" is an imide of a Formula (I) compound that does not interfere with the metalloprotease inhibitory activity of these compounds, or that is readily converted in vivo by a mammal subject to yield an active Formula (I) compound. Such hydroxy imides include those that do not interfere with the biological activity of the Formula (I) compounds.

A "biohydrolyzable ester" refers to an ester of a Formula (I) compound that does not interfere with the metalloprotease inhibitory activity of these compounds or that is readily converted by an animal to yield an active Formula (I) compound.

A "solvate" is a complex formed by the combination of a solute (e.g., a metalloprotease inhibitor) and a solvent (e.g., water). See J. Honig et al., *The Van Nostrand Chemistxs Dictionary* p. 650 (1953). Pharmaceutically-acceptable solvents used according to this invention include those that do not interfere with the biological activity of the metalloprotease inhibitor (e.g., water, ethanol, acetic acid, N,N-dimethylformamide and others known or readily determined by the skilled artisan).

"Optical isomer", "stereoisomer", "diastereomer" as referred to herein have the standard art recognized meanings (Cf., *Hawley's Condensed Chemical Dictionary*, 11th Ed.).

The illustration of specific protected forms and other derivatives of the Formula (I) compounds is not intended to be limiting. The application of other useful protecting groups, salt forms, etc. is within the ability of the skilled artisan.

As defined above and as used herein, substituent groups may themselves be substituted. Such substitution may be with one or more substituents. Such substituents include those listed in C. Hansch and A. Leo, *Substituent Constants for Correlation Analysis in Chemistry and Biology* (1979), incorporated by reference herein. Preferred substituents include (for example) alkyl, alkenyl, alkoxy, hydroxy, oxo, nitro, amino, aminoalkyl (e.g., aminomethyl, etc.), cyano, halo, carboxy, alkoxyaceyl (e.g., carboethoxy, etc.), thiol, aryl, cycloalkyl, heteroaryl, heterocycloalkyl (e.g., piperidinyl, morpholinyl, pyrrolidinyl, etc.), imino, thioxo, hydroxyalkyl, aryloxy, arylalkyl, and combinations thereof.

As used herein "mammalian source" which is capable of catalyzing the breakdown of collagen, gelatin or proteoglycan under suitable assay conditions. Appropriate assay conditions can be found, for example, in U.S. Pat. No. 4,743,587, which references the procedure of Cawston, et al.,*Anal. Biochem.* (1979) 99:340–345, use of a synthetic substrate is described by Weingarten, H., et al., *Biochem. Biolphy. Res. Comm.* (1984) 139:1184–1187. Any standard method for analyzing the breakdown of these structural proteins can, of course, be used. The metalloprotease enzymes referred to herein are all zinc-containing proteases which are similar in structure to, for example, human stromelysin or skin fibroblast collagenase. The ability of candidate compounds to inhibit metalloprotease activity can, of course, be tested in the assays described above. Isolated metalloprotease enzymes can be used to confirm the inhibiting activity of the invention compounds, or crude extracts which contain the range of enzymes capable of tissue breakdown can be used.

Compounds

Compounds of the invention are described in the Summary of the Invention. Preferred compounds of the invention are those in which Z is heterospiroalkylene, preferably having heteroatoms adjacent to the parent ring structure, more preferably such spiroheteroalkylenes have 4 to 5 members. Preferred heteroatoms are divalent.

The invention provides compounds which are useful as inhibitors of metalloproteases, preferably a matrix metalloproteases, and which are effective in treating conditions characterized by excess activity of these enzymes. In particular, the present invention relates to a compound having a structure according to Formula (I)

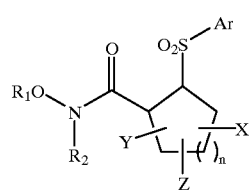

(I)

wherein

Ar is allyl, heteroalkyl, aryl or heteroaryl, substituted or unsubstituted;

$R_1$ is H;

$R_2$ is hydrogen, alkyl or acyl;

W is nil or one or more lower alkyl moieties, or is an alkylene, arylene or heteroarylene bridge between two adjacent or nonadjacent carbons (thus forming a fused ring); Y is independently one or more of hydrogen, hydroxy, $SR_3$, $SOR_4$, $SO_2R_5$, alkoxy, amino, wherein amino is of formula $NR_6R_7$, wherein $R_6$ and $R_7$ are independently chosen from hydrogen, alkyl, heteroalkyl, heteroaryl, aryl, $OR_3$, $SO_2R_8$, $COR_9$, $CSR_{10}$, $PO(R_{11})_2$; and $R_3$ is hydrogen, alkyl, aryl, heteroaryl;

$R_4$ is alkyl, aryl, heteroaryl;

$R_8$ is alkyl, aryl, heteroaryl, heteroalkyl, amino, alkylamino, dialkylamino, arylamino, diarylamino and alkylarylamino;

$R_9$ is hydrogen, alkoxy, aryloxy, heteroaryloxy, alkyl, aryl, heteroaryl, heteroalkyl, amino, alkylamino, dialkylamino, arylamino and alkylarylamino;

$R_{10}$ is alkyl, aryl, heteroaryl, heteroalkyl, amino, alkylamino, dialkylamino, arylamino, diarylamino and alkylarylamino;

$R_{11}$ is alkyl, aryl, heteroaryl, heteroalkyl;

Z is a spiro moiety;

n is 1–3.

This structure also includes an optical isomer, diastereomer or enantiomer for Formula (I), or a pharmaceutically-acceptable salt, or biohydrolyzable ester, amide, or imide thereof.

Compound Preparation

The hydroxamic compounds of Formula (I) can be prepared using a variety of procedures. General schemes include the following.

PREPARATION OF THE Y MOIETY

For the manipulation of Y it is understood that the skilled artisan may choose to prepare Y before, after or concurrent with the preparation of Z, the spiro moiety. For clarity, the W and Z moiety are not shown below. More than one Y and Z may be present in the compounds of formula (I). For compounds where Y is not adjacent to the ring nitrogen, a preferred method of making the compounds is;

SCHEME I

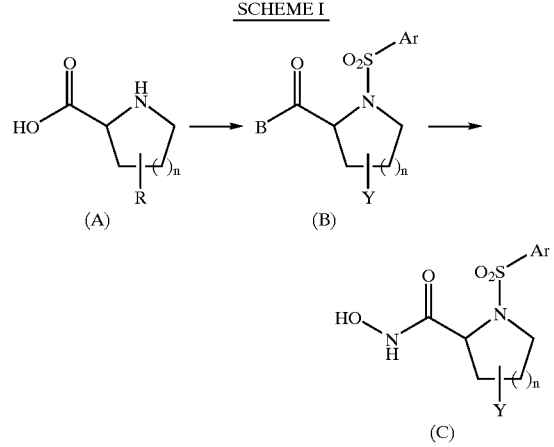

Where R is a derivatizable group or can be manipulated or substituted, such compounds are known or are prepared by known methods. For example, when R is OH, and n is 1, a commercially available hydroxyproline (A) is converted to its analogous sultamester and the hydroxyl is then manipulated to give (B) during this or a subsequent step. Y and Z can be added or altered, followed by treatment with hydroxylamine under basic conditions to give (C).

Where Y is adjacent to the ring nitrogen, a preferred method of preparing compounds of formula I follows. For clarity, the W and Z moieties are not shown;

SCHEME II

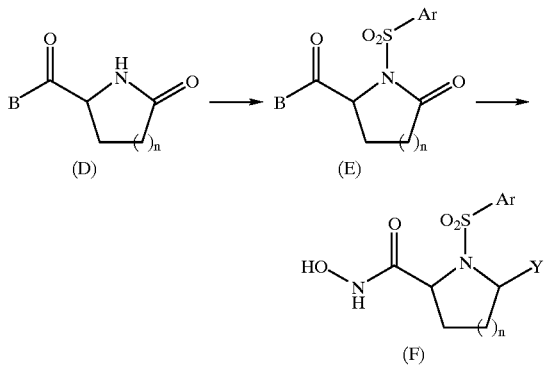

Of course, this route is also a preferred for preparing compounds with Z as heteroalkylene with Z adjacent to the ring nitrogen. The transformations to make the spiro moiety, Z, are known in the art. Of course, for this scheme and others, the skilled artisan will appreciate that the order of the steps may be altered.

Where amide D is known or commercially available, or made by known methods from known materials, and is converted to the corresponding sultamester E using known techniques, much as described in scheme I above, with appropriate manipulation to prepare Y, then elaborating the $R_1d$, a compound of formula I, shown in F. Of course, the steps may be reordered or altered to provide acceptable yield and desired products.

PREPARATION OF THE Z MOIETY

Of course the skilled artisan will recognize that schemes applicable to the preparation of Y may be useful in the preparation of Z as noted above. Other preferred methods are provided for the reader.

Where Z is a ketal or thioketal the compounds of the invention may be prepared by the following method. Again W and Y are not shown for clarity;

SCHEME III

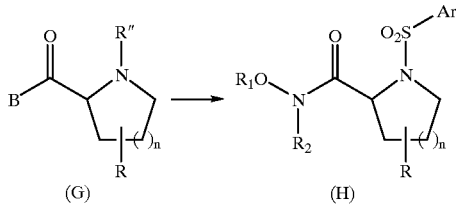

Where R is hydroxy, amino, imino, alkoxy, oxo or any other group that may be manipulated into a carbonyl compound. and R" is hydrogen or any other group that can be displaces in forming the sultamester. The order of elaborating the ketal, $R_1$ or the sultamester may be changed.

A preferred method for making compounds of the invention with Z as a carbocycle or a heterocycle which is not prepared by ketal formation is shown below. The spiro moiety, Z, shown below is depicted as a carbocycle, but heteroatoms may occur interspersed anywhere in the spirocycle. In the scheme below Z is depicted as a carbocyclic spirocycle, but one or more heterotoms may be interspersed in the backbone of the spirocyclic ring. The omission of heteroatoms is meant to aid the reader. It is not meant to limit the claims. Again W and Y are not shown for clarity:

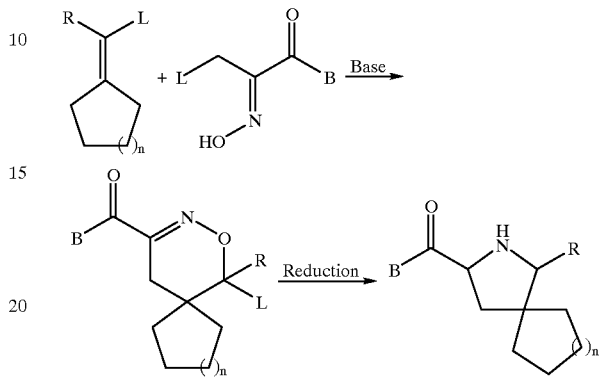

R is any group that may give rise to W or Y. B is a group that can be manipulated into $R_1$ (or in the case of alkoxy is $R_1$). Of course elaborating $R_1$, the sultamester, and the other groups proceeds as previously illustrated.

In any of these methods W may be present in the starting material or a known starting material may have one or more W moieties added using known methodologies.

It is recognized that it is preferable to use a protecting group for any reactive functionality such as a carboxyl, hydroxyl and the like, during the formation of the sulfamester. This is standard practice, well within the normal practice of the skilled artisan.

A preferred method of making the spiro compounds of the invention is via a carbonyl compound, using "protecting group" technology known in the art, such as a thioketol or ketal, and the like. Ketals, acetals and the like are prepared from carbonyl compounds by methods known in the art. Such carbonyl compounds can be made of cyclic hydroxy alkylene amines via oxidation to a ketone, or of lactams, which provide for 2-amino spiro functionality.

A variety of compounds can be generated in a similar fashion, using the guidance of the scheme above.

In the above schemes, where R' is alkoxy or alkylthio, the corresponding hydroxy or thiol compounds are derived from the final compounds by using a standard dealkylating procedure (Bhatt, et al., "Cleavage of Ethers", *Synthesis*, 1983, pp. 249–281).

These steps may be varied to increase yield of desired product. The skilled artisan will also recognize the judicious choice of reactants, solvents, and temperatures is an important component in successful synthesis. While the determination of optimal conditions, etc. is routine, it will be understood that to make a variety of compounds can be generated in a similar fashion, using the guidance of the scheme above.

The starting materials used in preparing the compounds of the invention are known, made by known methods, or are commercially available as a starting material.

It is recognized that the skilled artisan in the art of organic chemistry can readily carry out standard manipulations of organic compounds without further direction; that is, it is well within the scope and practice of the skilled artisan to carry out such manipulations. These include, but are not limited to, reduction of carbonyl compounds to their corresponding alcohols, oxidations of hydroxyls and the like, acylations, aromatic substitutions, both electrophilic and nucleophilic, etherifications, esterification and saponification and the like. Examples of these manipulations are discussed in standard texts such as March, *Advanced Organic Chemistry* (Wiley), Carey and Sundberg, *Advanced Organic Chemistry* (Vol. 2) and Keeting, *Heterocyclic Chemistry* (all 17 volumes).

The skilled artisan will readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. These reactions are found in the literature and are also well within the scope of the skilled artisan. Examples of many of these manipulations can be found for example in T. Greene, *Protecting Groups in Organic Synthesis*. Of course, amino acids used as starting materials with reactive side chains are preferably blocked to prevent undesired side reactions.

The compounds of the invention may have one or more chiral centers. As a result, one may selectively prepare one optical isomer, including diastereomer and enantiomer, over another, for example by chiral starting materials, catalysts or solvents, or may prepare both stereoisomers or both optical isomers, including diastereomers and enantiomers at once (a racemic mixture). Since the compounds of the invention may exist as racemic mixtures, mixtures of optical isomers, including diastereomers and enantiomers, or stereoisomers may be separated using known methods, such as chiral salts, chiral chromatography and the like.

In addition, it is recognized that one optical isomer, including diastereomer and enantiomer, or stereoisomer may have favorable properties over the other. Thus when disclosing and claiming the invention, when one racemic mixture is disclosed, it is clearly contemplated that both optical isomers, including diastereomers and enantiomers, or stereoisomers substantially free of the other are disclosed and claimed as well.

Methods of Use

Metalloproteases (MPs) found in the body operate, in part, by breaking down the extracellular matrix, which comprises extracellular proteins and glycoproteins. These proteins and glycoproteins play an important role in maintaining the size, shape, structure and stability of tissue in the body. Inhibitors of metalloproteases are useful in treating diseases caused, at least in part, by breakdown of such proteins. It is known that MPs are intimately involved in tissue remodeling. As a result of this activity they have been said to be active in many disorders involving either the:

breakdown of tissues; including degenerative diseases, such as arthritis, multiple sclerosis and the like; metastasis or mobility of tissues in the body:

the remodeling of tissues, including fibrotic disease, scarring, benign hyperplasia, and the like.

The compounds of the present invention treat disorders, diseases and/or unwanted conditions which are characterized by unwanted or elevated activity by that class of proteases. For example the compounds can be used to inhibit proteases which destroy structural proteins (i.e. the proteins that maintain tissue stability and structure);

interfere in inter/intracellular signaling, including those implicated in cytokine up-regulation, and/or cytokine processing and/or inflammation, tissue degradation and other maladies [Mohler KM, et al, Nature 370 (1994) 218–220, Gearing A J H, et al, Nature 370 (1994) 555–557 McGeehan G M, et al, Nature 370 (1994) 558–561], and/or facilitate processes which are undesired in the subject being treated, for example, the processes of sperm maturation, egg fertilization and the like.

As used herein, a "MP related disorder" or "a MP related disease" is one that involves unwanted or elevated MP activity in the biological manifestation of the disease or disorder; in the biological cascade leading to the disorder; or as a symptom of the disorder. This "involvement" of the MP includes;

The unwanted or elevated MP activity as a "cause" of the disorder or biological manifestation, whether the activity was elevated genetically, by infection, by autoimmunity, trauma, biomechanical causes, lifestyle [e.g. obesity] or by some other cause;

The MP as part of the observable manifestation of the disease or disorder. That is, the disease or disorder is measurable in terms of the increased MP activity, or from a clinical standpoint, unwanted or elevated MP levels indicate the disease. MPs need not be the "hallmark" of the disease or disorder;

The unwanted or elevated MP activity is part of the biochemical or cellular cascade that results or relates to the disease or disorder. In this respect, inhibition of the MP activity interrupts the cascade, and thus controls the disease.

Advantageously, many MPs are not distributed evenly throughout the body. Thus the distribution of MPs expressed in various tissues are often specific to those tissues. For example, the distribution of metalloproteases implicated in the breakdown of tissues in the joints, is not the same as the distribution of metalloproteases found in other tissues. Thus, though not essential for activity or efficacy, certain disorders preferably are treated with compounds that act on specific MPs found in the affected tissues or regions of the body. For example, a compound which displays a higher degree of affinity and inhibition for a MP found in the joints (e.g. chondrocytes) would be preferred for treatment of disease found there than other compounds which are less specific.

In addition, certain inhibitors are more bioavailable to certain tissues than others, and this judicious choice of inhibitor, with the selectivity described above provides for specific treatment of the disorder, disease or unwanted condition. For example, compounds of this invention vary in their ability to penetrate into the central nervous system. Thus compounds may be selected to produce effects mediated through MPs found specifically outside the central nervous system.

Determination of the specificity of a MP inhibitor of a certain MP is within the skill of the artisan in that field. Appropriate assay conditions can be found in the literature. Specifically assays are known for stromelysin and collagenase. For example, U.S. Pat. No. 4,743,587 references the procedure of Cawston, et al., *Anal Biochem* (1979) 99:340–345. The use of a synthetic substrate in an assay is described by Weingarten, H., et al., *Biochem Biophy Res Comm* (1984) 139:1184–1187. Any standard method for analyzing the breakdown of structural proteins by MPs can, of course, be used. The ability of compounds of the invention to inhibit metalloprotease activity can, of course, be tested in the assays found in the literature, or variations thereof. Isolated metalloprotease enzymes can be used to confirm the inhibiting activity of the invention compounds, or crude extracts which contain the range of enzymes capable of tissue breakdown can be used.

As a result of the MP inhibitory effect of the compounds of the invention, the compounds of the invention are also useful in treating the following disorders by virtue of their metalloprotease activity.

The compounds of this invention are also useful for the prophylactic or acute treatment. They are administered in any way the skilled artisan in the fields of medicine or pharmacology would desire. It is immediately apparent to the skilled artisan that preferred routes of administration will depend upon the disease state being treated, and the dosage form chosen. Preferred routes for systemic administration include administration perorally or parenterally.

However, the skilled artisan will readily appreciate the advantage of administering the MP inhibitor directly to the affected area for many disorders. For example, it may be advantageous to administer MP inhibitors directly to the area of the disease or condition as in area affected by surgical trauma (e. g., angioplasty), area affected by scarring or burn (e.g., topical to the skin), Because the remodeling of bone involves MPs, the compounds of the invention are useful in preventing prosthesis loosening. It is known in the art that over time prostheses loosen, become painful, and may result in further bone injury, thus demanding replacement. The need for replacement of such prostheses includes those such as in, joint replacements (for example hip, knee and shoulder replacements), dental prosthesis, including dentures, bridges and prosthesis secured to the maxilla and/or mandible.

MPs are also active in remodeling of the cardiovascular system (for example, in congestive heart failure). It has been suggested that one of the reasons angioplasty has a higher than expected long term failure rate (reclosure over time) is that MP activity is not desired or is elevated in response to what may be recognized by the body as "injury" to the basement membrane of the vessel. Thus regulation of MP activity in indications such as dilated cardiomyopathy, congestive heart failure, atherosclerosis, plaque rupture, reperfusion injury, ischemia, chronic obstructive pulmonary disease, angioplasty restenosis and aortic aneurysm may increase long term success of any other treatment, or may be a treatment in itself.

In skin care, MPs are implicated in the remodeling or "turnover" of skin. As a result, the regulation of MPs improves treatment of skin conditions including but not limited to, wrinkle repair, regulation and prevention and repair of ultraviolet induced skin damage. Such a treatment includes prophylactic treatment or treatment before the physiological manifestations are obvious. For example, the MP may be applied as a pre-exposure treatment to prevent ultraviolet damage and/or during or after exposure to prevent or minimize post-exposure damage. In addition, MPs are implicated in skin disorders and diseases related to abnormal tissues that result from abnormal turnover, which includes metalloprotease activity, such as epidermolysis bullosa, psoriasis, scleroderma and atopic dermatitis. The compounds of the invention are also useful for treating the consequences of "normal" injury to the skin including scarring or "contraction" of tissue, for example, following burns. MP inhibition is also useful in surgical procedures involving the skin for prevention of scarring, and promotion of normal tissue growth including in such applications as limb reattachment and refractory surgery (whether by laser or incision).

In addition, MPs are related to disorders involving irregular remodeling of other tissues, such as bone, for example, in otosclerosis and/or osteoporosis, or for specific organs, such as in liver cirrhosis and fibrotic lung disease. Similarly in diseases such as multiple sclerosis, MPs may be involved in the irregular modeling of blood brain barrier and/or myelin sheaths of nervous tissue. Thus regulating MP activity may be used as a strategy in treating, preventing, and controlling such diseases.

MPs are also thought to be involved in many infections, including cytomegalovirus; [CMV] retinitis; HIV, and the resulting syndrome, AIDS.

MPs may also be involved in extra vascularization where surrounding tissue needs to be broken down to allow new blood vessels such as in angiofibroma and hemangioma.

Since MPs break down the extracellular matrix, it is contemplated that inhibitors of these enzymes can be used as birth control agents, for example in preventing ovulation, in preventing penetration of the sperm into and through the extracellular milieu of the ovum, implantation of the fertilized ovum and in preventing sperm maturation.

In addition they are also contemplated to be useful in preventing or stopping premature labor and delivery.

Since MPs are implicated in the inflammatory response, and in the processing of cytokines the compounds are also useful as anti-inflammatories, for use in disease where inflammation is prevalent including, inflammatory bowel disease, Crohn's disease, ulcerative colitis, pancreatitis, diverticulitis, asthma or related lung disease, rheumatoid aritis, gout and Reiter's Syndrome.

Where autoimmunity is the cause of the disorder, the immune response often triggers MP and cytokine activity. Regulation of MPs in treating such autoimmune disorders is a useful treatment strategy. Thus MP inhibitors can be used for treating disorders including, lupus erytnatosis, ankylosing spondylitis, and autoimmune keratitis. Sometimes the side effects of autoimmune therapy result in exacerbation of other conditions mediated by MPs, here MP inhibitor therapy is effective as well, for example, in autoimmune-therapy-induced fibrosis.

In addition, other fibrotic diseases lend themselves to this type of therapy, including pulmonary disease, bronchitis, emphysema, cystic fibrosis, acute respiratory distress syndrome (especially the acute phase response).

Where MPs are implicated in the undesired breakdown of tissue by exogenous agents, these can be treated with MP inhibitors. For example, they are effective as rattle snake bite antidote, as anti-vessicants, in treating allergic inflammation, septicemia and shock. In addition, they are useful as antiparasitics (e.g., in malaria) and antiinfectives. For example, they are thought to be useful in treating or preventing viral infection, including infection which would result in herpes, "cold" (e.g., rhinoviral infection), meningitis, hepatitis, HIV infection and AIDS.

MP inhibitors are also thought to be useful in treating Alzheimer's disease, amyotrophic lateral sclerosis (ALS), muscular dystrophy, complications resulting from or arising out of diabetes, especially those involving loss of tissue viability, coagulation, Graft vs. Host disease, leukemia, cachexia, anorexia, proteinuria, and perhaps regulation of hair growth.

For some diseases, conditions or disorders MP inhibition is contemplated to be a preferred method of treatment. Such diseases, conditions or disorders include, arthritis (including osteoarthritis and rheumitoid arthritis), cancer (especially the prevention or arrest of tumor growth and metastasis), ocular disorders (especially corneal ulceration, lack of corneal healing, macular degeneration, and pterygium), and gum disease (especially periodontal disease, and gingivitis)

Compounds preferred for, but not limited to, the treatment of arthritis (including osteoarthritis and rheumatoid arthritis) are those compounds that are selective for the metalloproteases and the disintegrin metalloproteases.

Compounds preferred for, but not limited to, the treatment of cancer (especially the prevention or arrest of tumor growth and metastasis) are those compounds that preferentially inhibit gelatinases or type IV collagenases.

Compounds preferred for, but not limited to, the treatment of ocular disorders (especially corneal ulceration, lack of corneal healing, macular degeneration, and pterygium) are those compounds that broadly inhibit metalloproteases. Preferably these compounds are administered topically, more preferably as a drop or gel.

Compounds preferred for, but not limited to, the treatment of gum disease (especially periodontal disease, and gingivitis) are those compounds that preferentially inhibit collagenases.

Compositions

The compositions of the invention comprise:

(a) a safe and effective amount of a compound of Formula (I); and (b) a pharrnaceutically-acceptable carrier.

As discussed above, numerous diseases are known to be mediated by excess or undesired metalloprotease activity. These include tumor metastasis, osteoarthritis, rheumatoid arthritis, skin inflammation, ulcerations, particularly of the cornea, reaction to infection, periodontitis and the like. Thus, the compounds of the invention are useful in therapy with regard to conditions involving this unwanted activity.

The invention compounds can therefore be formulated into pharmaceutical compositions for use in treatment or prophylaxis of these conditions. Standard pharmaceutical formulation techniques are used, such as those disclosed in *Remington's Pharmaceutical Sciences,* Mack Publishing Company, Easton, Pa., latest edition.

A "safe and effective amount" of a Formula (I) compound is an amount that is effective, to inhibit metalloproteases at the site(s) of activity, in a mammal subject, without undue adverse side effects (such as toxicity, irritation, or allergic response), commensurate with a reasonable benefit/risk ratio when used in the manner of this invention. The specific "safe and effective amount" will, obviously, vary with such factors as the particular condition being treated, the physical condition of the patient, the duration of treatment, the nature of concurrent therapy (if any), the specific dosage form to be used, the carrier employed, the solubility of the Formula (I) compound therein, and the dosage regimen desired for the composition.

In addition to the subject compound, the compositions of the subject invention contain a pharmaceutically-acceptable carrier. The term "pharmaceutically-acceptable carrier", as used herein, means one or more compatible solid or liquid filler diluents or encapsulating substances which are suitable for administration to a mammal. The term "compatible", as used herein, means that the components of the composition are capable of being commingled with the subject compound, and with each other, in a manner such that there is no interaction which would substantially reduce the pharmaceutical efficacy of the composition under ordinary use situations. Pharmaceutically-acceptable carriers must, of course, be of sufficiently high purity and sufficiently low toxicity to render them suitable for administration to the animal, preferably mammal being treated.

Some examples of substances which can serve as pharmaceutically-acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the TWEENS"; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject compound is basically determined by the way the compound is to be administered.

If the subject compound is to be injected, the preferred pharmaceutically-acceptable carrier is sterile, physiological saline, with blood-compatible suspending agent, the pH of which has been adjusted to about 7.4.

In particular, pharmaceutically-acceptable carriers for systemic administration include sugars, starches, cellulose and its derivatives, malt, gelatin, talc, calcium sulfate, vegetable oils, synthetic oils, polyols, alginic acid, phosphate buffer solutions, emulsifiers, isotonic saline, and pyrogen-free water. Preferred carriers for parenteral administration include propylene glycol, ethyl oleate, pyrrolidone, ethanol, and sesame oil. Preferably, the pharmaceutically-acceptable carrier, in compositions for parenteral administration, comprises at least about 90% by weight of the total composition.

The compositions of this invention are preferably provided in unit dosage form. As used herein, a "unit dosage form" is a composition of this invention containing an amount of a Formula (I) compound that is suitable for administration to a animal, preferably mammal subject, in a single dose, according to good medical practice. These compositions preferably contain from about 5 mg (milligrams) to about 1000 mg, more preferably from about 10 mg to about 500 mg, more preferably from about 10 mg to about 300 mg, of a Formula (I) compound.

The compositions of this invention may be in any of a variety of forms, suitable (for example) for oral, rectal, topical, nasal, ocular or parenteral administration. Depending upon the particular route of administration desired, a variety of pharmaceutically-acceptable carriers well-known in the art may be used. These include solid or liquid fillers, diluents, hydrotropes, surface-active agents, and encapsulating substances. Optional pharrnaceutically-active materials may be included, which do not substantially interfere with the inhibitory activity of the Formula (I) compound. The amount of carrier employed in conjunction with the Formula (I) compound is sufficient to provide a practical quantity of material for administration per unit dose of the Formula (I) compound. Techniques and compositions for making dosage forms useful in the methods of this invention are described in the following references, all incorporated by reference herein: *Modern Pharmaceutics,* Chapters 9 and 10 (Banker & Rhodes, editors, 1979); Lieberman et al., *Pharmaceutical Dosage Forms: Tablets* (1981); and Ansel, *Introduction to Pharmaceutical Dosage Forms* 2d Edition (1976).

In addition to the subject compound, the compositions of the subject invention contain a pharmaceutically-acceptable carrier. The term "pharmaceutically-acceptable carrier", as used herein, means one or more compatible solid or liquid filler diluents or encapsulating substances which are suitable for administration to a animal, preferably mammal. The term "compatible", as used herein, means that the components of the composition are capable of being commingled with the subject compound, and with each other, in a manner such that there is no interaction which would substantially reduce the pharmaceutical efficacy of the composition under ordinary use situations. Pharmaceutically-acceptable carriers must, of course, be of sufficiently high purity and sufficiently low toxicity to render them suitable for administration to the animal, preferably mammal being treated.

Some examples of substances which can serve as pharmaceutically-acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; vegetable oils, such as peanut oil, cottonseed oil, sesame oil, olive oil, corn oil and oil of theobroma; polyols such as propylene glycol, glycerine, sorbitol, mannitol, and polyethylene glycol; alginic acid; emulsifiers, such as the TWEENS; wetting agents, such sodium lauryl sulfate; coloring agents; flavoring agents; tableting agents, stabilizers; antioxidants; preservatives; pyrogen-free water; isotonic saline; and phosphate buffer solutions.

The choice of a pharmaceutically-acceptable carrier to be used in conjunction with the subject compound is basically determined by the way the compound is to be administered.

If the subject compound is to be injected, the preferred pharmaceutically-acceptable carrier sterile, physiological saline, with blood-compatible suspending agent, the pH of which has been adjusted to about 7.4.

Various oral dosage forms can be used, including such solid forms as tablets, capsules, granules and bulk powders. These oral forms comprise a safe and effective amount, usually at last about 5%, and preferably from about 25% to about 50%, of the Formula (I) compound. Tablets can be compressed, tablet triturates, enteric-coated, sugar-coated, film-coated, or multiple-compressed, containing suitable binders, lubricants, diluents, disintegrating agents, coloring agents, flavoring agents, flow-inducing agents, and melting agents. Liquid oral dosage forms include aqueous solutions, emulsions, suspensions, solutions and/or suspensions reconstituted from non-effervescent granules, and effervescent preparations reconstituted from effervescent granules, containing suitable solvents, preservatives, emulsifying agents, suspending agents, diluents, sweeteners, melting agents, coloring agents and flavoring agents.

The pharmaceutically-acceptable carrier suitable for the preparation of unit dosage forms for peroral administration are well-known in the art. Tablets typically comprise conventional pharmaceutically-compatible adjuvants as inert diluents, such as calcium carbonate, sodium carbonate, mannitol, lactose and cellulose; binders such as starch, gelatin and sucrose; disintegrants such as starch, alginic acid and croscarmelose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, are useful adjuvants for chewable tablets. Capsules typically comprise one or more solid diluents disclosed above. The selection of carrier components depends on secondary considerations like taste, cost, and shelf stability, which are not critical for the purposes of the subject invention, and can be readily made by a person skilled in the art.

Peroral compositions also include liquid solutions, emulsions, suspensions, and the like. The pharmaceutically-acceptable carriers suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, AVICEL RC-591, tragacanth and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Such compositions may also be coated by conventional methods, typically with pH or time-dependent coatings, such that the subject compound is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methyl cellulose phthalate, ethyl cellulose, Eudragit" coatings, waxes and shellac.

Compositions of the subject invention may optionally include other drug actives.

Other compositions useful for attaining systemic delivery of the subject compounds include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

The compositions of this invention can also be administered topically to a subject, e.g., by the direct laying on or spreading of the composition on the epidermal or epithelial tissue of the subject, or transdermally via a "patch". Such compositions include, for example, lotions, creams, solutions, gels and solids. These topical compositions preferably comprise a safe and effective amount, usually at least about 0.1%, and preferably from about 1% to about 5%, of the Formula (I) compound. Suitable carriers for topical administration preferably remain in place on the skin as a continuous film, and resist being removed by perspiration or immersion in water. Generally, the carrier is organic in nature and capable of having dispersed or dissolved therein the Formula (I) compound. The carrier may include pharmaceutically-acceptable emolients, emulsifiers, thickening agents, solvents and the like.

Methods of Administration

This invention also provides methods of treating or preventing disorders associated with excess or undesired metalloprotease activity in an animal, preferably mammal subject, by administering a safe and effective amount of a Formula (I) compound to said subject. As used herein, a "disorder associated with excess or undesired metalloprotease activity" is any disorder characterized by degradation of proteins. The methods of the invention are useful in treating disorders such as (for example) osteoarthritis, periodontitis, corneal ulceration, tumor invasion, and rheumatoid arthritis.

The Formula (I) compounds and compositions of this invention can be administered topically or systemically.

Systemic application includes any method of introducing Formula (I) compound into the tissues of the body, e.g., intra-articular (especially in treatment of rheumatoid arthritis), intrathecal, epidural, intramuscular, transdermal, intravenous, intraperitoneal, subcutaneous, sublingual, rectal, and oral administration. The Formula (I) compounds of the present invention are preferably administered orally.

The specific dosage of inhibitor to be administered, as well as the duration of treatment, and whether the treatment is topical or systemic are interdependent. The dosage and treatment regimen will also depend upon such factors as the specific Formula (I) compound used, the treatment indication, the ability of the Formula (I) compound to reach minimum inhibitory concentrations at the site of the metalloprotease to be inhibited, the personal attributes of the subject (such as weight), compliance with the treatment regimen, and the presence and severity of any side effects of the treatment.

Typically, for a human adult (weighing approximately 70 kilograms), from about 5 mg to about 3000 mg, more preferably from about 5 mg to about 1000 mg, more preferably from about 10 mg to about 100 mg, of Formula (I) compound are administered per day for systemic administration. It is understood that these dosage ranges are by way of example only, and that daily administration can be adjusted depending on the factors listed above.

A preferred method of administration for treatment of rheumatoid arthritis is oral or parenterally via intra-articular injection. As is known and practiced in the art, all formulations for parenteral administration must be sterile. For mammals, especially humans, (assuming an approximate body weight of 70 kilograms) individual doses of from about 10 mg to about 1000 mg are preferred.

A preferred method of systemic administration is oral. Individual doses of from about 10 mg to about 1000 mg, preferably from about 10 mg to about 300 mg are preferred.

Topical administration can be used to deliver the Formula (I) compound systemically, or to treat a subject locally. The amounts of Formula (I) compound to be topically administered depends upon such factors as skin sensitivity, type and location of the tissue to be treated, the composition and carrier (if any) to be administered, the particular Formula (I) compound to be administered, as well as the particular disorder to be treated and the extent to which systemic (as distinguished from local) effects are desired.

The inhibitors of the invention can be targeted to specific locations where the metalloprotease is accumulated by using targeting ligands. For example, to focus the inhibitors to metalloprotease contained in a tumor, the inhibitor is conjugated to an antibody or fragment thereof which is immunoreactive with a tumor marker as is generally understood in the preparation of immunotoxins in general. The targeting ligand can also be a ligand suitable for a receptor which is present on the tumor. Any targeting ligand which specifically reacts with a marker for the intended target tissue can be used. Methods for coupling the invention compound to the targeting ligand are well known and are similar to those described below for coupling to carrier. The conjugates are formulated and administered as described above.

For localized conditions, topical administration is preferred. For example, to treat ulcerated cornea, direct application to the affected eye may employ a formulation as eyedrops or aerosol. For corneal treatment, the compounds of the invention can also be formulated as gels, drops or ointments, or can be incorporated into collagen or a hydrophilic polymer shield. The materials can also be inserted as a contact lens or reservoir or as a subconjunctival formulation. For treatment of skin inflammation, the compound is applied locally and topically, in a gel, paste, salve or ointment. The mode of treatment thus reflects the nature of the condition and suitable formulations for any selected route are available in the art.

In all of the foregoing, of course, the compounds of the invention can be administered alone or as mixtures, and the compositions may further include additional drugs or excipients as appropriate for the indication.

Some of the compounds of the invention also inhibit bacterial metalloproteases although generally at a lower level than that exhibited with respect to mammalian metalloproteases. Some bacterial metalloproteases seem to be less dependent on the stereochemistry of the inhibitor, whereas substantial differences are found between diastereomers in their ability to inactivate the mammalian proteases. Thus, this pattern of activity can be used to distinguish between the mammalian and bacterial enzymes.

Preparation and Use of Antibodies

The invention compounds can also be utilized in immunization protocols to obtain antisera immunospecific for the invention compounds. As the invention compounds are relatively small, they are advantageously coupled to antigenically neutral carriers such as the conventionally used keyhole limpet hemocyanin (KLH) or serum albumin carriers. For those invention compounds having a carboxyl functionality, coupling to carrier can be done by methods generally known in the art. For example, the carboxyl residue can be reduced to an aldehyde and coupled to carrier through reaction with sidechain amino groups in protein-based carriers, optionally followed by reduction of imino linkage formed. The carboxyl residue can also be reacted with sidechain amino groups using condensing agents such as dicyclohexyl carbodiimide or other carbodiimide dehydrating agents.

Linker compounds can also be used to effect the coupling; both homobifunctional and heterobifunctional linkers are available from Pierce Chemical Company, Rockford, Ill. The resulting immunogenic complex can then be injected into suitable mammalian subjects such as mice, rabbits, and the like. Suitable protocols involve repeated injection of the immunogen in the presence of adjuvants according to a schedule which boosts production of antibodies in the serum. The titers of the immune serum can readily be measured using immunoassay procedures, now standard in the art, employing the invention compounds as antigens.

The antisera obtained can be used directly or monoclonal antibodies may be obtained by harvesting the peripheral blood lymphocytes or the spleen of the immunized animal and immortalizing the antibody-producing cells, followed by identifying the suitable antibody producers using standard immunoassay techniques.

The polyclonal or monoclonal preparations are then useful in monitoring therapy or prophylaxis regimens involving the compounds of the invention. Suitable samples such as those derived from blood, serum, urine, or saliva can be tested for the presence of the administered inhibitor at various times during the treatment protocol using standard immunoassay techniques which employ the antibody preparations of the invention.

The invention compounds can also be coupled to labels such as scintigraphic labels, e.g., technetium 99 or I-131, using standard coupling methods. The labeled compounds are administered to subjects to determine the locations of excess amounts of one or more metalloproteases in vivo. The ability of the inhibitors to selectively bind metalloprotease is thus taken advantage of to map the distribution of these enzymes in situ. The techniques can also be employed in histological procedures and the labeled invention compounds can be used in competitive immunoassays.

The following non-limiting examples illustrate the compounds, compositions, and uses of the present invention.

EXAMPLES

Compounds are analyzed using $^1$H and $^{13}$C NMR, Elemental analysis, mass spectra and/or IR spectra, as appropriate.

Typically inert solvents are used, preferably in dried form. For example, tetrahydrofuran (THF) is distilled from sodium and benzophenone, diisopropylamine is distilled from calcium hydride and all other solvents are purchased as the appropriate grade. Chromatography is performed on silica gel (70–230 mesh; Aldrich) or (230–400 mesh; Merck) as appropriate. Thin layer chromatography analysis (TLC) is performed on glass mounted silica gel plates (200–300 mesh; Baker) and visualized with UV or 5% phosphomolybdic acid in EtOH.

EXAMPLE 1

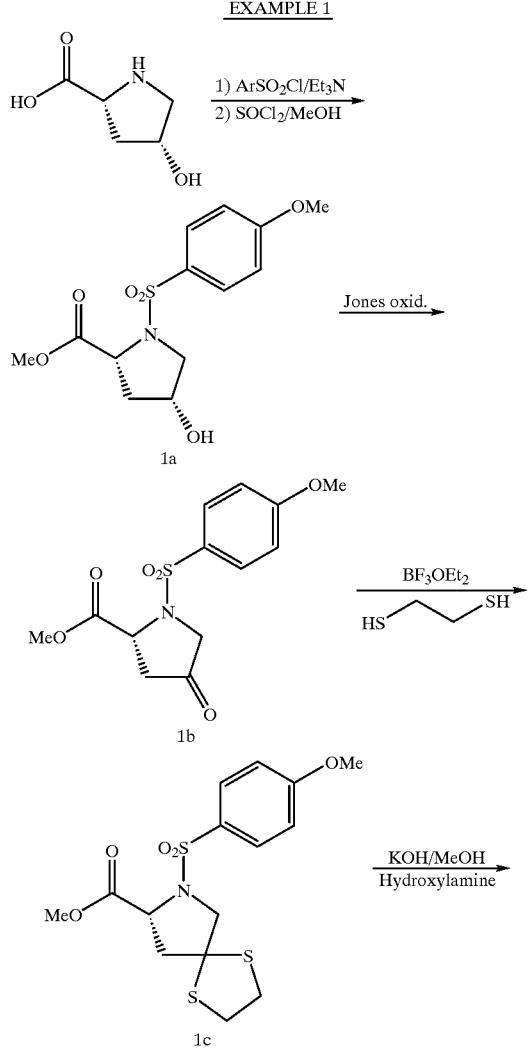

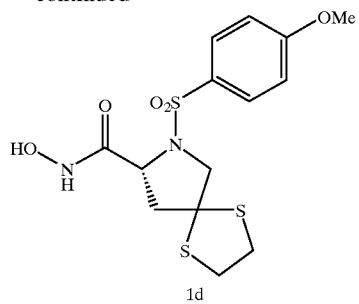

1a. Methyl 1N-(4-methoxyphenylsulfonyl)-4(R)-hydroxypyrrolidine-2(R)carboxylate:

cis-Hydroxy-D-proline (50 g, 0.38 mole) is dissolved in water : dioxane (1:1, 300 mL) with triethylamine (135 mL, 0.96 mole). The 4-methoxyphenylsulfonyl chloride (87 g, 0.42 mole) is added along with 2,6-dimethylaminopyridine (4.6 g, 0.038 mole) and the mixture is stirred 14 hr. at room temperature. The mixture is then concentrated and diluted with EtOAc. The layers are separated and the organic layer is washed twice with 1 N HCl, once with brine, dried over MgSO$_4$, filtered and evaporated to give 83 g of solid material which is dissolved in MeOH (500 mL). Thionyl chloride (50 mL) is added dropwise and the resulting mixture is stirred for 14 hr. The mixture is then evaporated to dryness and triturated with CHCl$_3$ to give a white solid which is sufficiently pure to carry forward without purification.

1b. Intermediate A Methyl 1N-(4methoxyphenylsulfonyl) 4oxo-pyrrolidine2(R)-carboxylate:

A 8 M batch of Jones reagent is prepared. The alcohol 1a (10.0 g, 31.7 mmol) is dissolved in 175 mL of acetone and cooled to 0° C. Jones reagent is added until the solution remains an orange color and the mixture is stirred at room temperature for 14 hr. Isopropanol is added to the solution to quench the excess chromium reagent and the resulting solid is filtered through celite. The filtrate is concentrated under reduced pressure and the residue is dissolved in methylene chloride and washed with water. The resulting solution is dried over magnesium sulfate, and concentrated under reduced pressure. Purification of the product by chromatography on silica gel using EtOAc: hexane (1:1) provided the desired ketone. MS (ESI): 374 (M$^+$+H).

1c. Methyl 7N-(4-methoxyphenylsulfonyl)-1,4-dithia-7-azaspiro[4.4]nonane-8(R)-carboxylate:

The ketone 1b (1.3 g, 4.15 mmol) is dissolved in 30 mL of anhydrous dichloromethane and then 1,2 ethane dithiol (0.800 mL, 8.30 mmol) and borane trifluoride etherate (0.20 mL, 1.66 mmol) are added. The mixture is stirred at room temperature overnight. The solution is made basic by the addition of 1 N sodium hydroxide and then the mixture is extracted three times with EtOAc. The organic layers are washed with water and ammonium chloride, dried over magnesium sulfate, filtered and evaporated to give the title compound. MS (FSf): 390 (M$^+$+H), 407 (M$^+$+NH$_4$).

1d. N-Hydroxy-7N-(4-methoxyphenylsulfonyl)-1,4-dithia-7-azaspiro[4.4]nonane-8(R)-carboxamide:

A 1.76 M solution of potassium hydroxylamine in methanol is prepared. The 1.76 M solution (1.46 mL, 2.57 mmol) is added directly to the methyl ester 1c (0.100 g, 0.257 mmol) and the reaction mixture is stirred overnight. The solution is acidified with 1 N HCl, then the mixture is extracted three times with ethyl acetate, dried with magne sium sulfate, filtered and evaporated. The product is purified by chromatography on silica gel using ethyl acetate : hexane : formic acid (1:1:0.1) to give the title compound. MS (SI): 391 (M$^+$+H), 408 (M$^+$+NH$_4$).

on silica gel using ethyl acetate/hexane/formic acid (1/1/0.1) to give the pure compound. MS (ESI): 439 (M$^+$+H).

EXAMPLE 2

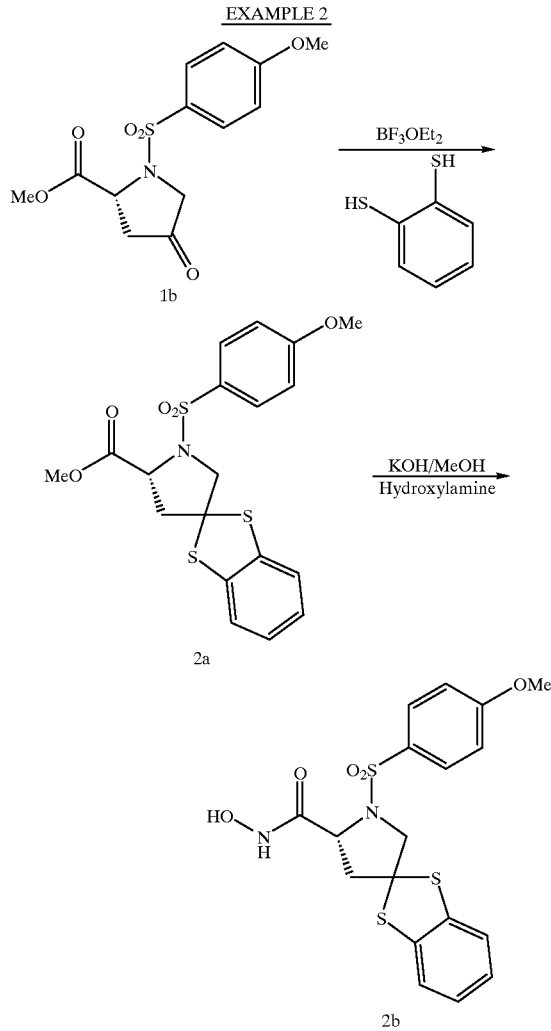

EXAMPLE 3

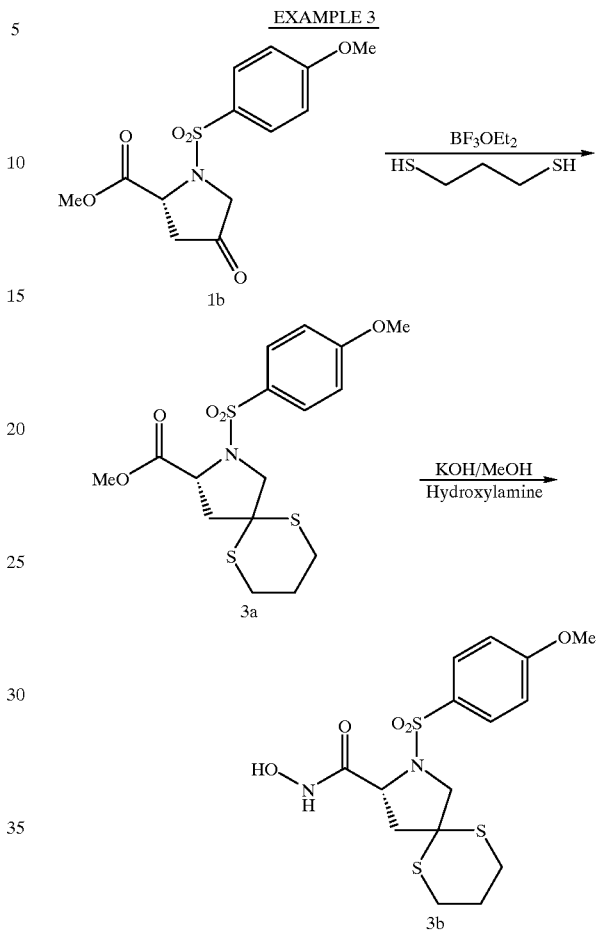

2a. Methyl 1'N-(4methoxyphenylsulfonyl)-spiro[1,3-benzothiole-2,4'-pyrrolidine]-2'(R)-carboxylate:

The ketone 1b (0.5 g, 1.59 mmol) is dissolved in 10 mL of anhydrous dichloromethane and then 1,2 benzenedithiol (0.450 g, 3.19 mmol) and borane trifluoride etherate (0.07 mL, 0.63 mmol) are added. The mixture is stirred at room temperature overnight. The solution is made basic by the addition of 1 N sodium hydroxide and then the mixture is extracted three times with ethyl acetate. The organic layers are washed with water and ammonium chloride, dried over 30 magnesium sulfate and evaporated under reduced pressure to provide a solid. MS (ESI): 438 (M$^+$+H).

2b. N-hydroxy-1'N-(4-methoxyphenylsulfonyl)-spiro [1,3-benzothiole-2,4'-pyrrolidine]-2'(R)-carboxamide:

A 1.76 M solution of potassium hydroxylamine in methanol is prepared. The 1.76 M solution (7.3 mL, 13.0 mmol) is added directly to the methyl ester 2a (0.590 g, 1.3 mmol) and the reaction mixture is stirred overnight. 1 N HCl is added to the solution to acidify it, and then the solution is extracted three times with ethyl acetate, dried with magnesium sulfate and evaporated under reduced pressure. Purification of the product is accomplished by chromatography 3a. Methyl 8N-(4-methoxyphenylsulfonyl)-1,5-Dithia-8-azaspiro[4.5]nonane-9(R)-carboxylate:

The ketone 1b (1.5 g, 4.79 mmol) is dissolved in 30 mL of anhydrous dichloromethane and then the 1,3- propanedithiol (1.20 mL, 11.9 mmol) and borane trifluoride etherate (0.24 mL, 1.91 mmol) are added. The mixture is stirred at room temperature overnight. The solution is made basic by the addition of 1 N sodium hydroxide and then the mixture is extracted three times with ethyl acetate. The organic layers are washed with water and ammonium chloride, dried over magnesium sulfate and evaporated under reduced pressure to give a solid. MS (ESI): 403 (M$^+$+H), 420 (M$^+$+NH$_4$).

3b. N-Hydroxy-SN-(4-methoxyphenylsulfonyl)-1,5-Dithia-8-azaspiro[45]nonane-9(R)-carboxylate:

A 1.76 M solution of potassium hydroxylamine in methanol is prepared. The 1.76 M solution (1.4 mL, 2.48 mmol) is added directly to the methyl ester 3a (0.100 g, 0.248 mmol) and the reaction mixture is stirred overnight. 1 N HCl is added to the solution to acidify it, then the resulting mixture is extracted three times with ethyl acetate, dried with magnesium sulfate and evaporated under reduced pressure.. Purification of the product is accomplished by chromatography on silica gel using ethyl acetate/hexane/formic acid (1/1/0.1) to give the pure compound. MS (ESI): 404 (M$^+$+H), 421 (M$^+$+NH$_4$).

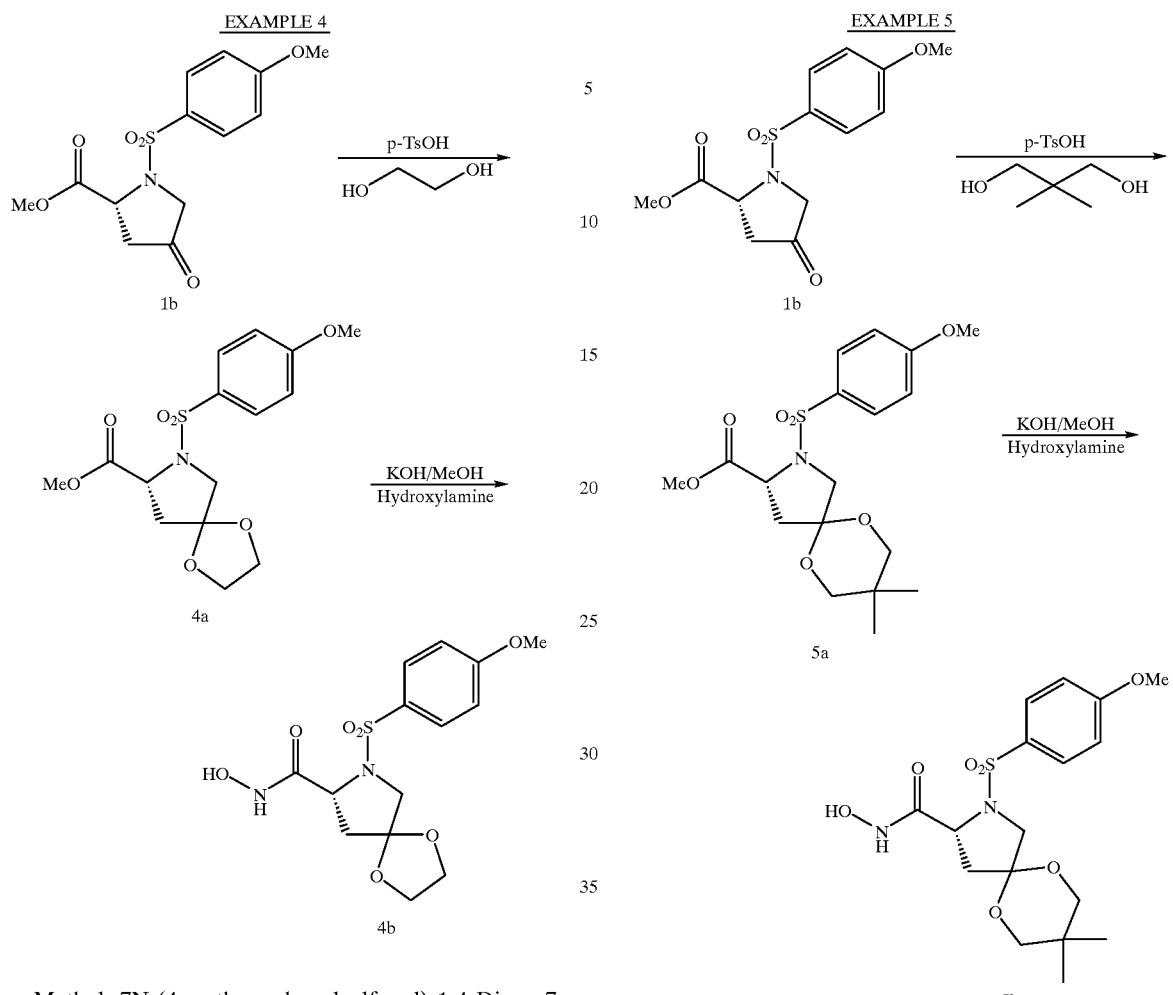

4a. Methyl 7N-(4-methoxyphenylsulfonyl)-1,4-Dioxa-7-azaspiro[4.4]nonane-8-(R-carboxylate:

The ketone 1b (0.5 g, 1.59 mmol) is dissolved in 50 mL of benzene, and then 1,2 ethanediol (0.108 g, 1.75 mmol) and p-toluenesulfonic acid (0.006 g, 0.0160 mmol) are added. The reaction mixture is heated to reflux for 18 h. The mixture is diluted with ether and neutralized with sodium bicarbonate (10 mL), extracted with ether three times and the combined ether layers are washed with ammonium chloride, dried over magnesium sulfate and evaporated. Purification of the resulting oil is accomplished by chromatography on silica gel with hexane/ethyl acetate (1/1) to afford the pure compound. MS (ESI): 437 (M$^+$+H), 454 (M$^+$+NH$_4$).

4b. N-Hydroxy-7N-(4-methoxyphenylsulfonyl)-1,4-Dioxa-7-azaspiro[4.4]nonane-8(R)-carboxylate:

A 1.76 M solution of potassium hydroxylamine in methanol is prepared. The 1.76 M solution (2.0 mL, 3.52 mmol) is added directly to the methyl ester 4a (0.146 g, 0.408 mmol) and the reaction mixture is stirred overnight. 1 N HCl is added to the solution to acidify it, then the resulting solution is extracted three times with ethyl acetate, dried with magnesium sulfate and evaporated to an oil. Purification of the resulting oil is accomplished by chromatography on silica gel using ethyl acetate/hexane/formic acid (2/1/0.1) to give the pure compound. MS (ESI): 438 (M$^+$+H), 455 (M$^+$+NH$_4$).

5a. Methyl 8N-(4methoxyphenylsulfonyl)-1,5-dioxo-3,3-dimethyl-8-azaspiro[5,4]decane-9(R)-carboxylate:

The ketone 1b (2 g, 3.19 mmol) is dissolved in 50 mL of benzene, and then 2,2-dimethyl-1,3-propane diol (0.4 g, 3.83 mmol) and p-toluenesulfonic acid monohydrate (57 mg, 0.3 mmol) are added. The mixture is refluxed using a Dean-Stark apparatus overnight. The solution is made basic by the addition of aqueous NaHCO$_3$ and then extracted three times with Et$_2$O. The organic layers are washed with ammonium chloride, dried over magnesium sulfate, filtered and evaporated. Purification of the product is accomplished by chromatography on silica gel with hexane/EtOAc (7:3) to afford the desired product. Ion spray MS: m/z 417 (M$^+$+NH$_4$), 440 (M$^+$+H).

5b. N-Hydroxy-8N-(4methoxyphenylsulfonyl)-1,5-dioxo-3,3-dimethyl-8-azaspiro [5,4]decane-9(R)-carboxamide:

A 1.5 M solution of potassium hydroxylamine in methanol is prepared as described in Fieser and Fieser, Vol 1, p 478. The 1.5 M solution (5.7 mL, 8 mmol) is added directly to the methyl ester 5a (0.32 g, 0.8 mmol) and the reaction mixture is stirred overnight. The solution is acidified with 1 N HCl, then the mixture is extracted three times with ethyl acetate, dried with magnesium sulfate, filtered and evaporated. The product is purified by reverse phase prep HPLC (60A40B, A, 95% H$_2$, 5% acetonitrile, 0.1% formic acid; B, 80% acetonitrile, 20% H$_2$O; 19× 300 mm waters SymmetryPrep C$_{18}$ column) to give the title compound as a white foaming solid.

Ion spray MS: m/z 418 (M$^+$+NH$_4$), 401 (M$^+$+H).

EXAMPLE 6

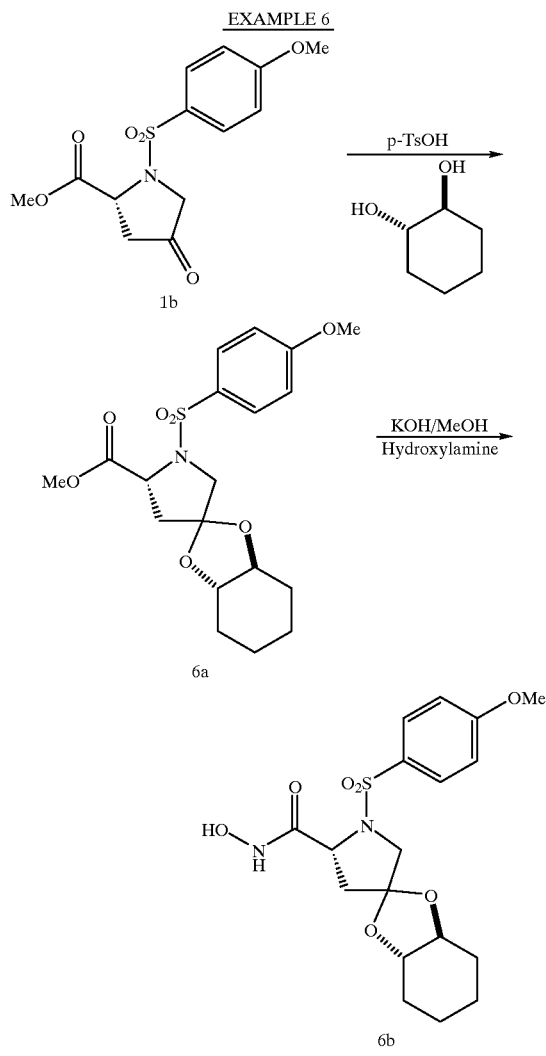

6a. Methyl 7N-(4-methoxyphenylsulfonyl)-1,4-dioxo-(2S),(3S)-trans-cyclohexyl-7-azaspiro 4,4]nonanes(R)-carboxylate:

The ketone 1b (1 g, 3.19 mmol) is dissolved in 50 mL of benzene, and then (1S,2S)-trans-1,2-cyclohexane diol (0.45 g, 3.82 mmol) and p-toluenesulfonic acid monohydrate (57 mg, 0.3 mmol) are added. The mixture is refluxed using a Dean-Stark apparatus overnight. The solution is made basic by the addition of aqueous NaHCO$_3$ and then extracted three times with Et$_2$O. The organic layers are washed with ammonium chloride, dried over magnesium sulfate, filtered and evaporated. Purification of the product is accomplished by chromatography on silica gel with hexane/EtOAc (1:3) to afford the desired product. Ion spray MS: m/z 429 (M$^+$+ NH$_4$), 412 (M$^+$+H).

6b. N-Hydroxy 7N-(4-methoxyphenylsulfonyl)-1,4-dioxo-(2S), (3S)-trans-cyclohexyl-7-azaspiro [4,4]nonane-8(R)-carboxamide:

A 1.5 M solution of potassium hydroxylamine in methanol is prepared as described in Fieser and Fieser, Vol 1, p 478. The 1.5 M solution (5.7 mL, 8 mmol) is added directly to the methyl ester 6a (0.33 g, 0.8 mmol) and the reaction mixture is stirred overnight. The solution is acidified with 1 N HCl, then the mixture is extracted three times with ethyl acetate, dried with magnesium sulfate, filtered and evaporated. The product is purified by reverse phase prep HPLC (60A40B, A, 95% H$_2$O, 5% acetonitrile, 0.1% formic acid; B, 80% acetonitrile, 20% H$_2$O; 19×300 mm waters SymmetryPrep C$_{18}$ column) to give the title compound as a white foaming solid. Ion spray MS: m/z 430 (M$^+$+NH$_4$), 413 (M$^+$+H).

EXAMPLE 7

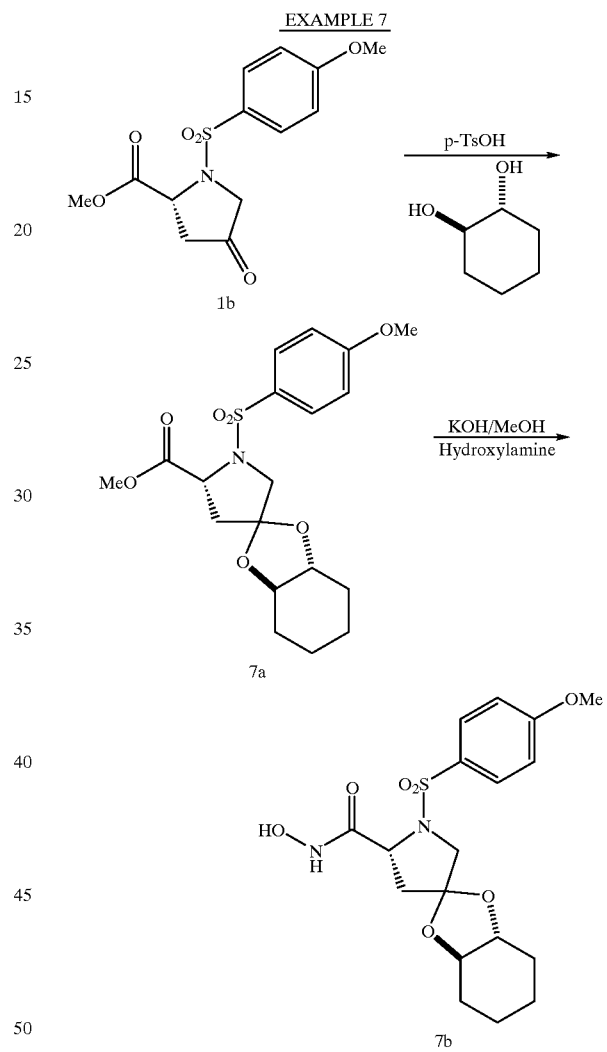

7a. Methyl 7N-(4-methoxyphenylsulfonyl)-1,4dioxo-(2R),(3R)trans-cyclohexyl-7-azaspiro [4,4]nonane-8(R)-carboxylate:

The ketone 1b (1 g, 3.19 mmol) is dissolved in 35 mL of benzene, and then (1R,2R)-trans-1,2-cyclohexane diol (0.45 g, 3.82 mmol) and p-toluenesulfonic acid monohydrate (29 mg, 0.15 mmol) are added. The mixture is refluxed using a Dean-Stark apparatus overnight. The solution is made basic by the addition of aqueous NaHCO$_3$ and then extracted three times with Et$_2$O. The organic layers are washed with ammonium chloride, dried over magnesium sulfate, filtered and evaporated. Purification of the product is accomplished by chromatography on silica gel with hexane/EtOAc (1:3) to afford the desired product. Ion spray MS: m/z 429 (M$^+$+ NH$_4$), 412 (M$^+$+H).

7b. N-Hydroxy 7N-(4-methoxyphenylsulfonyl)-1,4-dioxo-(2R), (3R)-trans-cyclohexyl-7-azaspiro [4,4]nonane-8(R)-carboxamide:

A 1.5 M solution of potassium hydroxylamine in methanol is prepared as described in Fieser and Fieser, Vol 1, p 478. The 1.5 M solution (12.8 mL, 19.2 mmol) is added directly to the methyl ester 7a (0.8 g, 1.92 mmol) and the reaction mixture is stirred overnight. The solution is acidified with 1 N HCl, then the mixture is extracted three times with ethyl acetate, dried with magnesium sulfate, filtered and evaporated. The product is purified by reverse phase prep HPLC (60A40B, A, 95% $H_2O$, 5% acetonitrile, 0.1% formic acid; B, 80% acetonitrile, 20% $H_2O$; 19×300 mm waters SymnmetryPrep $C_{18}$ column) to give the title compound as a white foaming solid. Ion spray MS: m/z 430 ($M^+ + NH_4$), 413 (M++H).

chromatography on silica gel with hexane/EtOAc (3:7) to afford the desired product. Ion spray MS: m/z 495 ($M^+ + NH_4$), 478 ($M^+ + H$).

8b. N-Hydroxy 8N-(4methoxyphenylsulfonyl)-1,5-dioxo-3-benzyloxy-8-azaspiro[5,4]-decane-9(R)-carboxamide:

A 1.5 M solution of potassium hydroxylamine in methanol is prepared as described in Fieser and Fieser, Vol 1, p 478. The 1.SM solution (9.3 mL, 13 mmol) is added directly to the methyl ester 8a (0.78 g, 1.63 mmol) and the reaction mixture is stirred overnight. The solution is acidified with 1 N HCl, then the mixture is extracted three times with ethyl acetate, dried with magnesium sulfate, filtered and evaporated. The product is purified by reverse phase prep HPLC (60A40B, A, 95% $H_2O$, 5% acetonitrile, 0.1% formic acid; B, 80% acetonitrile, 20% $H_2O$; 19× 300 mm waters SymmetryPrep $C_{18}$ column) to give the title compound as a white foaming solid. Ion spray MS: m/z 510 ($M^+ + Na$), 479 ($M^+ + H$).

EXAMPLE 8

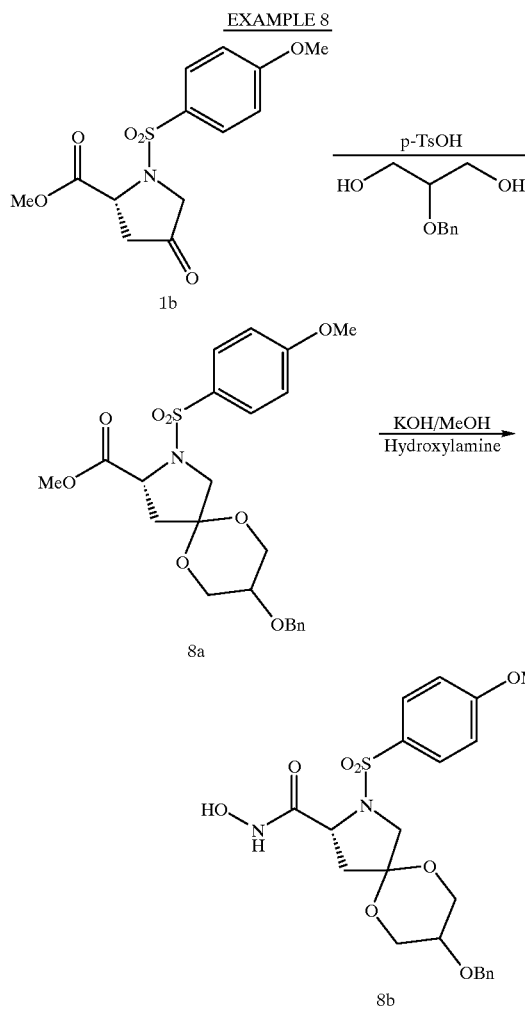

EXAMPLE 9

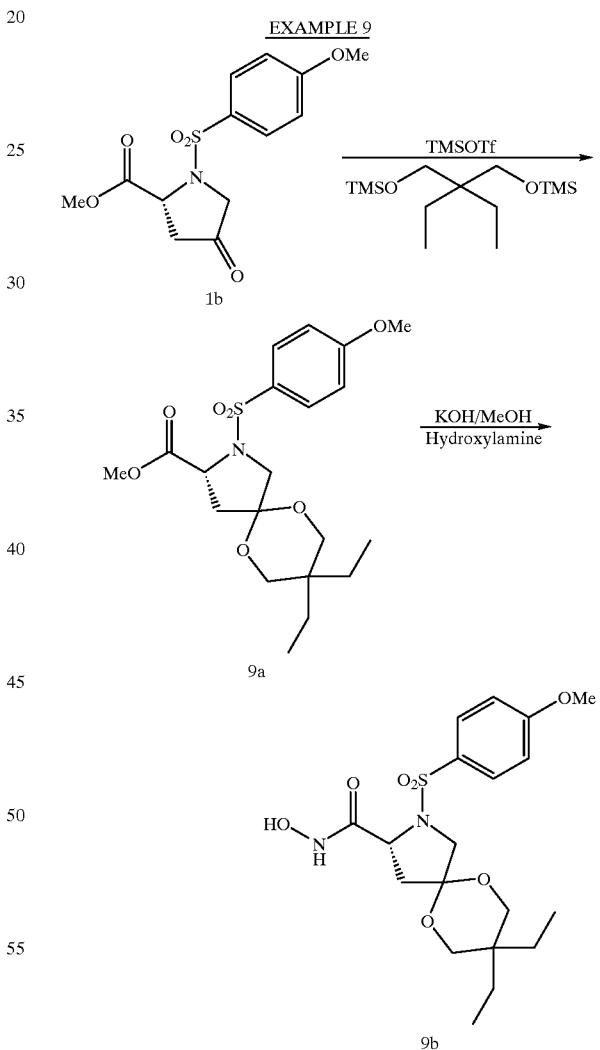

8a. Methyl 8N-(4methoxyphenylsulfonyl)-1,5-dioxo-3-benzyloxy-8-azaspiro[5,4]decane-9(R)-carboxylate:

The ketone 1b (3A g, 10.98 mmol) is dissolved in 65 mL of benzene, and then 2-benzyloxy-1,3-propane diol (2 g, 10.98 mmol) and p-toluenesulfonic acid monohydrate (104 mg, 0.15 mmol) are added. The mixture is refluxed using a Dean-Stark apparatus overnight. The solution is made basic by the addition of aqueous $NaHCO_3$ and then extracted three times with $Et_2O$. The organic layers are washed with ammonium chloride, dried over magnesium sulfate, filtered and evaporated. Purification of the product is accomplished by 9a. Methyl 8N-(4-methoxyphenylsulfonyl)-1,5-dioxo-3,3-diethyl-8-azaspiro[5,4]-decane-9(R)-carboxylate:

The ketone 1b (2.0 g, 6.39 mmol) was dissolved in methylene chloride (40 mL) followed by the addition of bis(trimethylsiloxy)-2,2-diethyl- 1,3-propanediol (8.8 g, 31.9 mmol). The reaction mixture was cooled to −78° C. in a dry ice/acetone bath, and trimethylsilyl trifluoromethanesulfonate (0.075 g, 0.31 mmol, 0.048 equiv) was added. The reaction mixture was then warmed to room temperature and stirred overnight Saturated sodium bicarbonate was added to neutralize the mixture, and the mixture was then extracted with water and methylene chloride. The organic layers were dried over sodium sulfate and evaporated under reduced pressure. Purification was accomplished by silica gel chromatography using an eluent system of 3:7 ethyl acetate: hexane. MS (ESI): 428 ($M^+$+H), 445 ($M^+$+$NH_4$)

9b. N-Hydroxy-8N-(4-methoxyphenyisulfonyl)-1,5-dioxo-3,3-diethyl-8-azaspiro[5,4]-decane-9(R)-carboxamide:

The ketal 9a (4.0 g, 9.68 mmol) is added to a 1.5 M solution of potassium hydroxylamine solution (77 mL, 14 equiv, prepared as described in Fieser and Fieser, Vol. 1, p. 478.). The reaction was quenched after 4 hours with 1 N HCl to a pH of 4–5. The reaction mixture was then diluted with water and extracted with ethyl acetate. The organic layers were dried over sodium sulfate, and evaporated under reduced pressure to a foamy solid. Purification was accomplished by silica gel chromatography using 3% methanol : 97% chloroform as the eluent. MS (ESI): 429 ($M^+$+H), 446 ($M^+$+$NH_4$).

The acetal 9a (1.2 g, 2.51 mmol) is taken in 20 mL of EtOH and the mixture is charged with 10% palladium on carbon (120 mg) and stirred under one atmosphere of hydrogen for 32 hr. TLC (EtOAc/hexane 1:1) indicated the reaction is complete. The mixture is filtered through celite and concentrated to give the desired product. Ion spray MS: m/z 405 ($M^+$+$NH_4$), 388 ($M^+$+H).

10b. N-Hydroxy 8N-(4-methoxyphenylsulfonyl)-1,5-dioxo-3-hydroxy-8azaspiro[5,4]decane-9(R)-carboxamide:

A 1.5 M solution of potassium hydroxylamine in methanol is prepared as described in Fieser and Fieser, Vol 1, p 478. The 1.5 M solution (11 mL, 16.5 mmol) is added directly to the methyl ester 10a (0.8 g, 2.06 mmol) and the reaction mixture is stirred overnight The solution is acidified with 1 N HCl, then the mixture is extracted three times with ethyl acetate, dried with magnesium sulfate, filtered and evaporated. The product is purified by reverse phase prep HPLC (80A20B, A, 95% $H_2O$, 5% acetonitrile, 0.1% formic acid; B, 80% acetonitrile, 20% $H_2O$; 19×300 mm waters SymmetryPrep $C_{18}$ column) to give the title compound as a white foaming solid. Ion spray MS: m/z 406 ($M^+$+$NH_4$), 389 ($M^+$+H).

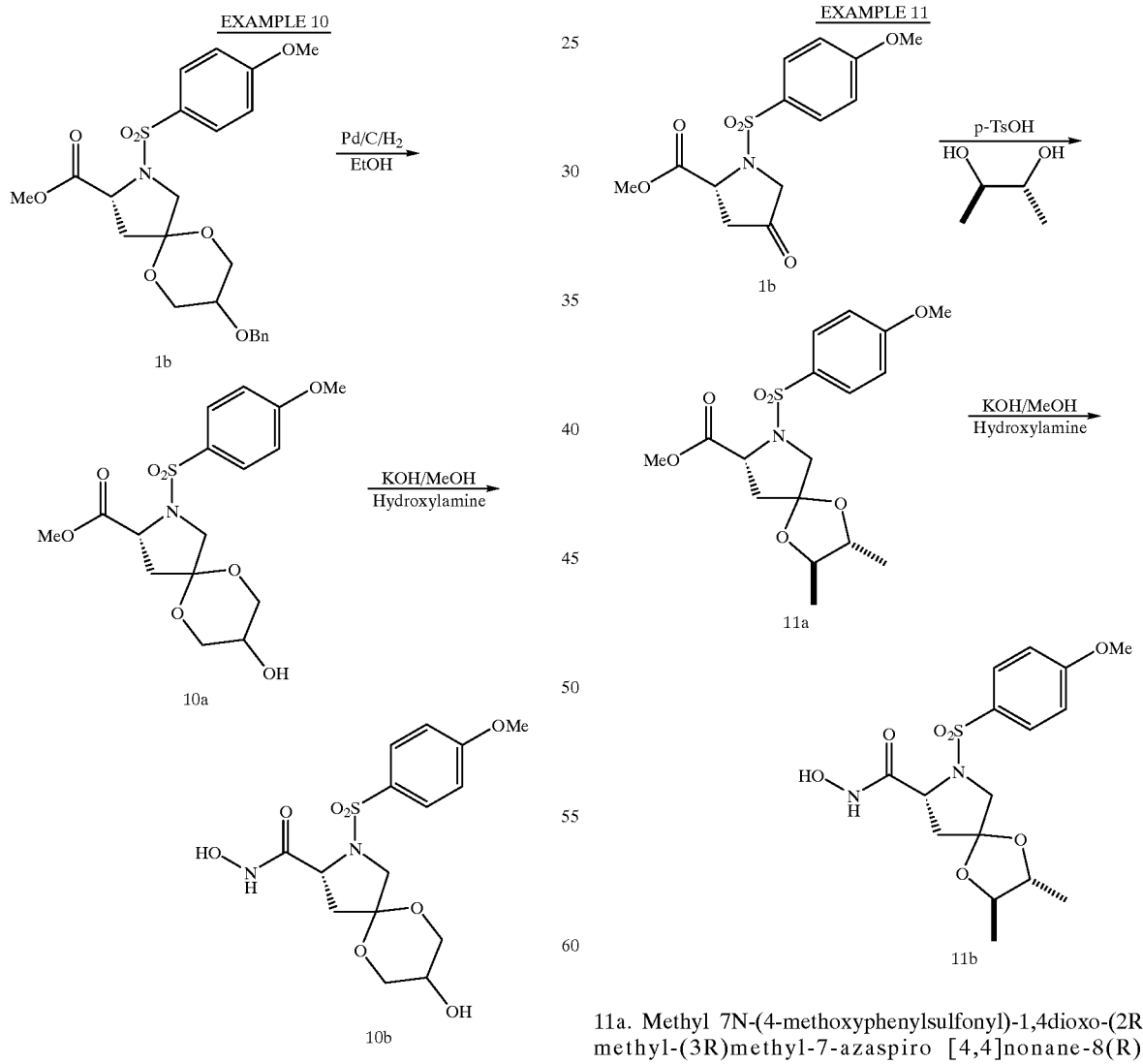

10a. Methyl 8N-(4-methoxyphenylsulfonyl)-1,5-dioxo-3-hydroxy-8-azaspiro[5,4]decane-9(R)-carboxylate:

11a. Methyl 7N-(4-methoxyphenylsulfonyl)-1,4dioxo-(2R)methyl-(3R)methyl-7-azaspiro [4,4]nonane-8(R)-carboxylate:

The ketone 1b (2 g, 6.38 mmol) is dissolved in 40 mL of benzene, and then (2R,3R)-(-)-2,3-butanediol (0.67 g, 7.66 mmol) and p-toluenesulfonic acid monohydrate (120 mg, 0.63 mmol) are added. The mixture is refluxed using a Dean-Stark apparatus overnight. The solution is made basic by the addition of aqueous $NaHCO_3$ and then extracted three times with $Et_2O$. The organic layers are washed with ammonium chloride, dried over magnesium sulfate, filtered and evaporated to afford the desired product Ion spray MS: m/z 404 ($M^+ + NH_4$), 386 ($M^+ + H$).

11 b. N-Hydroxy 7N-(4methoxyphenylsulfonyl)-1,4dioxo-(2R)-methyl-(3R)-methyl-7-azaspiro [4,4]nonane-8(R)-carboxamide:

A 1.5 M solution of potassium hydroxylamine in methanol is prepared as described in Fieser and Fieser, Vol 1, p 478. The 1.5 M solution (32 mL, 48 mmol) is added directly to the methyl ester 11a (2.5 g, 6.7 mmol) and the reaction mixture is stirred overnight. The solution is acidified with 1 N HCl, then the mixture is extracted three times with ethyl acetate, dried with magnesium sulfate, filtered and evaporated. The product is purified by flash chromatography ($CH_2Cl_2$/EtOAc/hexane, 5:3:2 to 5:4:1) on silica gel to give of the title compound as a white foaming solid. Ion spray MS: m/z 404 ($M^+ + NH_4$), 387 ($M^+ + H$).

5.74 mmol) and p-toluenesulfonic acid 5 monohydrate (89 mg, 0.47 mmol) are added. The mixture is refluxed using Dean and Stark apparatus overnight. The solution is made basic by the addition of aqueous $NaHCO_3$ and then extracted three times with $Et_2O$. The organic layers are washed with ammonium chloride, dried over magnesium sulfate, filtered and evaporated to afford the desired product. Ion spray MS: m/z 403 ($M^+ + NH_4$), 386 ($M^+ + H$).

12b. N-Hydroxy 7N-(4-methoxyphenylsulfonyl)-1,4dioxo-(2S)-methyl-(3S)-methyl-7-azaspiro [4,4]nonane-8(R)-carboxamide:

A 1.5 M solution of potassium hydroxylamine in methanol is prepared as described in Fieser and Fieser, Vol 1, p 478. The 1.5 M solution (10 mL, 19 mmol) is added directly to the methyl ester 12a (0.92 g, 2.39 mmol) and the reaction mixture is stirred overnight. The solution is acidified with 1 N HCl, then the mixture is extracted three times with ethyl acetate, dried with magnesium sulfate, filtered and evaporated. The product is purified by flash chromatography ($CH_2Cl_2$/$CH_3OH$, 95:5) on silica gel to give the title compound as a white foaming solid. Ion spray MS: m/z 409 ($M^+ + Na$), 387 ($M^+ + H$).

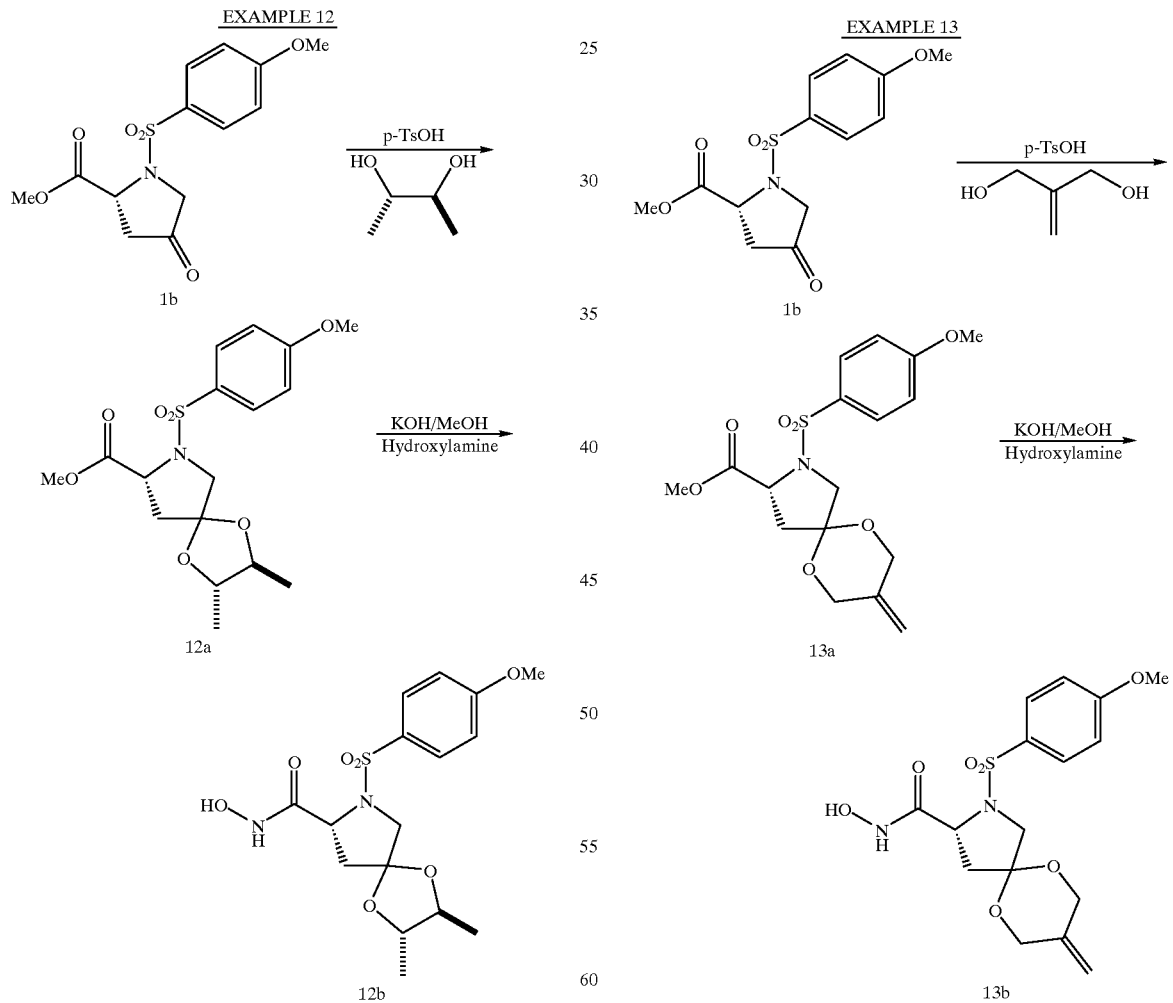

12a. Methyl 7N-(4-methoxyphenylsulfonyl)-I,4-dioxo-(2S)-methyl-(3S)methyl-7-azaspiro [4,4]nonane-8(R)-carboxylate:

The ketone 1b (1.5 g, 4.78 mmol) is dissolved in 45 mL of benzene, and then (2S,3S)-(+)-2,3-butanediol (0.52 g, 13a. Methyl 8N-(4-methoxyphenylsulfonyl)-1,5-dioxo-3-methylene-8-azaspiro[5,4]decane-9(R)-carboxylate:

The ketone 1b (3 g, 9.58 mmol) is dissolved in 45 mL of benzene, and then 2-methylene-1,3-propane diol (1.04 g, 11.8 mmol) and p-toluenesulfonic acid monohydrate (182 mg, 0.95 mmol) are added. The mixture is refluxed using a Dean-Stark apparatus overnight. The solution is made basic by the addition of aqueous NaHCO$_3$ and then extracted three times with Et$_2$O. The organic layers are washed with ammonium chloride, dried over magnesium sulfate, filtered and evaporated. Purification of the product is accomplished by chromatography on silica gel with hexane/EtOAc (3:7 to 4:6) to afford the desired product. Ion spray MS: m/z (rel intensity) 401 (M$^+$+NH$_4$), 384 (M$^+$+H).

13b. N-Hydroxy 8N-(4-methoxyphenylsulfonyl)-I,5dioxo-3-methylene-8-azaspiro[5,4]-decane-9(R)-carboxamide:

A 1.5 M solution of potassium hydroxylamine in methanol is prepared as described in Fieser and Fieser, Vol 1, p 478. The 1.5 M solution (14 mL, 26 mmol) is added directly to the methyl ester 13a (1.25 g, 3.26 mmol) and the reaction mixture is stirred overnight. The solution is acidified with 1 N HCl, then the mixture is extracted three times with ethyl acetate, dried with magnesium sulfate, filtered and evaporated. The product is purified by flash chromatography (CH$_2$Cl$_2$/CH$_3$OH, 95:5) on silica gel to give the title compound as a white foaming solid. Ion spray MS: m/z 407 (M$^+$+Na), 385 (M$^+$+H).

EXAMPLE 14

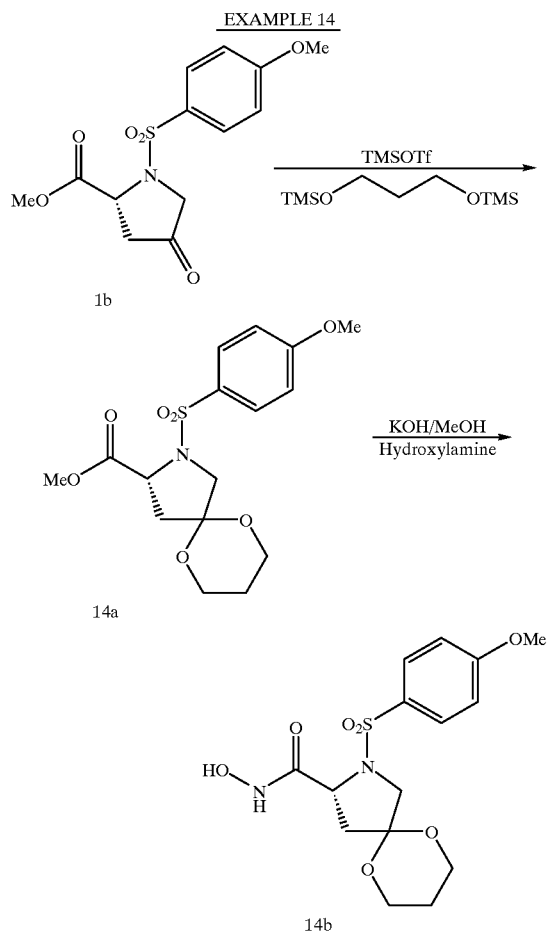

14a. Methyl 1N-1(4-methoxyphenyl)sulfonyl]-1,4-dioxa-azaspiro[4.5]nonane-2-carboxylate The ketone 1b (20.0 g, 63.9 mmol) is dissolved in methylene chloride (500 mL) followed by the addition of bis(trimethylsiloxy)-1,3-propanediol (51.9 g, 221.9 mmol, 3.5 equiv). The reaction mixture is cooled to −78° C. in a dry ice acetone bath, and trimethylsilyl trifluoromethane-sulfonate (3.6 g, 3.07 mmol, 0.048 equiv) is added. The reaction mixture is then warmed to room temperature and stirred overnight. Saturated sodium bicarbonate is added to neutralize the mixture, and the mixture is then extracted with water and methylene chloride (3×200 mL). The organic layers are dried over sodium sulfate and evaporated under reduced pressure. Purification is accomplished by silica gel chromatography using an eluent system of 1:1 ethyl acetate: hexane to afford the product as a colorless oil. MS (ESI): 372 (M$^+$+H), 389 (M$^+$+NH$_4$).

14b. N-Hydroxy-1N-[(4methoxyphenyl)sulfonyl]-1,4dioxa-azaspiro[4.5]nonane2-carboxamide (C)

The ketal 14a (14.0 g, 37.7 mmol) is added to a 1.5 M solution of potassium hydroxylamine solution (300 mL, 14 equiv, prepared as described in Fieser and Fieser, Vol. 1, p. 478.). The reaction is quenched after 1 hour with 1 N HCl to a pH of 4.5. The reaction mixture is then diluted with water and extracted with ethyl acetate. The organic layers are dried (Na$_2$SO$_4$), and evaporated under reduced pressure to a foamy solid. Purification is accomplished by silica gel chromatography (eluent: 3% methanol : 97% chloroform). The product is obtained as a white powder. MS (EST): 372 (M$^+$+H), 390 (M$^+$+NH$_4$).

EXAMPLE 15

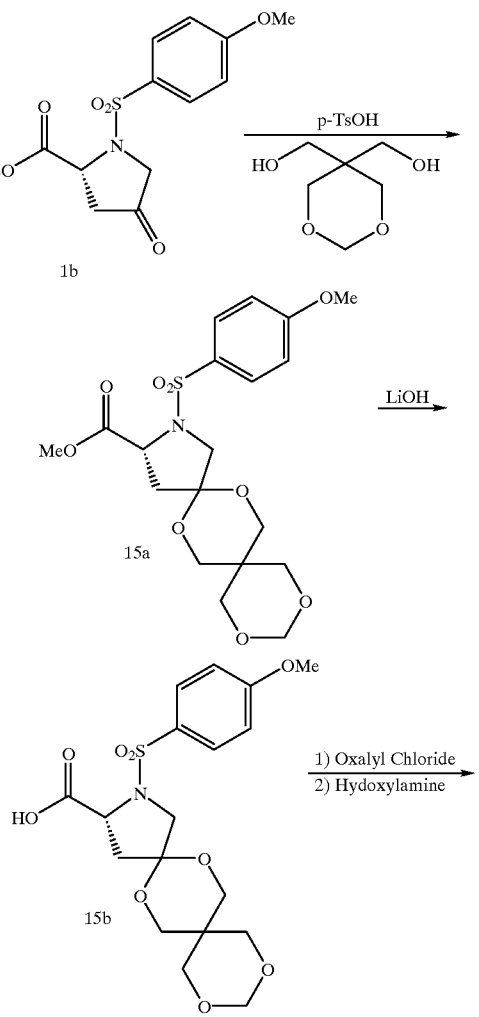

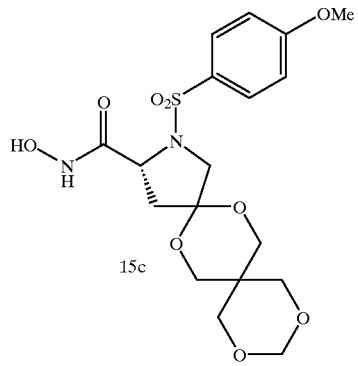

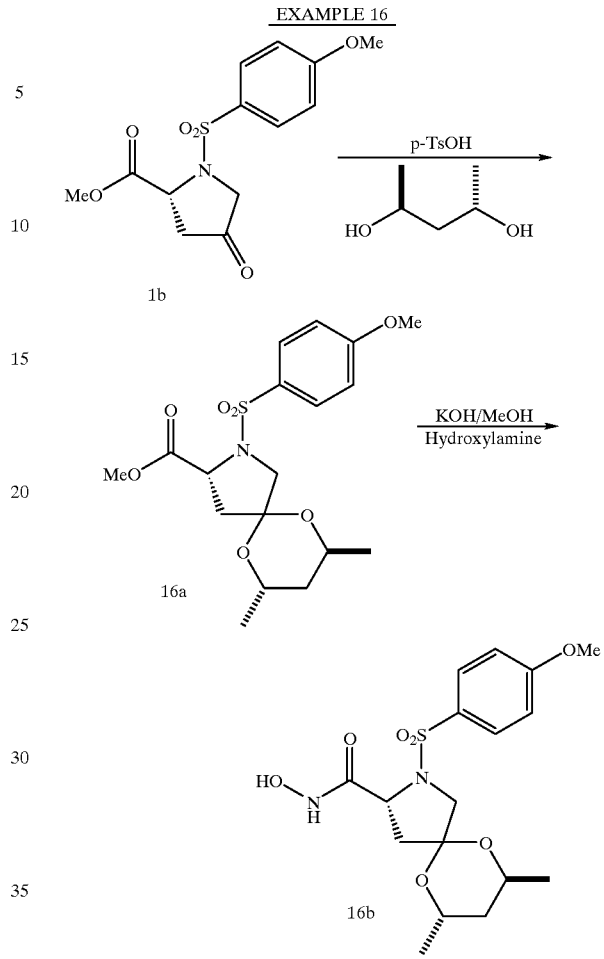

EXAMPLE 16

15a. Methyl 11N-[(4-methoxyphenyl)sulfonyl]-2,4,8,1⁴-tetraoxa-11-azadispiro[4.2.5.2]-pentadecane-2-carboxylate The ketone 1b (1.0 g, 3.19 mmol) in benzene (60 mL) is stirred at room temperature and then 1,3 dioxane-5,5 dimethanol (0.56g, 3.83 mmol) and p-toluenesulfonic acid (0.01 equiv) are added. The reaction is then equipped with a Dean-Stark trap and a reflux condenser under a nitrogen atmosphere. The reaction is heated to reflux overnight. The reaction mixture is quenched and basified with saturated sodium bicarbonate. The resulting mixture is extracted with ethyl acetate and water and the organic layers are dried over sodium sulfate and concentrated under reduced pressure. Purification is accomplished by chromatography on silica gel using hexane: ethyl acetate (1:1). MS (ESI) 444 (M$^+$+H), 461 (M$^{++NH}{}_4$).

15b. 11N-[(4methoxyphenyl)sulfonyl]-2,4,8,14-tetraoxa-11-azadispiro[4.2.5.2]pentadecane-2-carboxylic acid:

The ketal 15a (0.90 g, 2.03 mmol) is dissolved in methanol (10 mL) and THF (5 mL). Lithium hydroxide (1.0 g, excess) in water (5 mL) is next added, and the resulting mixture is stirred for 1 hour. The reaction is quenched by the addition of 1 N HCl to reach pH =2. The reaction mixture is then extracted with methylene chloride and water. The organic layers are dried over sodium sulfate and concentrated under reduced pressure to give the product. MS (ESI): 430 (M$^+$+H), 447 (M$^+$+NH$_4$).

15c. N-Hydroxy-1N-[(4-methoxyphenyl)sulfonyl]-2,4,8,14-tetraoxa-11-azadispiro[4.2.5.2]-pectadecane-2-carboxamide:

The carboxylic acid 15b (0.43 g, 1.0 mmol) is dissolved in methylene chloride (15 mL), followed by the addition of oxalyl chloride (0.26 g, 2.05 mmol) and then DMF (0.07 g, 1.0 mmol) under nitrogen atmosphere. In a separate flask, hydroxylamine hydrochloride (0.28 g, 4.0 mmol) is dissolved in water (3 ML), followed by the addition of THF (10 mL). The amine solution is cooled in an ice bath and triethylamine (0.61 mL, 6.0 mmol) is added. The acid mixture is then added to the hydroxylamine solution at 0 °C. The reaction mixture is then warmed to room temperature and stirred for 1 hour. To neutralize the solution, 1 N HCl is added to achieve pH ~5. The mixture is then extracted with methylene chloride and water. The organic layers are dried over sodium sulfate and concentrated under reduced pressure. Purification is accomplished by reverse phase chromatography (Waters Symmetry C$_{18}$) using a solvent system of 40% A (95% water, 5% acetonitrile, 0.1% formic acid) and 60% B ( 20% water, 80% water). MS (ESI): 445 (M$^+$+H), 462 (M$^+$+NH$_4$).

16a. Methyl 1N-(4-methoxyphenylsulfonyl)-1,5dioxaazaspiro[4.5]nonane-2S,4S-dimethyl-2-carboxylate:

The ketone 1b (1.0 g, 3.19 mmol) is dissolved in benzene (60 mL) and then 2S,4S-(+)-Pentanediol (0.40g, 3.82 mmol) and p-toluene sulfonic acid (0.01 equiv) are added. The reaction is equipped with a Dean-Stark trap and a reflux condenser under a nitrogen atmosphere. The reaction is then heated to reflux over night. The reaction mixture is quenched and basified with saturated sodium bicarbonate solution. The mixture is then extracted with ethyl acetate and water, the organic layers are dried over sodium sulfate and then concentrated under reduced pressure. Purification is accomplished by chromatography on silica gel using hexane: ethyl acetate (7:3).

16b. N-Hydroxy-1N-(4-methoxyphenylsulfonyl)1,5-dioxaazaspiro[4.5]nonane-2S,4S-dimethyl-2-carboxamide:

The ketal 16a (0.9 g, 2.25 mmol) is added to a 1.5 M solution of potassium hydroxylamine solution (10.2 mL, 18 mmol, prepared as described in Fieser and Fieser, Vol. 1, p. 478.) and the resulting mixture is stirred overnight. The reaction is quenched and neutralized to pH=5 with 1 N HCl. The solution is diluted with water and extracted with ethyl acetate. The organic layers are dried over sodium sulfate and concentrated under reduced pressure. Purification is performed by reverse phase HPLC (Waters Symmetry C$_1$8) using 60%A (95% water, 5% acetonitrile, 0.1 formic acid) and 40%B ( 20% water, 80% acetonitrile). MS (ESI): 386 (M$^+$+H), 403 (M+NH$_4$).

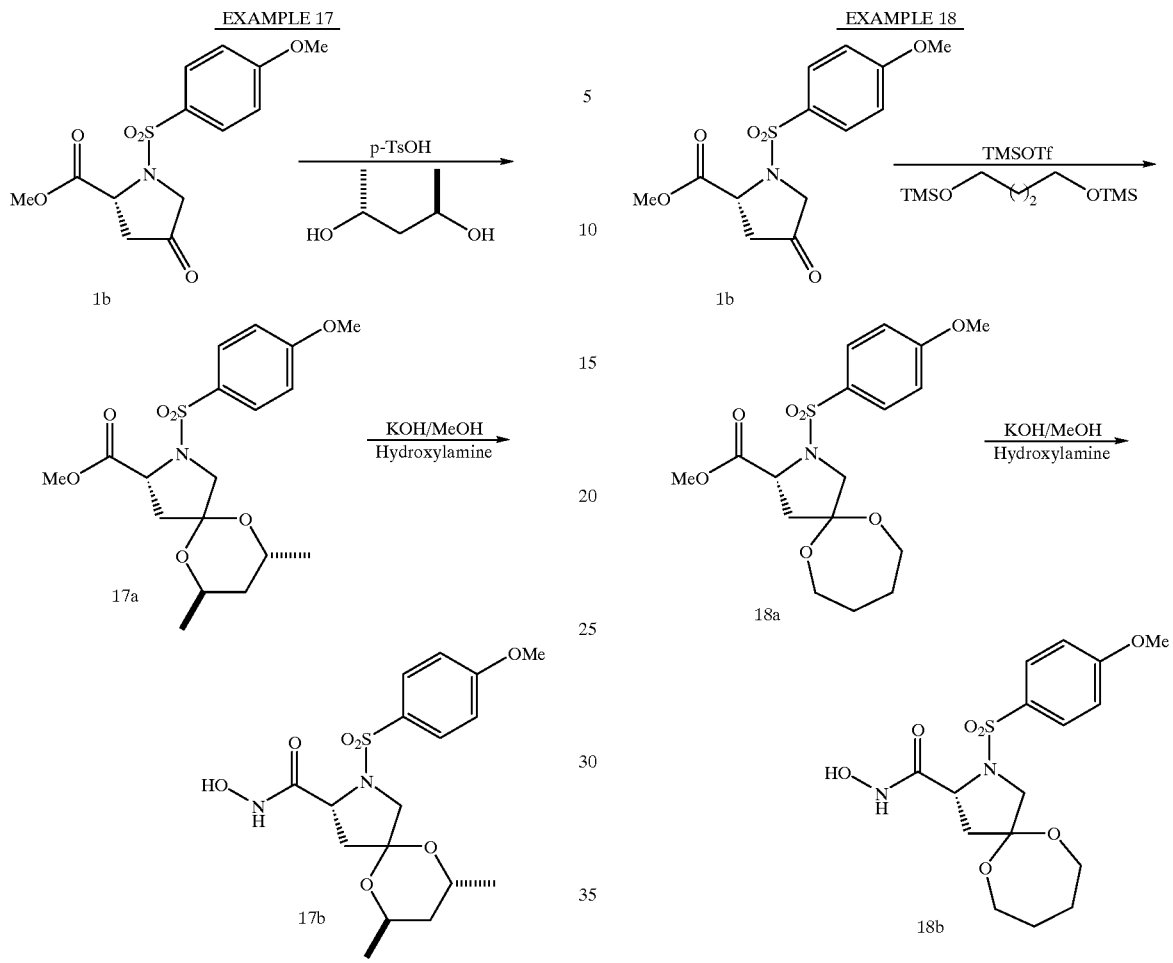

17a. Methyl 1N-(4methoxyphenylsulfonyl)-1,5-dioxa-azaspiro[4.5]nonane-2R,4R-dimethyl-2-carboxylate:

The ketone (1.0 g, 3.19 mmol) is dissolved in benzene (60 mL) and then 2R,4R-(+)-Pentanediol (0.40 g, 3.82 mmol) and p-toluene sulfonic acid (0.01 equiv) are added. The reaction is equipped with a Dean-Stark trap and a reflux condenser under a nitrogen atmosphere. The reaction is heated to reflux at overnight. The reaction mixture is quenched and basified with saturated sodium bicarbonate and then extracted with ethyl acetate and water. The organic layers are dried over sodium sulfate and concentrated under reduced pressure. Purification is accomplished by chromatography on silica gel using hexane: ethyl acetate (7:3) as the eluent. MS (ESI): 400 (M+H$^+$), 417 (M$^+$+NH$_4$).

17b. N-Hydroxy-1N-(4-methoxyphenylsulfonyl)-1,5-dioxa-azaspiro[4.5]nonane-2R,4R-dimethyl-2-carboxamide:

The ketal (0.9 g, 2.25 mmol) is added to a 1.5 M solution of potassium hydroxylamine solution (10.2 mL, 18 mmol, prepared as described in Fieser and Fieser, Vol. 1, p. 478.) and the resulting mixture is stirred overnight. The reaction is quenched and neutralized to pH=5 with 1 N HCl. The solution is diluted with water and extracted with ethyl acetate. The organic layers are dried over sodium sulfate and concentrated under reduced pressure. Purification is accomplished through crystallization with acetonitrile. MS (ESI): 401 (M$^+$+H), 418 (M$^+$+NH$_4$).

18a. Methyl 1N-[(4methoxyphenyl)sulfonyl]-1,5-dioxa-azaspiro[4.6]decane-2-carboxylate:

The ketone 1b (1.0 g, 3.19 mmol) is dissolved in methylene chloride (25 mL) followed by the addition of bis (trimethylsiloxy)-1,4-butanediol (3.73 g, 15.9 mmol, 5.0 equiv). The reaction mixture is cooled to −78° C. in a dry ice acetone bath, and trimethylsilyl trifluoromethanesulfonate (0.36 g, 1.53 mmol, 0.048 equiv) is added. The reaction mixture is then warmed to room temperature and stirred overnight. Saturated sodium bicarbonate is added to neutralize the mixture, and the mixture is then extracted with water and methylene chloride (3×50 mL). The organic layers are dried over sodium sulfate and evaporated under reduced pressure. Purification is accomplished by silica gel chromatography using an eluent system of 1:1 ethyl acetate: hexane to afford the product. MS (ESI): 386 (M$^+$+H), 403 (M$^+$+NH$_4$).

18b. N-Hydroxy-1N-[(4-methoxyphenyl)sulfonyl]-1,5-dioxa-azaspiro[4.6]decane-2-carboxamide:

The ketal 18a (1.0 g, 2.6 mmol) is added to a 1.5 M solution of potassium hydroxylamine solution (12 mL, 8 equiv, prepared as described in Fieser and Fieser, Vol. 1, p. 478.). The reaction is quenched after 1 hour with 1 N HCl to a pH of 4.5. The reaction mixture is then diluted with water and extracted with ethyl acetate. The organic layers are dried (Na$_2$SO$_4$), and evaporated under reduced pressure to a foamy solid. Purification is accomplished by silica gel chromatography (eluent: 3% methanol : 97% chloroform). The product is obtained as a white powder. MS (ESI): 387 (M$^+$+H), 404 (M$^+$+NH$_4$).

EXAMPLE 19

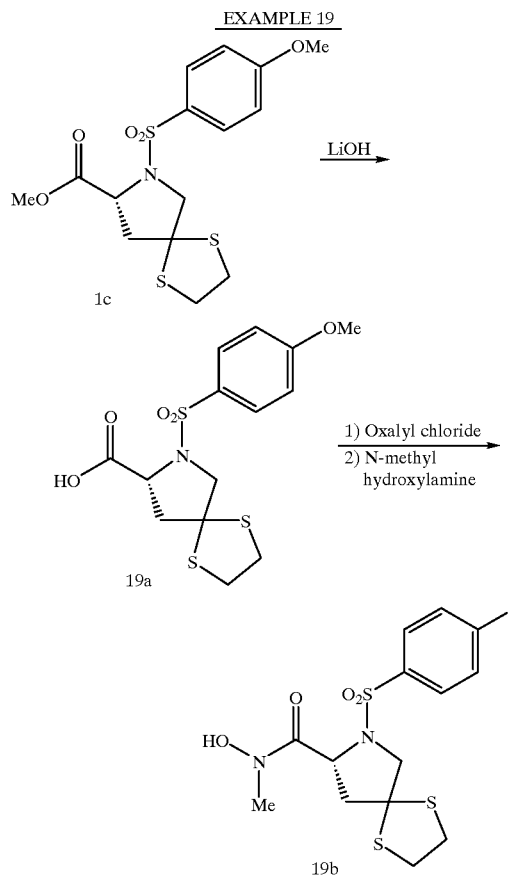

EXAMPLE 20

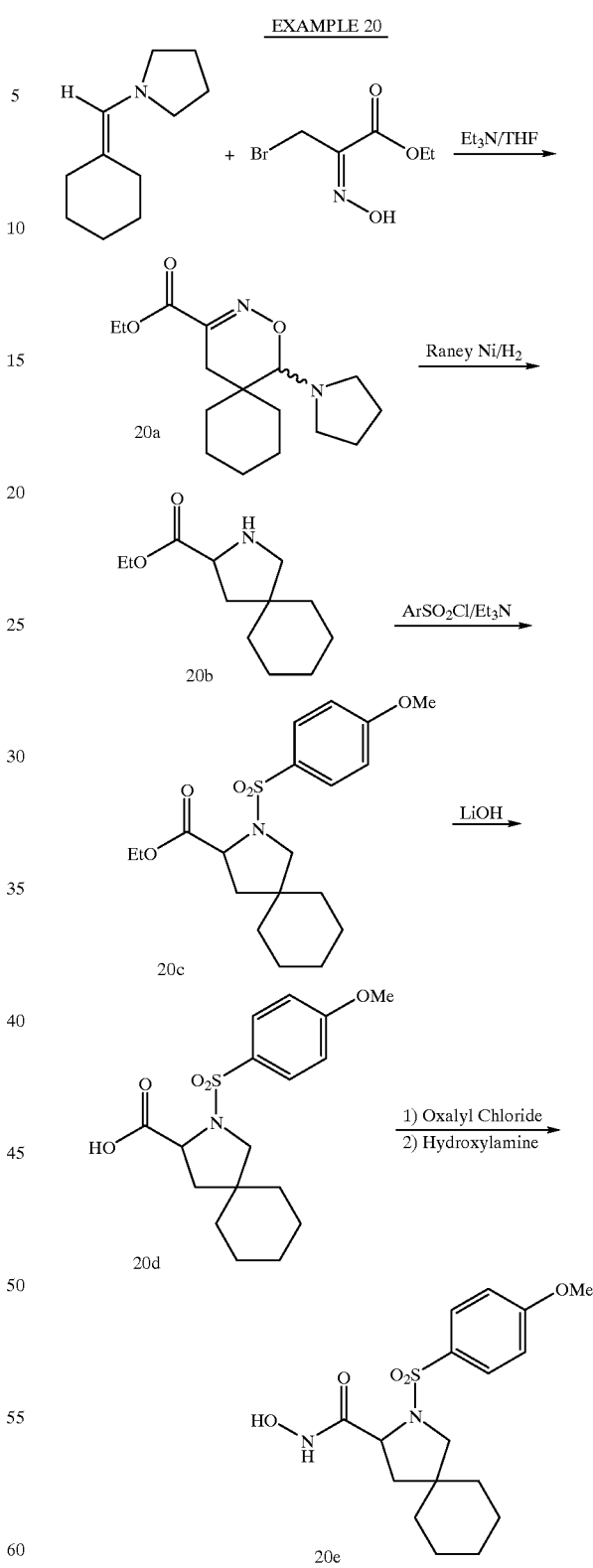

19a. N-methyl-7N-[(4-methoxyphenyl)sulfonyl]-1,4-dithia-7-azaspiro[4.4]nonane-8(R)-carboxylic acid:

The ketal 1c (0.90 g, 2.31 mmol) is dissolved in methanol (10 mL) and THF (5 mL). Lithium hydroxide (1.0 g, excess) in water (5 mL) is next added, and the resulting mixture is stirred for 1 hour. The reaction is quenched by the addition of 1 N HCl to reach pH =2. The reaction mixture is then extracted with methylene chloride and water. The organic layers are dried over sodium sulfate and concentrated under reduced pressure to give the product. MS (ESI): 376 ($M^+$+H), 393 ($M$++$NH_4$). 19b. N-Hydroxy-N-methyl-7N-[(4-methoxyphenyl)sulfonyl]-1,4-dithia-7-azaspiro[4.4]-nonane-8(R)-carboxamide:

The carboxylic acid 19a (0.5 g, 1.33 mmol) is dissolved in methylene chloride (15 mL), followed by the addition of oxalyl chloride (0.35 g, 2.73 mmol) and then DMF (0.097 g, 1.33 mmol) under nitrogen atmosphere. In a separate flask, hydroxylamine hydrochloride (0.37 g, 5.33 mmol) is dissolved in water (3 mL), followed by the addition of THF (10 mL). The amine solution is cooled in an ice bath and triethylamine (1.1 mL, 8.0 mmol) is added. The acid mixture is then added to the hydroxylamine solution at 0° C. The reaction mixture is then warmed to room temperature and stirred for 1 hour. To neutralize the solution, 1 N HCl is added to achieve pH ~5. The mixture is then extracted with methylene chloride and water. The organic layers are dried over sodium sulfate and concentrated under reduced pressure. Purification is accomplished by reverse phase chromatography (Waters Symmetry $C_1I$) using a solvent system of 40% A (95% water, 5% acetonitrile, 0.1% formic acid) and 60% B (20% water, 80% water). MS (ESI): 391 ($M^+$+H), 408 ($M^+$+$NH_4$).

20a. Ethyl 6'-(1-Pyrrolidinyl)spirolcyclohexane-2,5'(6'H)-[4H-1,2]-oxazine-3'-carboxylate:

The 1-(cyclohexylidenemethyl)-pyrrolidine (9.0 g, 54.4 mmol) in THF (100 mL) is stirred at room temperature and then ethyl 3-bromo-2-hydroxyiminopropanoate (12.2 g, 57.7 mmol, 1.06 equiv, ref: Ottenheijm, H. C. J.; Plate, R.; Noordlik, J. H.; Herscheid, J. D. M. *J Org Chem.* 1982, 47, 2147.) is added in portions over 15 minutes. The reaction mixture warms and the resulting mixture is stirred at room temperature for 30 minutes. Triethylamine (5.9 g, 58.3 mmol, 1.07 equiv) is next added. The reaction mixture again warms, and the resulting solution is stirred for an additional 2 h at room temperature. The reaction mixture is diluted with water (100 mL) and extracted with ethyl acetate. The organic extracts are dried ($Na_2SO_4$) and concentrated to an oil under reduced pressure. Purification of the oil is accomplished by chromatography on silica gel using 85/15 hexane/EtOAc as the eluent. The product is obtained as a light yellow oil. MS (ESI): 295 ($M^+ +H$).

20b. Ethyl 1-azabicyclo-14.5.01-decane-2-carboxylate:

The oxazine (2.0 g, 6.8 mmol) in ethanol (100 mL) is placed in a Parr bottle with Raney Nickel (Aldrich, W-2, 2 g). The reaction mixture is placed under a hydrogen atmosphere (30 psi) and shaken until hydrogen uptake ceased. The reaction mixture is then filtered through celite and concentrated to a light oil. No further purification is performed. MS (ESI): 212 ($M^+ +H$).

20c. Ethyl 1N-(4-methoxyphenylsulfonyl)-1-azabicyclo-[4.5.0]-decane-2-carboxylate:

The amine (1.4 g, 6.6 mmol) in dioxane (40 mL) and water (40 mL) is stirred at room temperature and then triethylamine (2.0 g, 19.8 mmol, 3 equiv) followed by 4-methoxybenzenesulfonyl chloride (1.51 g, 7.2 mmol, 1.1 equiv) are added. The resulting solution is stirred at room temperature for 18 h. The reaction mixture is acidified with 1 N HCl and then the mixture is poured into water. The solution is extracted with methylene chloride and the combined organic extracts are dried ($MgSO_4$) and concentrated to an oil under reduced pressure. Purification of the oil is accomplished by chromatography on silica gel using 8/2 hexane/EtOAc as the eluent. The product is obtained as a clear oil which solidifies upon standing.

20d. 1N-(4-Methoxyphenylsulfonyl)-1-azabicyclo-[4.5.0]-decane-2-carboxylic acid:

The ethyl ester (1.5 g, 3.93 mmol) in THF (10 mL) and methanol (20 mL) are stirred at room temperature and then lithium hydroxide (2.0 g) in water (20 mL) is added. The resulting solution is stirred at room temperature for 18 h. The reaction mixture is acidified with 1 N HCl and then the mixture is poured into water. The solution is extracted with methylene chloride and the combined organic extracts are dried ($Na_2SO_4$) and then concentrated to an oil under reduced pressure. The oil solidifies to a white solid upon standing.

20e. N-Hydroxy-1N-(4-methoxyphenyisulfonyl)-1-azabicyclo-14.5.01-decane2-carboxamide:

The carboxylic acid (0.7 g, 1.98 mmol) in dichloromethane (10 mL) is stirred at room temperature and then oxalyl chloride (0.52 g, 4.06 mmol, 2.05 equiv) and DMF (0.14 g, 1.98 mmol) are added. The resulting solution is stirred at room temperature for 30 minutes. In a separate flask, hydroxylamine hydrochloride (0.55 g, 7.92 mmol, 4 equiv) in THF (10 mL) and water (2 mL) are stirred at 0° C. Triethylamine (1.2 g, 11.9 mmol, 6 equiv) is added and the resulting solution is stirred at 0° C. for 15 minutes. The acid chloride solution is next added to the hydroxylamine solution at 0° C. and the resulting mixture is allowed to stir overnight at room temperature. The reaction mixture is acidified with 1 N HCl and then the solution is extracted with dichloromethane.

The organic extracts are dried ($Na_2SO_4$) and concentrated to a solid under reduced pressure. The solid is recrystallized from $CH_3CN/H_2O$ to provide the desired product as a white powder. MS (ESI): 369 ($M^+ +H$), 386 ($M^+ +NH_4$).

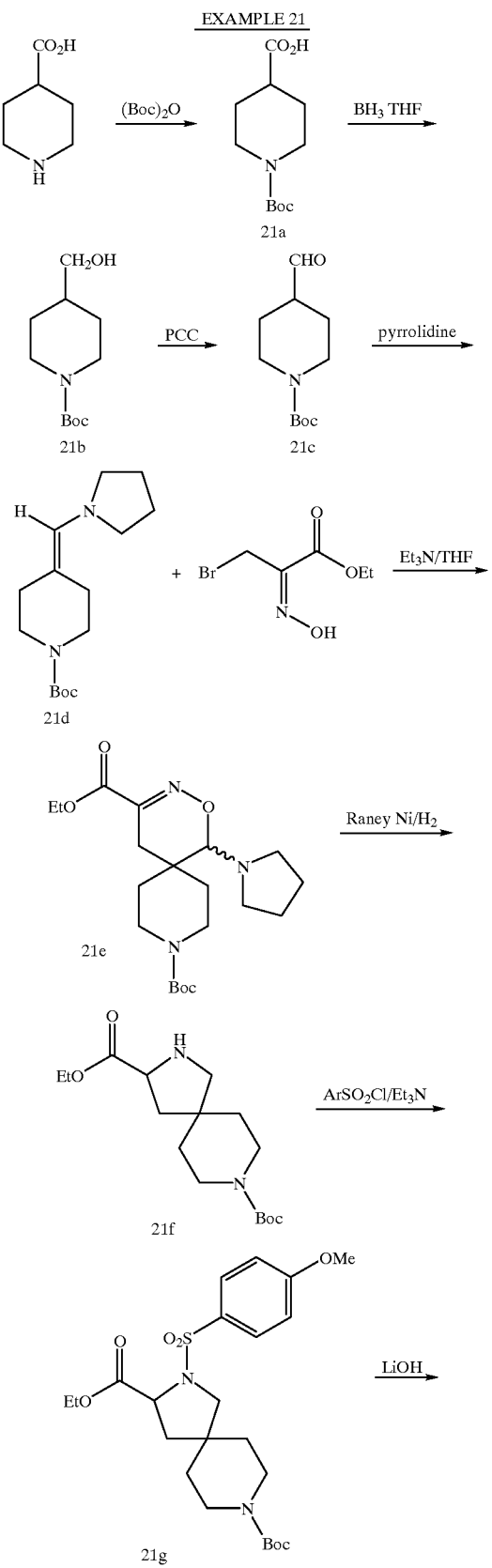

EXAMPLE 21

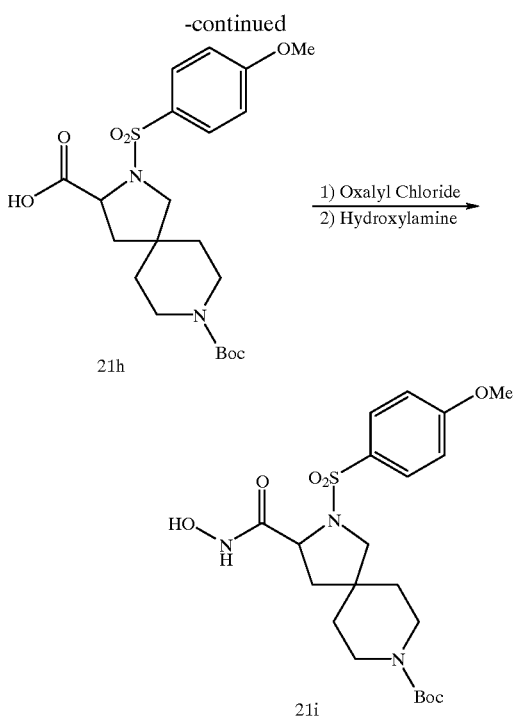

21a. 1-t-butyldicarbonate4piperidinecarboxylic acid:

The isonipecotic acid (15.0 g, 95.1 mmol) is dissolved in p-dioxane (75 mL), followed by the addition of NaOH (4.0 g, 100 mmol) in water (75 mL). To the stirring solution, di-t-butyldicarbonate (20.8 g, 95.1 mmol) was added, and the reaction mixture was stirred overnight. The reaction is quenched and acidified with 1 N HCl to pH=1–2. The resulting mixture is then diluted with water, and extracted with methylene chloride. The organic layers are dried over sodium sulfate, and concentrated under reduced pressure to give the desired product as a colorless oil. MS (ESI): 230 (M$^+$+H), 247 (M$^+$+NH$_4$).

21 b. 1-t-butyldicarbonate-4-(hydroxymethyl)piperidine:

The protected carboxylic acid 21a (21.7g, 95.1 mmol) is dissolved in ThF (300 mL) and cooled to 0° C. in an ice bath. A 1.0 M solution of BH$_3$-THF (237.75 mL, 237.25 mmol) was added to the stirring reaction mixture. The reaction was then warmed to room temperature and stirred overnight. The reaction mixture was cooled to 0° C., and water was added very slowly to quench the reaction until bubbling ceases. Once the reaction is complete, it is acidified with 1 N HCl and extracted with ethyl acetate. The organic layers are dried over sodium sulfate, and concentrated under reduced pressure to provide the desired product. MS (ESI): 216 (M$^+$+H).

21c. 1-t-butyldicarbonate-4-piperidinecarboxaldehyde:

The acohol 21b (20.2 g, 93.9 mmol) is dissolved in methylene chloride (300 mL). To this stirring solution, pyridinium chlorochromate (20.2 g, 93.9 mmol, 1.0 equiv) is added. The reaction mixture became a dark suspension which was stirred at room temperature for 4 h. The solution is then decanted from the black- residue and the residue is rinsed with ether several times. The combined organic layers are filtered through a silica gel plug and some extra ether is used as the eluent. The resulting solution is concentrated under reduced pressure, and purified by chromatography on a silica gel column using hexane: ethyl acetate (1.5:1).

21d. 1-t-butyldicarbonate-4-(pyrrolidinoethylene)piperidine:

The aldehyde 21c (8.3 g, 39.1 mmol) is dissolved in 150 mL of benzene, followed by the addition of pyrrolidine (4.2 g, 58.6 mmol). The reaction flask is equipped with a Dean-Stark trap and a reflux condenser and refluxed for 5 hours. The solvent is then removed under reduced pressure, No further purification is needed. MS (ESI): 267 (M$^+$+H).

21 e. Ethyl 6'-(1-Pyrrolidinyl)spiro[4-t-butyldicarbonate-piperidine-2,5'(6'H)-[4H-1,2]-oxazine]-3'-carboxylate:

The enamine 21d (8.9 g, 33.17 mmol) is dissolved in THF (80 mL) and stirred at room temperature. The ethyl 3-bromo-2-hydroxyiminopropanoate (7.42 g, 35.16 mmol, 1.06 equiv, ref: Ottenheijm, H. C. J.; Plate, R.; Noordlik, J. H.; Herscheid, J. D. M. *J. Org. Chem.* 1982, 47, 2147.) is added in portions over 15 minutes. The solution warms up during this process. The resulting solution is stirred at room temperature for 30 minutes, and then triethylamine (3.59 g, 35.5 mmol, 1.07 equiv) is added. The reaction mixture is stirred for an additional 2 h. The reaction is quenched with the addition of water (100 mL) and then extracted with ethyl acetate. The organic layers are dried over sodium sulfate, and concentrated under reduced pressure to an oil.. Purification is accomplished by chromatography on silica gel using hexane: ethyl acetate (3:1) as the eluent to obtain a clear oil. MS (ESI): 396 (M$^+$+H).

21 f. Ethyl 8N-t-butyldicarbonate-1,8-diazobicyclo-[4.5.0]-decane-2-carboxylate:

The oxazine 21e (2.033 g, 5.14 mmol) is dissolved in ethanol (100 mL) in a Parr bottle followed by the addition of Raney nickel (wet) (2.0g, weight equiv). The Parr bottle is then placed on the hydrogenator under a hydrogen atmosphere (40 psi) for 5 hours, the hydrogen was refilled several times. The Raney nickel was then filtered through celite, and the resulting mixture was concentrated under reduced pressure. MS (ESI): 313 (M$^+$+H)

21g. Ethyl 1N-[(4-methoxyphenyl)sulfonyl]-SN-1-butyldicarbonate-1,8-diazobicyclo-[4.5.0]-decane-2-carboxylate:

The ethyl ester 21f (1.7 g, 5.48 mmol) is dissolved in pdioxane:water (1:1, 100 mL) and then 4-methoxyphenylsulfonyl chloride (1.36 g, 6.6 mmol) and triethylamine (1.66 g, 16.44 mmol) are added. The reaction mixture is stirred overnight. The reaction is quenched and acidified with 1 N HCl, diluted with water and extracted with methylene chloride. The organic extracts are dried over sodium sulfate, and concentrated under reduced pressure. Purification is accomplished by chromatography on silica gel using hexane: ethyl acetate (3:1). MS (ESI): 483 (M$^+$+H), 500 (M$^+$+NH$_4$).

21 h. 1N-[(4-methoxyphenyl)sulfonyl]-8N-t-butyldicarbonate-1,8-diazobicyclo-[4.5.0]-decane-2-carboxylic acid:

The ethyl ester 21g (1.0 g, 2.07 mmol) was dissolved in methanol (10 mL) and THF (5 mL). A solution of lithium hydroxide (1.5 g, excess) in water (5 mL) was then added and the resulting mixture is stirred for 1 hour. The reaction mixture was then quenched and acidified with 1 N HCl. The reaction mixture is extracted with methylene chloride and water. The organic layers are dried over sodium sulfate and concentrated under reduced pressure to give the product. MS (ESI): 455 (M$^+$+H), 472 (M$^+$+NH$_4$).

21i. N-Hydroxy-1 N-[(4-methoxyphenyl)sulfonyl]-8N-t-butyldicarbonate-1,8-diazobicyclo-[4.5.0]-decane-2-carboxamide:

The carboxylic acid 21h (0.92 g, 2.02 mmol) was dissolved in methylene chloride (20 mL) and then oxalyl chloride (0.525 g, 4.14 mmol) and DMF (0.148 g, 1.0 mmol) were added under a nitrogen atmosphere. In a separate flask, hydroxylamine hydrochloride (0.56 g, 8.08 mmol) was dissolved in water (5 mL), followed by the addition of THF (15 mL). The reaction was cooled down in an ice bath and triethyl amine (1.22 mL, 12.12 mmol) was added. The acid mixture is then added to the hydroxyl amine solution at 0° C. The reaction mixture is then warmed to room temperature and stirred for 1 h. To neutralize the solution, 1 N HCl is added reach a pH 5. The mixture is then extracted with methylene chloride and water. The organic layers were dried over sodium sulfate and concentrated under reduced pressure. Chromatography was performed on reverse phase HPLC (Waters Symmetry $C_{18}$) using a solvent system of 50% A (95% water, 5% acetonitrile, 0.1 % formic acid) and 50% B (20% water, 80% water). MS (ESI): 470 ($M^++H$), 487 ($M^++NH_4$).

EXAMPLE 22

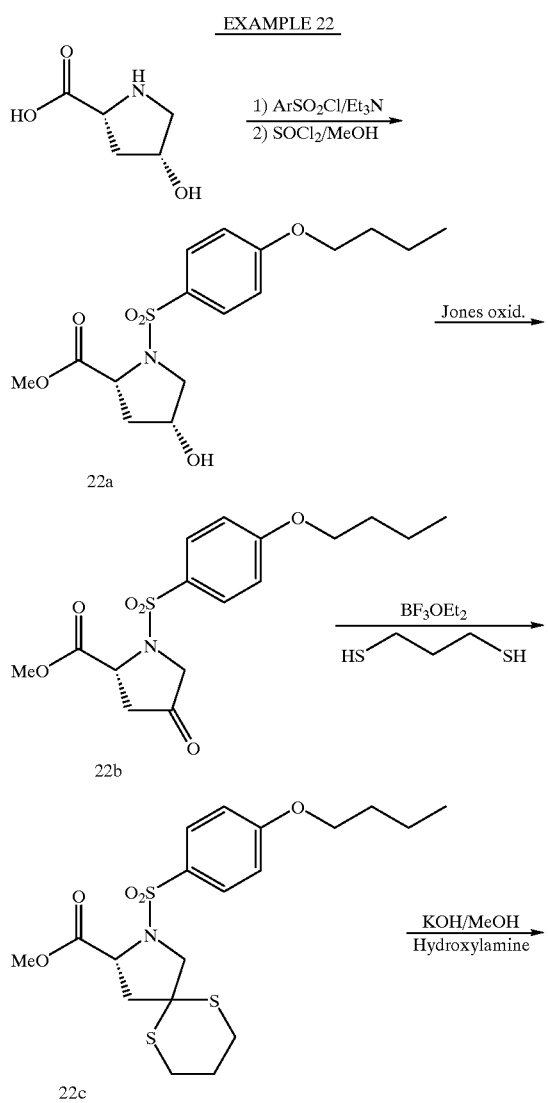

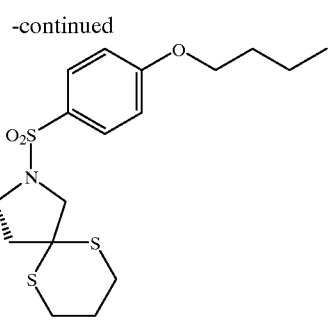

22d

22a. Methyl 1N-(4-n-butoxyphenylsulfonyl-(4R)-hydroxy-pyrrolidine-(2R)-carboxylate:

cis-4-Hydroxy-D-proline (14.8 g, 112.95 mmol) is mixed with water : dioxane (1:1, 90 mL), triethylamine (39.3 mL, 282 mmol) and N-dimethylaminopyridine (1.3 g, 11.3 mmol). The 4-(n-butoxy) phenylsulfonyl chloride (29.5 g, 118.6 mmol) is added and the mixture is stirred for 14 hr. at room temperature. The mixture is then concentrated and diluted with EtOAc and 1 N HCl. The layers are separated and the organic layer is washed twice with 1 N HCl, once with brine, dried over $MgSO_4$, filtered and evaporated to give 37.4 g of solid material which is dissolved in MeOH (200 mL). Thionyl chloride (20 mL, 272 mmol) is added dropwise and the resulting mixture is stirred for 14 hr. The mixture is then evaporated to dryness to give a white solid which is sufficiently pure to carry forward without purification. Ion spray MS: m/z 375 ($M^++NH_4$), 358.3 ($M^++H$).

22b. Methyl 1N-(4-butoxyphenylsulfonyl)4oxo-pyrrolidine-2)-carboxylate:

A 8 N solution of Jones reagent is prepared (Oxidations in Organic Chemistry, P273). The alcohol 22a (40 g, 112 mmol) is dissolved in 300 mL of acetone and cooled to 0 ° C. Jones reagent is added (120 mL, 960 mmol) (color changed from orange-red to green) and the mixture is stirred at room temperature for 14 h. The reaction mixture is diluted with water and extracted three times with EtOAc. The organic layers are washed three times with water and once with sodium chloride, dried over magnesium sulfate, and evaporated. The product is crystallized from EtOAc to give the desired product as a solid. Ion spray MS: m/z 378.3 ($M^++Na$), 356.3 ($M^++H$).

22c. Methyl 8N-(4-butoxyphenylsulfonyl)-1,5-dithia-8-azaspiro[5,4]decane-9(R)-carboxylate:

The ketone 22b (1.5 g, 4.22 mmol) is dissolved in 30 mL of anhydrous dichloromethane and then 1,3-propane dithiol (0.84 mL, 8.45 mmol) and borane trifluoride etherate (0.42 mL, 3.98 mmol) are added. The mixture is stirred at room temperature overnight. The solution is made basic by the addition of 1 N sodium hydroxide and then the mixture is extracted three times with EtOAc. The organic layers are washed with water and ammonium chloride, dried over magnesium sulfate, filtered and evaporated to give the title compound as an oil. Ion spray MS: m/z 463 ($M^++NH_4$), 446 ($M^++H$).

22d. N-Hydroxy-8N-(4-n-butoxypheny isulfonyl)-1,5-dithia-8-azaspiro[5,4]decane-9(R)-carboxamide:

A 1.5 M solution of potassium hydroxylamine in methanol is prepared as described in Fieser and Fieser, Vol 1, p 478. The 1.5 M solution (10 mL, 14.3 mmol) is added directly to the methyl ester 22c (0.8 g, 1.8 mmol) and the reaction mixture is stirred overnight. The solution is acidified with 1 N HCl, then the mixture is extracted three times with ethyl acetate, dried with magnesium sulfate, filtered and evaporated. The product is purified by reverse phase prep HPLC (40A60B, A, 95% $H_2O$, 5% acetonitrile, 0.1% formic acid; B, 80% acetonitrile, 20% $H_2O$; 19×300 mm waters SymmetryPrep $C_{18}$ column) to give the title compound as a white foaming solid. Ion spray MS: m/z 464 ($M^+$+$NH_4$),447 ($M^+$+H).

A 1.5 M solution of potassium hydroxylamine in methanol is prepared as described in Fieser and Fieser, Vol 1, p 478. The 1.5 M solution (15 mL, 22.5 mmol) is added directly to the methyl ester 23a (0.8 g, 1.9 mmol) and the reaction mixture is stirred overnight. The solution is acidified with 1 N HCl, then the mixture is extracted three times with ethyl acetate, dried with magnesium sulfate, filtered and evaporated. The product is purified by reverse phase prep HPLC (40A60B, A, 95% $H_2O$, 5% acetonitrile, 0.1% formic acid; B, 80% acetonitrile, 20% $H_2O$; 19×300 mm waters SymmetryPrep $C_{18}$ column) to give the title compound as a white foaming solid. Ion spray MS: m/z 432 ($M^+$+$NH_4$), 415 ($M^+$+H).

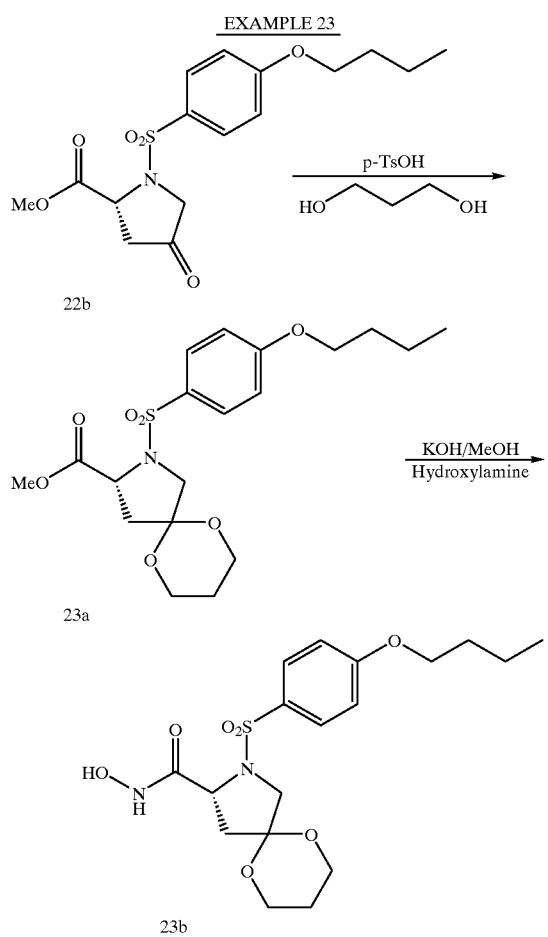

EXAMPLE 23

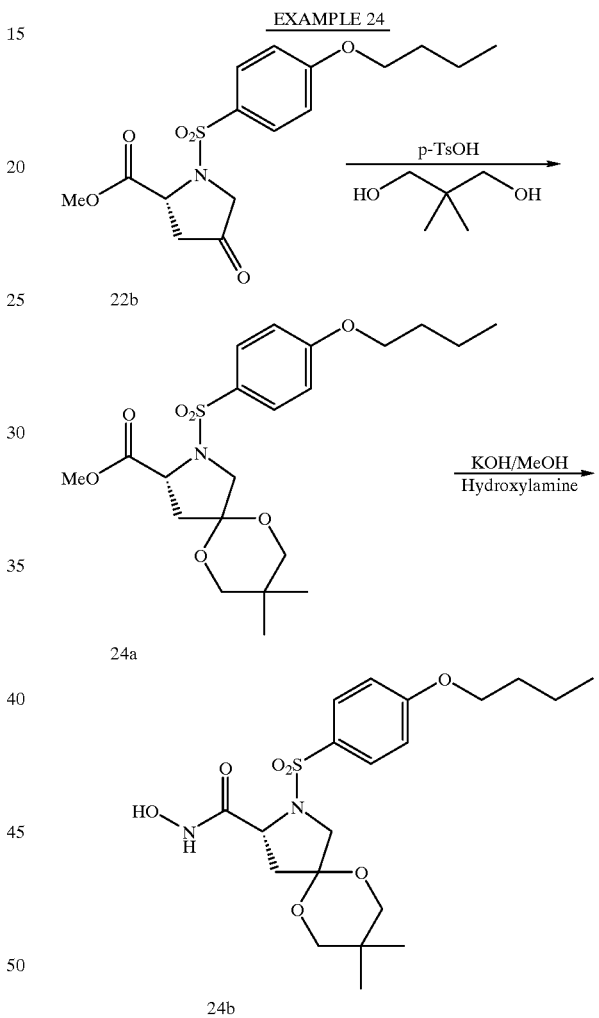

EXAMPLE 24

23a. Methyl 8N-(4-butoxyphenylsulfonyl)-1,5-dioxo-8-azaspiro[5,4]decane-9(R)-carboxylate:

The ketone 22b (1.5 g, 4.22 mmol) is dissolved in 40 mL of benzene, and then 1,3-propane diol (0.32 g, 4.22 mmol) and p-toluenesulfonic acid monohydrate (8 mg, 0.042 mmol) are added. The mixture is refluxed using Dean and Stark apparatus overnight. The solution is made basic by the addition of aqueous $NaHCO_3$ and then extracted three times with $Et_2O$. The organic layers are washed with ammonium chloride, dried over magnesium sulfate, filtered and evaporated. Purification of the product is accomplished by chromatography on silica gel with hexane/EtOAc (4:1) to afford the desired product. Ion spray MS: m/z 431 ($M^+$+$NH_4$), 414 ($M^+$+H).

23b. N-Hydroxy-8N-(4-n-butoxyphenyisulfonyl)-1,5dioxo-8-azaspiro[5,4]decane-9(R)-carboxamide:

24a. Methyl 8N-(4-butoxyphenylsulfonyl)-1,5-dioxo-3,3-dimethyl-8-azaspiro[5,4]decane-9(R)-carboxylate:

The ketone 22b (1.5 g, 4.22 mmol) is dissolved in 40 mL of toluene, and then neopentyl glycol (0.44 g, 4.22 mmol) and p-toluenesulfonic acid monohydrate (8 mg, 0.042 mmol) are added. The mixture is refluxed using a Dean-Stark apparatus overnight. The solution is made basic by the addition of aqueous $NaHCO_3$ and then extracted three times with $Et_2O$. The organic layers are washed with ammonium chloride, dried over magnesium sulfate, filtered and evaporated. Purification of the product is accomplished by chromatography on silica gel with hexane/EtOAc (7:3) to afford the desired product. Ion spray MS: m/z 459 ($M^+$+$NH_4$), 442 ($M^+$+H).

24b. N-Hydroxy-8N-(4-n-butoxyphenylsulfonyl)-1,5-dioxo-3,3-dimethyl-8-azaspiro[5,4]decane-9(R)-carboxamide:

A 1.5 M solution of potassium hydroxylamine in methanol is prepared as described in Fieser and Fieser, Vol 1, p478. The 1.5 M solution (12 mL, 18.1 mmol) is added directly to the methyl ester 24a (1.0 g, 2.27 mmol) and the reaction mixture is stirred overnight. The solution is acidified with 1 N HCl, then the mixture is extracted three times with ethyl acetate, dried with magnesium sulfate, filtered and evaporated. The crude product is purified by flash chromatography ($CH_2Cl_2$/EtOAc, 1:1) on silica gel to give the title compound as a white foaming solid. Ion spray MS: m/z 460 ($M^+$+$NH_4$), 443 ($M^+$+H).

EXAMPLE 25

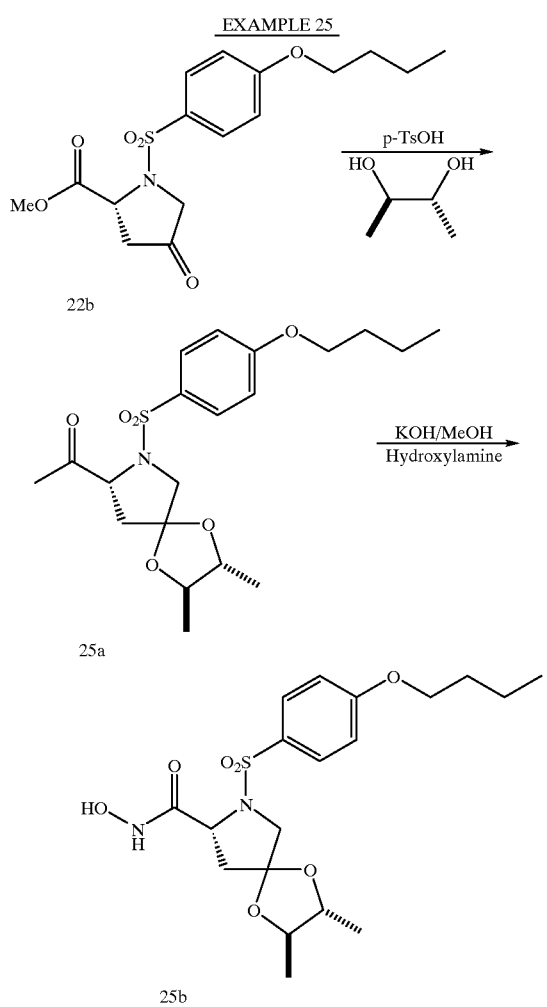

25a. Methyl 7N-(4-butoxyphenylsulfonyl)-1,4-dioxo-(2R)methyl-(3R)-methyl-7-azaspiro[4,4]nonane-8(R)-carboxylate:

The ketone 22b (1.5 g, 4.2 mmol) is dissolved in 40 mL of benzene, and then (2R,3R)-(-)-2,3-butanediol (0.46 g, 5.07 mmol) and p-toluenesulfonic acid monohydrate (80 mg, 0.42 mmol) are added. The mixture is refluxed using a Dean-Stark apparatus overnight. The solution is made basic by the addition of aqueous $NaHCO_3$ and then extracted three times with $Et_2O$. The organic layers are washed with ammonium chloride, dried over magnesium sulfate, filtered and evaporated to afford the desired product. Ion spray MS: m/z 445 ($M^+$+$NH_4$), 428($M^+$+H).

25b. N-Hydroxy 7N-(4-butoxyphenylsulfonyl)-1,4-dioxo-(2R)methyl-(3R)methyl-7-azaspiro[4,4]nonane-8(R)-carboxamide: A 1.5 M solution of potassium hydroxylamine in methanol is prepared as described in Fieser and Fieser, Vol 1, p 478. The 1.5 M solution (15 mL, 26 mmol) is added directly to the methyl ester 25a (1.4 g, 3.28 mmol) and the reaction mixture is stirred overnight. The solution is acidified with 1 N HCl, then the mixture is extracted three times with ethyl acetate, dried with magnesium sulfate, filtered and evaporated. The product is purified by flash chromatography ($CH_2Cl_2$/$CH_3OH$, 95:5) on silica gel to give the title compound as a white foaming solid. Ion spray MS: m/z 451 ($M^+$+Na), 429 ($M^+$+H).

EXAMPLE 26

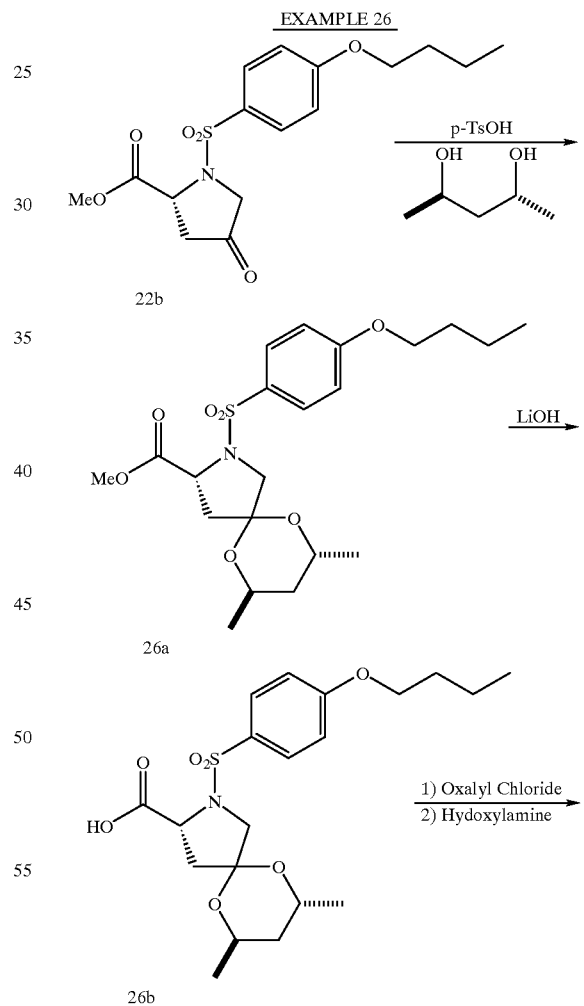

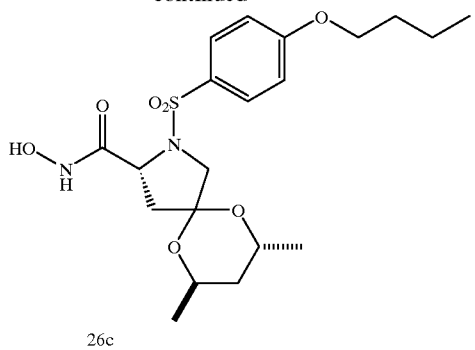

26c

26a. Methyl 1N-[(4-butoxyphenyl)sulfonyl]-1,5-dioxa-azaspiro[4.5]nonane-2R,4R-dimethyl-2-carboxylate:

The ketone 22b (1.0 g, 2.82 mmol) is dissolved in benzene (60 mL) and then 2R,4R-(+)-Pentanediol (0.44g, 4.22 mmol) and p-toluene sulfonic acid (0.01 equiv) are added. The reaction is equipped with a Dean-Stark trap and a reflux condenser under a nitrogen atmosphere. The reaction is heated to reflux overnight. The reaction mixture is quenched and basified with saturated sodium bicarbonate. The resulting mixture is then extracted with ethyl acetate and water and the organic layers are dried over sodium sulfate and concentrated under reduced pressure. Purification is performed by chromatography on silica gel using hexane: ethyl acetate (7:3) as the eluent. MS (ESI): 442 ($M^+$+H), 459 ($M^+$+$NH_4$).

26b. 1N-[(4butoxyphenyl)sulfonyl]-1,5-dioxa-azaspiro[4.5]nonane-2R,4R-dimethyl-2-carboxylic acid:

The ketal 26a (0.7 g, 1.56 mmol) is dissolved in methanol (10 mL) and THF (5 mL) and then lithium hydroxide (1.0 g, excess) in water (5 mL) is added. The reaction mixture is stirred for 1 hour and then quenched and acidified with 1 N HCl to achieve a pH of 2. The reaction mixture is then extracted with methylene chloride and water. The organic layers are dried over sodium sulfate and concentrated under reduced pressure to give the product. MS (ESI): 428 ($M^+$+H), 445 ($M^+$+$NH_4$).

26c. N-Hydroxy-1 N-[(4butoxyphenyl)sulfonyl]-1,5dioxa-azaspiro[4.5]nonane-2R,4R-dimethyl-2-carboxamide:

The carboxylic acid 26b (0.60 g, 1.4 mmol) is dissolved in methylene chloride (15 mL), followed by the addition of oxalyl chloride (0.36 g, 2.87 mmol) and DMF (0.102 g, 1.4 mmol) under a nitrogen atmosphere. In a separate flask, the hydroxylamine hydrochloride (0.39 g, 5.2 mmol) is dissolved in water (3 mL), followed by the addition of THF (10 mL). The amine solution is cooled in an ice bath and triethylamine (1.16 mL, 8.4 mmol) is added. The acid mixture is then added to the hydroxylamine solution at 0° C. The reaction mixture is warmed to room temperature and stirred for 1 h. To neutralize the solution, 1 N HCl is added to achieve pH=5. The solution is then extracted with methylene chloride and water. The organic layers are dried over sodium sulfate and concentrated under reduced pressure. Purification is accomplished by reverse phase chromatography (Waters Symmetry $C_{18}$) using a solvent system of 40% A (95% water, 5% acetonitrile, 0.1% formic acid) and 60% B (20% water, 80% water). MS (ESI): 443 ($M^+$+H)

The following chart shows the structure of further examples 27–116 described below:

EXAMPLES 27–116

The following (where W is nil) compounds are made using the methods described and exemplified above.

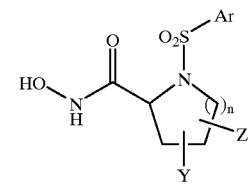

|  | Z | Y | Ar | n |
|---|---|---|---|---|
| Example 27 | 4-(—$SCH_2CH_2CH_2S$—) | 3,3-$(CH_3)_2$ | 4-(MeO)—$C_6H_4$— | 1 |
| Example 28 | 4-(—$SCH_2CH_2CH_2S$—) | H | 4-Br—$C_6H_4$— | 1 |
| Example 29 | 4-(—$SCH_2CH_2CH_2S$—) | H | 4-(4-$C_5H_4$n)O—$C_6H_4$— | 1 |
| Example 30 | 4-(—$SCH_2CH_2S$—) | H | 4-(4-$C_5H_4$n)O—$C_6H_4$— | 1 |
| Example 31 | 4-(—$OCH_2CH_2O$—) | H | 4-$NO_2$—$C_6H_4$— | 1 |
| Example 32 | 4-(—$OCH_2CH_2O$—) | H | 4-i-BuO—$C_6H_4$— | 1 |
| Example 33 | 4-(—$OCH_2CH_2O$—) | H | 4-($C_6H_5$)O—$C_6H_4$— | 1 |
| Example 34 | 4-(—$OCH_2CH_2O$—) | H | 4-(4-F—$C_6H_4$)O—$C_6H_4$— | 1 |
| Example 35 | 4-(—$OCH_2CH_2O$—) | H | 4-(4-Cl—$C_6H_4$)O—$C_6H_4$— | 1 |
| Example 36 | 4-(—$OCH_2CH_2O$—) | H | 4-(4-Br—$C_6H_4$)O—$C_6H_4$— | 1 |
| Example 37 | 4-(—$OCH_2CH_2O$—) | H | 4-(4-Me—$C_6H_4$)O—$C_6H_4$— | 1 |
| Example 38 | 4-(—$OCH_2CH_2O$—) | H | 4-(4-MeO—$C_6H_4$)O—$C_6H_4$— | 1 |
| Example 39 | 4-(—$OCH_2CH_2O$—) | H | 4-(4-CN—$C_6H_4$)O—$C_6H_4$— | 1 |
| Example 40 | 4-(—$OCH_2CH_2O$—) | H | 4-(4-$Me_2$N—$C_6H_4$)O—$C_6H_4$— | 1 |
| Example 41 | 4-(—$OCH_2CH_2O$—) | H | 4-EtO—$C_6H_4$— | 1 |
| Example 42 | 4-(—$OCH_2CH_2O$—) | H | 4-i-PrO—$C_6H_4$— | 1 |
| Example 43 | 4-(—$OCH_2CH_2O$—) | H | 4-n-PrO—$C_6H_4$— | 1 |
| Example 44 | 4-(—$OCH_2CH_2O$—) | H | 4-Br—$C_6H_4$— | 1 |
| Example 45 | 4-(—$OCH_2CH_2O$—) | H | 2-$CH_3$—4-Br—$C_6H_3$— | 1 |
| Example 46 | 4-(—$OCH_2CH_2O$—) | H | 4-$C_6H_5$—$C_6H_4$— | 1 |
| Example 47 | 4-(—$OCH_2CH_2O$—) | H | 4-(4-F—$C_6H_5$)—$C_6H_4$— | 1 |
| Example 48 | 4-(—$OCH_2CH_2O$—) | H | 4-(4-Cl—$C_6H_5$)—$C_6H_4$— | 1 |
| Example 49 | 4-(—$OCH_2CH_2O$—) | H | 4-(4-Br—$C_6H_5$)—$C_6H_4$— | 1 |
| Example 50 | 4-(—$OCH_2CH_2O$—) | H | 4-(4-$Me_2$N—$C_6H_4$)—$C_6H_4$— | 1 |
| Example 51 | 4-(—$OCH_2CH_2O$—) | H | 4-(4-CN—$C_6H_4$)—$C_6H_4$— | 1 |
| Example 52 | 4-(—$OCH_2CH_2O$—) | H | 4-(4-MeO—$C_6H_4$)—$C_6H_4$— | 1 |
| Example 53 | 4-(—$OCH_2CH_2O$—) | H | 4-(4-$C_5H_4$N)O—$C_6H_4$— | 1 |
| Example 54 | 4-(—$OCH_2CH_2O$—) | H | 4-(3-$C_5H_4$N)O—$C_6H_4$— | 1 |
| Example 55 | 4-(—$OCH_2CH_2O$—) | H | 4-(2-$C_5H_4$N)O—$C_6H_4$— | 1 |

-continued

| | Z | Y | Ar | n |
|---|---|---|---|---|
| Example 56 | 4-(—OCH$_2$CH$_2$O—) | H | C$_6$H$_5$CH$_2$CH$_2$— | 1 |
| Example 57 | 4-(—OCH$_2$CH$_2$O—) | H | C$_6$H$_5$CH$_2$— | 1 |
| Example 58 | 4-(—OCH$_2$CH$_2$O—) | H | (4-C$_5$H$_4$N)CH$_2$CH$_2$— | 1 |
| Example 59 | 4-(—OCH$_2$CH$_2$O—) | H | (2-C$_5$H$_4$N)CH$_2$CH$_2$— | 1 |
| Example 60 | 4-(—OCH$_2$CH$_2$O—) | H | 4-(C$_6$H$_{11}$)O—C$_6$H$_4$— | 1 |
| Example 61 | 4-(—OCH$_2$CH$_2$O—) | H | 4-(C$_5$H$_{11}$)O—C$_6$H$_4$— | 1 |
| Example 62 | 4-(—OCH$_2$CH$_2$O—) | H | 4-(C$_6$H$_{13}$O)—C$_6$H$_4$— | 1 |
| Example 63 | 4-(—OCH$_2$CH$_2$O—) | H | 4-(CH$_3$OCH$_2$CH$_2$)O—C$_6$H$_4$— | 1 |
| Example 64 | 4-(—OCH$_2$CH$_2$O—) | H | 5-(2-pyridinyl)-2-thienyl- | 1 |
| Example 65 | 4-(—OCH$_2$CH$_2$O—) | H | 5-(3-isoxazolyl)-2-thienyl- | 1 |
| Example 66 | 4-(—OCH$_2$CH$_2$O—) | H | 5-(2-(methylthio)pyrimidin-4-yl)-2-thienyl- | 1 |
| Example 67 | 4-(—OCH$_2$CH$_2$O—) | H | 5-(3-(1-methyl-5-(trifluoromethyl)pyrazolyl)-2-thienyl- | 1 |
| Example 68 | 4-(—OCH$_2$CH$_2$CH$_2$O—) | H | 4-(C$_6$H$_5$)O—C$_6$H$_4$— | 1 |
| Example 69 | 4-(—OCH$_2$CH$_2$CH$_2$O—) | H | 4-(4-F—C$_6$H$_4$)O—C$_6$H$_4$— | 1 |
| Example 70 | 4-(—OCH$_2$CH$_2$CH$_2$O—) | H | 4-(4-Cl—C$_6$H$_4$)O—C$_6$H$_4$— | 1 |
| Example 71 | 4-(—OCH$_2$CH$_2$CH$_2$O—) | H | 4-(4-Br—C$_6$H$_4$)O—C$_6$H$_4$— | 1 |
| Example 72 | 4-(—OCH$_2$CH$_2$CH$_2$O—) | H | 4-(4-Me—C$_6$H$_4$)O—C$_6$H$_4$— | 1 |
| Example 73 | 4-(—OCH$_2$CH$_2$CH$_2$O—) | H | 4-(4-MeO—C$_6$H$_4$)O—C$_6$H$_4$— | 1 |
| Example 74 | 4-(—OCH$_2$CH$_2$CH$_2$O—) | H | 4-(4-CN—C$_6$H$_4$)O—C$_6$H$_4$— | 1 |
| Example 75 | 4-(—OCH$_2$CH$_2$CH$_2$O—) | H | 4-(4-Me$_2$N—C$_6$H$_4$)O—C$_6$H$_4$— | 1 |
| Example 76 | 4-(—OCH$_2$CH$_2$CH$_2$O—) | H | 4-EtO—C$_6$H$_4$— | 1 |
| Example 77 | 4-(—OCH$_2$CH$_2$CH$_2$O—) | H | 4-i-Pro—C$_6$H$_4$— | 1 |
| Example 78 | 4-(—OCH$_2$CH$_2$CH$_2$O—) | H | 4-n-Pro—C$_6$H$_4$— | 1 |
| Example 79 | 4-(—OCH$_2$CH$_2$CH$_2$O—) | H | 4-Br—C$_6$H$_4$— | 1 |
| Example 80 | 4-(—OCH$_2$CH$_2$CH$_2$O—) | H | 2-CH$_3$-4-Br—C$_6$H$_3$— | 1 |
| Example 81 | 4-(—OCH$_2$CH$_2$CH$_2$O—) | H | 4-C$_6$H$_5$—C$_6$H$_4$— | 1 |
| Example 82 | 4-(—OCH$_2$CH$_2$CH$_2$O—) | H | 4-(4-F—C$_6$H$_5$)—C$_6$H$_4$— | 1 |
| Example 83 | 4-(—OCH$_2$CH$_2$CH$_2$O—) | H | 4-(4-Cl—C$_6$H$_5$)—C$_6$H$_4$— | 1 |
| Example 84 | 4-(—OCH$_2$CH$_2$CH$_2$O—) | H | 4-(4-Br—C$_6$H$_5$)—C$_6$H$_4$— | 1 |
| Example 85 | 4-(—OCH$_2$CH$_2$CH$_2$O—) | H | 4-(4-Me$_2$N—C$_6$H$_4$)—C$_6$H$_4$— | 1 |
| Example 86 | 4-(—OCH$_2$CH$_2$CH$_2$O—) | H | 4-(4-CN—C$_6$H$_4$)—C$_6$H$_4$— | 1 |
| Example 87 | 4-(—OCH$_2$CH$_2$CH$_2$O—) | H | 4-(4-MeO—C$_6$H$_4$)—C$_6$H$_4$— | 1 |
| Example 88 | 4-(—OCH$_2$CH$_2$CH$_2$O—) | H | 4-i-BuO—C$_6$H$_4$— | 1 |
| Example 89 | 4-(—OCH$_2$CH$_2$CH$_2$O—) | H | 4-(4-C$_5$H$_4$N)O—C$_6$H$_4$— | 1 |
| Example 90 | 4-(—OCH$_2$CH$_2$CH$_2$O—) | H | 4-(3-C$_5$H$_4$N)O—C$_6$H$_4$— | 1 |
| Example 91 | 4-(—OCH$_2$CH$_2$CH$_2$O—) | H | 4-(2-C$_5$H$_4$N)O—C$_6$H$_4$— | 1 |
| Example 92 | 4-(—OCH$_2$CH$_2$CH$_2$O—) | H | C$_6$H$_5$CH$_2$CH$_2$— | 1 |
| Example 93 | 4-(—OCH$_2$CH$_2$CH$_2$O—) | H | C$_6$H$_5$CH$_2$— | 1 |
| Example 94 | 4-(—OCH$_2$CH$_2$CH$_2$O—) | H | (4-C$_5$H$_4$n)CH$_2$CH$_2$— | 1 |
| Example 95 | 4-(—OCH$_2$CH$_2$CH$_2$O—) | H | (2-C$_5$H$_4$n)CH$_2$CH$_2$— | 1 |
| Example 96 | 4-(—OCH$_2$CH$_2$CH$_2$O—) | H | 4-(C$_6$H$_{11}$)O—C$_6$H$_4$— | 1 |
| Example 97 | 4-(—OCH$_2$CH$_2$CH$_2$O—) | H | 4-(C$_5$H$_{11}$)O—C$_6$H$_4$— | 1 |
| Example 98 | 4-(—OCH$_2$CH$_2$CH$_2$O—) | H | 4-(C$_6$H$_{13}$)O—C$_6$H$_4$— | 1 |
| Example 99 | 4-(—OCH$_2$CH$_2$CH$_2$O—) | H | 4-(CH$_3$OCH$_2$CH$_2$)O—C$_6$H$_4$— | 1 |
| Example 100 | 4-(—OCH$_2$CH$_2$CH$_2$O—) | H | 4-(MeO)—C$_6$H$_4$— | 2 |
| Example 101 | 4(—SCH$_2$CH$_2$S—) | H | 4-(MeO)—C$_6$H$_4$— | 2 |
| Example 102 | 4(—SCH$_2$CH$_2$CH$_2$S—) | H | 4-(MeO)—C$_6$H$_4$— | 2 |
| Example 103 | 3(—OCH$_2$CH$_2$O—) | H | 4-(MeO)—C$_6$H$_4$— | 2 |
| Example 104 | 3(—SCH$_2$CH$_2$CH$_2$S—) | H | 4-(MeO)—C$_6$H$_4$— | 2 |
| Example 105 | 3(—SCH$_2$CH$_2$CH$_2$S—) | H | 4-(n-BuO)—C$_6$H$_4$— | 2 |
| Example 106 | 4-(—CH$_2$CH$_2$CH$_2$CH$_2$—) | H | 4-(MeO)—C$_6$H$_4$— | 1 |
| Example 107 | 4-(—CH$_2$CH$_2$CH$_2$CH$_2$—) | H | 4-(4-Me$_2$N—C$_6$H$_4$)—C$_6$H$_4$— | 1 |
| Example 108 | 4-(—CH$_2$CH$_2$CH$_2$CH$_2$—) | H | 4-(4-F—C$_6$H$_5$)—C$_6$H$_4$— | 1 |
| Example 109 | 4-(—CH$_2$CH$_2$CH$_2$CH$_2$—) | H | (4-C$_5$H$_4$N)CH$_2$CH$_2$— | 1 |
| Example 110 | 4-(—CH$_2$CH$_2$CH$_2$CH$_2$—) | H | 4-(4-C$_5$H$_4$NO)—C$_6$H$_4$— | 1 |
| Example 111 | 4-(—CH$_2$CH$_2$CH$_2$CH$_2$—) | 5-CH$_3$ | 4-(MeO)—C$_6$H$_4$— | 1 |
| Example 112 | 4-(—CH$_2$CH$_2$CH$_2$CH$_2$CH$_2$—) | H | 4-(n-BuO)—C$_6$H$_4$— | 1 |
| Example 112 | 4-(—CH$_2$CH$_2$N(Me)CH$_2$CH$_2$—) | H | 4-(MeO)—C$_6$H$_4$— | 1 |
| Example 114 | 4-(—C(O)NHC(O)NH—) | H | 4-(MeO)—C$_6$H$_4$— | 1 |

-continued

| | Z | Y | Ar | n |
|---|---|---|---|---|
| Example 115 | 4-(—CH$_2$NHC(O)CH$_2$—) | H | 4-(MeO)—C$_6$H$_4$— | 1 |
| Example 116 | 4-(—CH$_2$NBnC(O)CH$_2$—) | H | 4-(MeO)—C$_6$H$_4$— | 1 |

Methods

Example 27 is prepared by acetal formation with the appropriately functionalized hydroxy-proline derivative described by Raman Sharma and William D. Lubell in *J. Org. Chem.* 1996, 61,202. Examples 28–99 are prepared by acetal formation with the appropriately functionalized hydroxy proline derivative which is prepared in a manner analagous to example 1. The sulfonyl chlorides which are used to prepare the above examples are either purchased from commercial sources or prepared via known methods. For example, the 4-phenoxyphenylsulfonyl chloride used for the preparation of Example 17, was prepared as described by R. J. Cremlyn et al in *Aust. J. Chem.,* 1979, 32,445.52.

Examples 100–102 are prepared by acetal formation, reduction and/or nucleophillic substitution of the appropriately functionalized 4-ketopipecolic acid described by J.-P. Obrecht et al in *Organic Synthesis* 1992, 200.

Examples 103–105 are prepared by acetal formation, reduction and/or nucleophillic substitution of the appropriately functionalized 5-ketopipecolic acid described by M. E-Freed and A. R. Day in *J. Org. Chem.* 1960, 2, 2105 or the properly functionalized 3-ketopipecolic acid described by J. Bosch et al in *Tetrahedron* 1984, 40, 2505.

Examples 106–113 are prepared by cyclization, reduction and/or nucleophilic substitution of the appropriately functionalized enamine as described by R. Henning et al in *Synthesis,* 1989, 265 and further manipulated as described for example 5.

Example 114 (the spirohydantoin) is prepared from the appropriately substituted ketone (Ib) and potassium cyanide and ammonium carbonate as described by Smith et al, *J. Med Chem.* 1995, 38, 3772.

Example 115–116 are prepared from the appropriately substituted ketone (Ib) by Wittig reaction and subsequent Michael addition of nitromethane as described by Smith et al, *J. Med Chem.* 1995, 38, 3772. Subsequent reduction and nucleophilic substitution provides the desired compounds.

These examples provide the skilled artisan with sufficient guidance as to making the present invention and do not limit it in any way.

Composition and Method of Use Examples

The compounds of the invention are useful to prepare compositions for the treatment of ailments and the like. The following composition and method examples do not limit the invention, but provide guidance to the skilled artisan to prepare and use the compounds, compositions and methods of the invention. In each case the compounds formula I may be substituted for the example compound shown below with similar results.

The methods of use exemplified do not limit the invention, but provide guidance to the skilled artisan to use the compounds, compositions and methods of the invention. The skilled practitioner will appreciate that the examples provide guidance and may be varied based on condition and the patient.

Example A

A tablet composition for oral administration, according to the present invention, is made comprising:

| Component | Amount |
|---|---|
| Example 9 | 15. mg |
| Lactose | 120. mg |
| Maize Starch | 70. mg |
| Talc | 4. mg |
| Magnesium Stearate | 1. mg |

Other compounds having a structure according to Formula (I) are used with substantially similar results.

A human female subject weighing 60 kg (132 lbs), suffering from rheumatoid arthritis, is treated by a method of this invention. Specifically, for 2 years, a regimen of three tablets per day is administered orally to said subject.

At the end of the treatment period, the patient is examined and is found to have reduced inflammation, and improved mobility without concomitant pain.

Example B

A capsule for oral administration, according to the present invention, is made comprising:

| Component | Amount (% w/w) |
|---|---|
| Example 3 | 15% |
| Polyethylene glycol | 85% |

Other compounds having a structure according to Formula (I) are used with substantially similar results.

A human male subject weighing 90 kg (198 lbs), suffering from osteoarthritis, is treated by a method of this invention. Specifically, for 5 years, a capsule containing 70 mg of Example 3 is administered daily to said subject.

At the end of the treatment period, the patient is examined via orthoscopy, and found to have no further advancement of erosion/fibrillation of the articular cartilage.

Example C

A saline-based composition for local administration, according to the present invention, is made comprising:

| Component | Amount (% w/w) |
|---|---|
| Example 13 | 5% |
| Polyvinyl alcohol | 15% |
| Saline | 80% |

Other compounds having a structure according to Formula (I) are used with substantially similar results.

A patient having deep corneal abrasion applies the drop to each eye twice a day. Healing is speeded, with no visual sequelae.

Example D

An topical composition for local administration, according to the present invention, is made comprising:

| Component | Composition (% w/v) |
|---|---|
| Compound of Example 3 | 0.20 |
| Benzalkonium chloride | 0.02 |
| Thimerosal | 0.002 |
| d-Sorbitol | 5.00 |
| Glycine | 0.35 |
| Aromatics | 0.075 |
| Purified water | q.s |
| Total = | 100.00 |
| Total = | 100.00 |

Any of the other compounds having a structure according to Formula (I) are used with substantially similar results.

A patient suffering from chemical burns applies the composition at each dressing change (b.i.d.). Scarring is substantially diminished.

Example E

A inhalation aerosol composition, according to the present invention, is made comprising:

| Component | Composition (% w/v) |
|---|---|
| Compound of Example 2 | 5.0 |
| Alcohol | 33.0 |
| Ascorbic acid | 0.1 |
| Menthol | 0.1 |
| Sodium Saccharin | 0.2 |
| Propellant (F12, F114) | q.s. |
| Total = | 100.0 |

Any of the other compounds having a structure according to Formula (I) are used with substantially similar results.

An asthma sufferer sprays 0.01 mL via a pump actuator into the mouth while inhaling. Asthma symptoms are diminished.

Example F

A topical opthalmic composition, according to the present invention, is made comprising:

| Component | Composition (% w/v) |
|---|---|
| Compound of Example 5 | 0.10 |
| Benzalkonium chloride | 0.01 |
| EDTA | 0.05 |
| Hydroxyethylcellulose (NATROSOL M) | 0.50 |
| Sodium metabisulfite | 0.10 |
| Sodium chloride (0.9%) | q.s. |
| Total = | 100.0 |

Any of the other compounds having a structure according to Formula (I) are used with substantially similar results.

A human male subject weighing 90 kg (198 lbs), suffering from corneal ulcerations, is treated by a method of this invention. Specifically, for 2 months, a saline solution containing 10 mg of Example 5 is administered to said subject's affected eye twice-daily.

Example G

A composition for parenteral administration is made comprising:

| Component | Amount |
|---|---|
| Example 4 | 100 mg/ml carrier |
| Carrier: | |
| sodium citrate buffer with (percent by weight of carrier): | |
| lecithin | 0.48% |
| carboxymethylcellulose | 0.53 |
| povidone | 0.50 |
| methyl paraben | 0.11 |
| propyl paraben | 0.011 |

The above ingredients are mixed, forming a suspension. Approximately 2.0 ml of the suspension is administered, via injection, to a human subject with a premetastatic tumor. The injection site juxtaposes the tumor. This dosage is repeated twice daily, for approximately 30 days. After 30 days, symptoms of the disease subside, and dosage is gradually decreased to maintain the patient.

Other compounds having a structure according to Formula I are used with substantially similar results.

Example H

A mouthwash composition is prepared;

| Component | % w/v |
|---|---|
| Example 1 | 3.00 |
| SDA 40 Alcohol | 8.00 |
| Flavor | 0.08 |
| Emulsifier | 0.08 |
| Sodium Fluoride | 0.05 |
| Glycerin | 10.00 |
| Sweetener | 0.02 |
| Benzoic acid | 0.05 |
| Sodium hydroxide | 0.20 |
| Dye | 0.04 |
| Water | balance to 100% |

A patient with gum disease uses I ml of the mouthwash thrice daily to prevent further oral degeneration.

Other compounds having a structure according to Formula I are used with substantially similar results.

Example I

A lozenge composition is prepared;

| Component | % w/v |
|---|---|
| Example 3 | 0.01 |
| Sorbitol | 17.50 |
| Mannitol | 17.50 |
| Starch | 13.60 |
| Sweetener | 1.20 |
| Flavor | 11.70 |
| Color | 0.10 |
| Corn Syrup | balance to 100% |

A patient uses the losenge to prevent loosening of an implant in the maxilla. Other compounds having a structure according to Formula I are used with substantially similar results.

Example J

Chewing Gum Composition

| Chewing Gum Composition | |
|---|---|
| Component | w/v % |
| Example 1 | 0.03 |
| Sorbitol crystals | 38.44 |
| Paloja-T gum base* | 20.00 |
| Sorbitol (70% aqueous solution) | 22.00 |
| Mannitol | 10.00 |
| Glycerine | 7.56 |
| Flavor | 1.00 |

A patient chews the gum to prevent loosening to prevent loosening of dentures.

Other compounds having a structure according to Formula I are used with substantially similar results.

Example K

| Components | w/v % |
|---|---|
| USP Water | 54.656 |
| Methylparaben | 0.05 |
| Propylparaben | 0.01 |
| Xanthan Gum | 0.12 |
| Guar Gum | 0.09 |
| Calcium carbonate | 12.38 |
| Antifoam | 1.27 |
| Sucrose | 15.0 |
| Sorbitol | 11.0 |
| Glycerin | 5.0 |
| Benzyl Alcohol | 0.2 |
| Citric Acid | 0.15 |
| Coolant | 0.00888 |
| Flavor | 0.0645 |
| Colorant | 0.0014 |

Example 1 is prepared by first mixing 80 kg of gylcerin and all of the benzyl alcohol and heating to 65 C, then slowly adding and mixing together methylparaben, propylparaben, water, xanthan gum, and guar gum. Mix these ingredients for about 12 minutes with a Silverson in-line mixer. Then slowly add in the following ingredients in the following order remaining glycerin, sorbitol, antifoam C, calcium carbonate, citric acid, and sucrose. Separately combine flavors and coolants and then slowly add to the other ingredients. Mix for about 40 minutes.

The patient takes the formulation to prevent flare up of colitis.

All references described herein are hereby incorporated by reference.

While particular embodiments of the subject invention have been described, it will be obvious to those skilled in the art that various changes and modifications of the subject invention can be made without departing from the spirit and scope of the invention. It is intended to cover, in the appended claims, all such modifications that are within the scope of this invention.

What is claimed is:

1. A compound having a structure according to Formula (I)

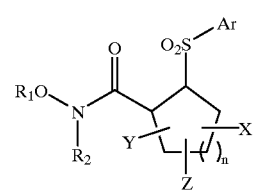

wherein

Ar is allyl, heteroalkyl, aryl or heteroaryl, substituted or unsubstituted;

$R_1$ is H;

$R_2$ is hydrogen, alkyl or acyl;

W is nil or one or more lower alkyl groups, or is an allene, arylene or heteroarylene bridge between two adjacent or nonadjacent carbons (thus forming a fused ring);

Y is independently one or more of hydrogen, hydroxy $SR_3$, $SOR_1$, $SO_2R_5$, alkoxy, amino, wherein amino is of formula $NR_6,R_7$, wherein $R_6$ and $R_7$ arc independently chosen from hydrogen, alkyl, heteroalkyl, heteroaryl aryl, $OR_3$, $SO_2$, $R_8$, $COR_9$, $CSR_{10}$, and $PO(R_{11})_2$; and $R_3$ is hydrogen, alkyl, aryl, or heteroaryl $R_4$ is alkyl, aryl, or heteroaryl;

$R_8$ is chosen from alkyl, aryl, heteroaryl, heteroalkyl, amino, alkylamino, dialkylamino, arylamino, diarylamino and alkylamino;

$R_9$ is chosen from hydrogen, alkoxy, aryloxy, heterurluxy, alkyl, aryl, heteroaryl, heteroalkyl, amino, alkylamitio, dialkylamino, arylamino and alkylarylamino;

$R_{10}$ is chosen from alkyl, aryl, heteroaryl, heteroalkyl, amino, alkylamino, dialkylamino, arylamino, diarylamino and alkylarylamino;

$R_{11}$ is alkyl aryl, heteroaryl, or heteroalkyl;

Z is a spiro group;

n is 1–3;

or an optical isomor, diastersomer or enantiomer for Formula (I), or a pharmaceutically-acceptable salt, or hiohydrolyzable amide, ester, or imide thereof.

2. The compound of claim 1, wherein Y is independently one or more of hydrogen, hydroxy, $SR_3$, alkoxy, amino, wherein amino is of formula $NR_6,R_7$, wherein $R_6$ and $R_7$ are independently chosen from hydrogen, alkyl, heteroalkyl, $SO_2R8$, $COR_9$; and $R_8$ is alkyl, aryl, heteroaryl, or heteroalkyl.

3. The compound of claim 1, wherein Ar is phenyl or substituted phenyl.

4. The compound of claim 3, wherein Ar is substituted phenyl and the substitution is with hydroxy, alkoxy, nitro or halo.

5. The compound of claim 4, wherein Ar is substituted with methoxy, bromo, nitro and butoxy.

6. The compound of claim 5, wherein Ar is substituted at the ortho or para position relative to the sulfonyl.

7. The compound of claim 1, wherein W is one or more of hydrogen or C1 to C4 alkyl.

8. The compound of claim 1, wherein W is geminal C1 to C4 alkyl.

9. The compound of claim 1 wherein the spiro group, Z, forms a 5 to 7 membered ring with the carbon to which it is attached.

10. The compound of claim 9 wherein the spiro ring is unsubstituted or substituted with a fused ring.

11. The compound according to claim 10, wherein Z has one or more heteroatoms chosen from oxygen or sulfur.

12. A pharmaceutical composition comprising:0
   (a) a safe and effective amount of a compound of claim 1; and
   (b) a pharmaceutically-acceptable carrier.

13. A pharmaceutical composition comprising:
   (a) a safe and effective amount of a compound of claim 4; and
   (b) a pharmaceutically-acceptable carrier.

14. A pharmaceutical composition comprising:
   (a) a safe and effective amount of a compound of claim 5; and
   (b) a pharmaceutically-acceptable carrier.

15. A pharmaceutical composition comprising:
   (a) a safe and effective amount of a compound of claim 9; and
   (b) a pharmaceutically-acceptable carrier.

16. A pharmaceutical composition comprising:
   (a) a safe and effective amount of a compound of claim 10; and
   (b) a pharmaceutically-acceptable carrier.

17. A method for treating a disease associated with unwanted metalloprotease activity in a mammalian subject, the method comprising administering to said subject a safe and effective amount of a compound of claim 1.

18. A method for treating a disease associated with unwanted metalloprotease activity in a mammalian subject, the method comprising administering to said subject a safe and effective amount of a compound of claim 4.

19. A method for treating a disease associated with unwanted metalloprotease activity in a human or other animal subject, the method comprising administering to said subject a safe and effective amount of a compound of claim 5.

20. A method for treating a disease associated with unwanted metalloprotease activity in a mammalian subject, the method comprising administering to said subject a safe and effective amount of a compound of claim 9.

21. A method for treating a disorder modulated by metalloproteases, wherein the disorder is chosen from the group comprising, arthritis, cancer, cardiovascular disorders, skin disorders, ocular disorders, inflammation and gum disease by administering to a mammal in need of such treatment, a safe and effective amount of a metalloprotease inhibitor according to claim 1.

22. A method for treating a disorder according to claim 21, wherein the disorder is arthritis, and is chosen from the group comprising, osteoarthritis and rheumatoid arthritis.

23. A method for treating a disorder according to claim 21, wherein the disorder is cancer, and the treatment prevents or arrests tumor growth and metastasis.

24. A method for treating a disorder according to claim 21, wherein the disorder is a cardiovascular disorder chosen from the group compromising dilated cardiomyopathy, congestive heart failure, atherosclerosis, plaque rupture, reperfusion injury, ischemia, chronic obstructive pulmonary disease, angioplasty restenosis and aortic aneurysm.

25. A method for treating a disorder according to claim 21, wherein the disorder is an ocular disorder, and is chosen from the group comprising, corneal ulceration, lack of corneal healing, macular degeneration, and pterygium.

26. A method for treating a disorder according to claim 21, wherein the disorder is gum disease, and is chosen from the group comprising, periodontal disease, and gingivitis.

27. A method for treating a condition, according to claim 21, wherein the condition is skin condition chosen from the group comprising wrinkle repair and prevention, U. V. skin damage, epidermolysis bullosa, psoriasis, sclerodema, atopic dermatitis and scarring.

28. A method for preventing the loosening of prosthetic devices chosen from the group comprising joint replacements and dental prosthesis by administering to a mammal in need of such treatment, a safe and effective amount of a metalloprotease inhibitor according to claim 1.

29. A method for treating inflammatory conditions according to claim 21, chosen from the group comprising inflammatory bowel disease, Crohn's Disease, ulcerative colitis, pancreatitis, diverticulitis, acne inflammation, osteomylitis, bronchitis, arthritis, asthma.

30. A method of treating multiple sclerosis, comprising administering to a mammal in need of such treatment, a safe and effective amount of a metalloprotease inhibitor according to claim 1.

31. A method for treating musculoskeletal disease or cachexia comprising administering to a mammal in need of such treatment, a safe and effective amount of a metalloprotease inhibitor according to claim 1.

* * * * *

UNITED STATES PATENT AND TRADEMARK OFFICE
CERTIFICATE OF CORRECTION

| | |
|---|---|
| PATENT NO. | : 6,015,912 |
| APPLICATION NO. | : 08/918328 |
| DATED | : January 18, 2000 |
| INVENTOR(S) | : Wang et al. |

It is certified that error appears in the above-identified patent and that said Letters Patent is hereby corrected as shown below:

Column 7, line 18 of the issued patent, delete "mammalian source" and insert --"mammalian metalloprotease" means any metal-containing enzyme found in mammalian source--
Column 7, line 62 of the issued patent, delete "allyl" and insert --alkyl--
Column 22, line 29 of the issued patent, delete "triturated" and insert --titrated--
Column 22, line 33 of the issued patent, delete "4oxo" and insert --4-oxo--
Column 24, line 55 of the issued patent, delete "SN" and insert --8N--
Column 25, line 40 of the issued patent, insert --)-- after "R"
Column 26, line 56 of the issued patent, delete "4methoxyphenylsulfonyl" and insert --4-methoxyphenylsulfonyl--
Column 28, line 54 of the issued patent, delete "4dioxo" and insert --4-dioxo--
Column 28, line 54 of the issued patent, delete "(3R)trans" and insert --(3R)-trans--
Column 32, line 9 of the issued patent, delete "8azaspiro" and insert --8-azaspiro--
Column 33, line 63 of the issued patent, delete "4dioxo" and insert --4-dioxo--
Column 33, line 63 of the issued patent, delete "l" and insert --1--
Column 33, line 64 of the issued patent, delete "(3S)methyl" and insert --(3S)-methyl--
Column 34, line 9 of the issued patent, delete "4dioxo" and insert --4-dioxo--
Column 35, line 60 of the issued patent, delete "1"
Column 36, line 11 of the issued patent, delete "4dioxo" and insert --4-dioxo--
Column 37, line 18 of the issued patent, delete "$_4$" and insert --4--
Column 37, line 32 of the issued patent, delete "$_{NH+}$" and insert --NH+--
Column 37, line 54 of the issued patent, delete "M" and insert --m--
Column 39, line 40 of the issued patent, delete "4methoxyphenylsulfonyl" and insert --4-methoxyphenylsulfonyl--
Column 40, line 38 of the issued patent, delete "4methoxyphenylsulfonyl" and insert --4-methoxyphenylsulfonyl--
Column 42, line 63 of the issued patent, delete "I" and insert --[--
Column 43, line 15 of the issued patent, delete "14.5.01" and insert --[4.5.0]--
Column 43, line 50 of the issued patent, delete "methoxyphenyisulfonyl" and insert --methoxyphenylsulfonyl--
Column 45, line 29 of the issued patent, delete "butyldicarbonate" and insert --butyldicarbonate--
Column 45, line 29 of the issued patent, insert -- - -- before and after the "4"
Column 45, line 29 of the issued patent, delete "BH3-THF" and insert --BH3•THF--
Column 46, line 34 of the issued patent, delete "S" and insert --8--
Column 46, line 34 of the issued patent, delete "1" and insert --t--
Column 46, line 37 of the issued patent, delete "pdioxane" and insert --p-dioxane--
Column 49, line 66 of the issued patent, delete "butoxyphenyisulfonyl" and insert --butoxyphenylsulfonyl--
Column 52, line 9 of the issued patent, delete "(2R)methyl" and insert --(2R)-methyl--
Column 52, line 9 of the issued patent, delete "(3R)methyl" and insert --(3R)-methyl--

UNITED STATES PATENT AND TRADEMARK OFFICE
CERTIFICATE OF CORRECTION

PATENT NO. : 6,015,912
APPLICATION NO. : 08/918328
DATED : January 18, 2000
INVENTOR(S) : Wang et al.

It is certified that error appears in the above-identified patent and that said Letters Patent is hereby corrected as shown below:

Column 55 of the issued patent, delete the second "Example 12" and insert --Example 13--
Column 60, line 45 of the issued patent, delete "I" and insert --I--
Column 62, line 20 of the issued patent, delete "allene" and insert --alkylene--
Column 62, line 24 of the issued patent, delete "$SOR_1$" and insert --$SOR_4$--
Column 62, line 27 of the issued patent, delete "$SO_2,R_8$" and insert --$SO_2R_8$--
Column 62, line 48 of the issued patent, delete "$SO_2R8$" and insert --$SO_2R_8$--

Signed and Sealed this

Thirty-first Day of July, 2007

JON W. DUDAS
*Director of the United States Patent and Trademark Office*